US011286299B2

(12) United States Patent
Xue et al.

(10) Patent No.: US 11,286,299 B2
(45) Date of Patent: Mar. 29, 2022

(54) PEPTIDES SELECTIVE FOR BCL-2 FAMILY PROTEINS

(71) Applicants: Massachusetts Institute of Technology, Cambridge, MA (US); Trustees of Dartmouth College, Hanover, NH (US)

(72) Inventors: Vincent Xue, Somerville, MA (US); Justin Michael Jenson, Cambridge, MA (US); Amy E. Keating, Arlington, MA (US); Jianfu Zhou, White River Junction, VT (US); Gevorg Grigoryan, Hanover, NH (US)

(73) Assignees: Massachusetts Institute of Technology, Cambridge, MA (US); Trustees of Darthmouth College, Hanover, NH (US)

( * ) Notice: Subject to any disclaimer, the term of this patent is extended or adjusted under 35 U.S.C. 154(b) by 0 days.

(21) Appl. No.: 16/573,881

(22) Filed: Sep. 17, 2019

(65) Prior Publication Data

US 2020/0262914 A1 Aug. 20, 2020

Related U.S. Application Data

(60) Provisional application No. 62/732,518, filed on Sep. 17, 2018.

(51) Int. Cl.
*C07K 16/28* (2006.01)
*G01N 33/53* (2006.01)

(52) U.S. Cl.
CPC ............. *C07K 16/28* (2013.01); *G01N 33/53* (2013.01)

(58) Field of Classification Search
CPC .............. A61K 38/00; A61K 39/39558; A61K 49/0056; A61K 2039/55516; C12Q 1/6886; G01N 33/574; G01N 33/502; C12N 2503/02
See application file for complete search history.

(56) References Cited

U.S. PATENT DOCUMENTS

| 5,446,090 A | 8/1995 | Harris |
| 6,348,558 B1 | 2/2002 | Harris et al. |
| 7,723,468 B2 | 5/2010 | Daffre et al. |
| 2004/0067503 A1 | 4/2004 | Tan et al. |
| 2005/0250680 A1 | 11/2005 | Walensky et al. |
| 2006/0073161 A1* | 4/2006 | Breton .................. C12Q 1/689 424/190.1 |
| 2008/0027145 A1 | 1/2008 | Huang |
| 2008/0199890 A1 | 8/2008 | Letai |
| 2009/0092582 A1 | 4/2009 | Bogin et al. |
| 2009/0275519 A1 | 11/2009 | Nash et al. |
| 2010/0273704 A1 | 10/2010 | Korsmeyer et al. |
| 2010/0286057 A1 | 11/2010 | Walensky et al. |
| 2012/0172285 A1 | 7/2012 | Walensky et al. |
| 2014/0363434 A1 | 12/2014 | Lasters et al. |
| 2015/0045310 A1 | 2/2015 | Link et al. |
| 2016/0095315 A1 | 4/2016 | Wei et al. |
| 2018/0128813 A1 | 5/2018 | Letai et al. |
| 2018/0201658 A1 | 7/2018 | Rezaei-Araghi et al. |
| 2019/0077840 A1 | 3/2019 | Rezaei-Araghi et al. |
| 2019/0185531 A1 | 6/2019 | Keating et al. |

FOREIGN PATENT DOCUMENTS

| WO | WO1997028819 | * | 8/1997 | ............. A61K 39/12 |
| WO | WO1999/014259 | | 3/1999 | |
| WO | WO1999/034833 | | 7/1999 | |
| WO | WO2006000034 A1 | * | 6/2006 | ............... C07K 5/50 |
| WO | WO2006/135985 | | 12/2006 | |
| WO | WO2008104000 A2 | * | 8/2008 | ............... C07K 5/08 |
| WO | WO2008/121767 | | 10/2008 | |
| WO | WO2010/060112 | | 5/2010 | |
| WO | WO2010/068684 | | 6/2010 | |
| WO | WO2010/148335 | | 12/2010 | |
| WO | WO2013/116829 | | 8/2013 | |
| WO | WO2016149613 A2 | * | 9/2016 | ............. A61K 38/16 |

OTHER PUBLICATIONS

U.S. Appl. No. 12/525,123, filed Mar. 18, 2010, Bernal et al.
Adams et al., "Measuring the sequence-affinity landscape of antibodies with massively parallel titration curves," eLife, Dec. 30, 2016, 5, 1-27.
Alford et al., "The Rosetta All-Atom Energy Function for Macromolecular Modeling and Design," Journal of Chemical Theory and Computation, Jun. 13, 2017, 13(6), 3031-3048.
Altschul et al., "Gapped BLAST and PSI-BLAST: a new generation of protein database search programs," Nucleic Acids Res., Sep. 1, 1997, 25: 3389-3402.
Araghi et al., "Rapid Optimization of Mcl-1 Inhibitors using Stapled Peptide Libraries Including Non-Natural Side Chains," ACS Chem. Biol., Epub, May 20, 2016 19, 11(5):1238-44; p. 1239, Table 1.
Arkadash et al., "Development of High Affinity and High Specificity Inhibitors of Matrix Metalloproteinase 14 through Computational Design and Directed Evolution," Journal of Biological Chemistry, Jan. 13, 2017, 292(8), 3481-3495.
Arkin et al., (2014). "Small-Molecule Inhibitors of Protein-Protein Interactions: Progressing toward the Reality," Chemistry & Biology, Sep. 18, 2014, 21(9), 1102-1114.
Armstrong et al., "The (i,i+4) Phe-His Interaction Studied in an Alanine-based α-Helix," Journal of Molecular Biology, Mar. 5, 1993, 230(1), 284.
Bechara et al., "Cell-penetrating peptides: 20 years later, where do we stand?," FEBS Lett., Jun. 19, 2013, 587(12):1693-1702.

(Continued)

*Primary Examiner* — Soren Harward
(74) *Attorney, Agent, or Firm* — Fish & Richardson P.C.

(57) ABSTRACT

Provided herein are peptides selective for combinations of Mcl-1/Bfl-1/Bcl-xL. Also provided are compositions containing these polypeptides and methods of using such peptides in the treatment of cancer that include administering to a subject one of the polypeptides.

9 Claims, 11 Drawing Sheets

Specification includes a Sequence Listing.

(56) References Cited

OTHER PUBLICATIONS

Bedbrook et al., "Machine learning to design integral membrane channelrhodopsins for efficient eukaryotic expression and plasma membrane localization," PLOS Computational Biology, Oct. 23, 2017, 13(10), 1-21.
Berger et al., "Computationally designed high specificity inhibitors delineate the roles of BCL2 family proteins in cancer," eLife, Nov. 2, 2016, 5, 1422-1432.
Berman et al., "The Protein Data Bank," Nucleic Acids Research, Jan. 1, 2000, 28(1), 235-242.
biorxiv.org [online] Zhou et al., "A general-purpose protein design framework based on mining sequence-structure relationships in experimentally-derived protein structures," available Oct. 1, 2018, retrieved Oct. 2, 2019, retrieved from URL <https://www.biorxiv.org/content/10.1101/431635v1>, 15 pages.
Bird et al., "Biophysical determinants for cellular uptake of hydrocarbon-stapled peptide helices," Nature Chemical Biology, Aug. 22, 2016, 12(10), 845-852.
Bird et al., "Chemical Synthesis of Hydrocarbon-Stapled Peptides for Protein Interaction Research and Therapeutic Targeting," Current Protocols in Chemical Biology, Sep. 1, 2011, 99-117.
Bird et al., "Synthesis and Biophysical Characterization of Stabilized a-Helices of BCL-2 Domains," Methods in Enzymol., Jan. 1, 2008, 446:369-386.
Blackwell et al., "Highly Efficient Synthesis of Covalently Cross-Linked Peptide Helices by Ring-Closing Metathesis," Angew Chem. Int. Ed. Dec. 1998, 37: 3281.
Blackwell et al., "Ring-Closing Metathesis of Olefinic Peptides: Design, Synthesis, and Structural Characterization of Macrocyclic Helical Peptides," J. Org. Chem., Aug. 10, 2001, 66: 5291-5302.
Boersma et al., "Hydrophile scanning as a complement to alanine scanning for exploring and manipulating protein-protein recognition: Application to the Bim BH3 domain," Protein Sci., Jul. 17, 2008, 17(7), 1232.
Bose et al., "Mcl-1 as a therapeutic target in acute myelogenous leukemia (AML)," Leukemia Research Reports, Jan. 1, 2013, 2(1), 12-14.
Burke et al., "Discovery of Trycyclic Indoles that Potently Inhibit Mcl-1 using Fragment-Based Methods and Structure-Based Design," J. Med. Chem., Apr. 17, 2015, 58(9), 3794.
Burnelle et al., "MCL-1-dependent leukemia cells are more sensitive to chemotherapy than BCL-2-dependent counterparts," J. Cell. Biol., Nov. 2, 2009, 187(3), 429.
Cang et al., "ABT-199 (venetoclax) and BCL-2 inhibitors in clinical development," Journal of Hematology & Oncology, Dec. 2015, 8(1): 1-8.
Chames et al., "Therapeutic antibodies: successes, limitations and hopes for the future," British Journal of Pharmacology. May 2009, 157: 220-33.
Chao et al., "Isolating and engineering human antibodies using yeast surface display," Nature Protocols, Aug. 2006, 1(2), 755-768.
Chatr-aryamontri et al., "The BioGRID interaction database: 2017 update," Nucleic Acids Research, Jan. 4, 2017, 45(D1), D369-D379.
Chaudhury et al., "PyRosetta: a script-based interface for implementing molecular modeling algorithms using Rosetta," Bioinformatics, Jan. 7, 2010, 26(5), 689-691.
Chen et al., "Designing specific protein-protein interactions using computation, experimental library screening, or integrated methods," Protein Science, Jul. 2012, 21(7), 949-963.
Chen et al., "Structure-Based Redesign of the Binding Specificity of Anti-Apoptotic Bcl-xL," Journal of Molecular Biology, Jan. 9, 2013, 425(1), 171-185.
Chevalier et al., "Massively parallel de novo protein design for targeted therapeutics," Nature Publishing Group; Oct. 2017, 550: 74-79.

Chica et al., "Generation of longer emission wavelength red fluorescent proteins using computationally designed libraries," Proceedings of the National Academy of Sciences, Nov. 23, 2010, 107(47), 20257-20262.
Choi et al., "Bcl-xL promotes metastasis independent of its anti-apoptotic activity," Nature Communications, Jan. 20, 2016, 7, 1-13.
Computational Design of Ligand Binding Proteins, 2016, Chapter 14, 15 pages.
Crooks et al., "WebLogo: A Sequence Logo Generator," Genome Research, 2004, 14(6), 1188-1190.
Czabotar et al., "Mutation to Bax beyond the BH3 Domain Disrupts Interactions with Pro-survival Proteins and Promotes Apoptosis," Journal of Biological Chemistry, Mar. 4, 2011, 286(9), 7123-7131.
Davey et al., "Improving the accuracy of protein stability predictions with multistate design using a variety of backbone ensembles." Proteins: Structure, Function, and Bioinformatics, 2013, 82(5), 771-784.
DeBartolo et al., "Genome-Wide Prediction and Validation of Peptides That Bind Human Prosurvival Bcl-2 Proteins," PLoS Computational Biology, Jun. 26, 2014, 10(6), 1-13.
DeBartolo et al., "Predictive Bcl-2 Family Binding Models Rooted in Experiment or Structure," Journal of Molecular Biology, Sep. 7, 2012, 422(1), 124-144.
Deng et al., "BH3 Profiling Identifies Three Distinct Classes of Apoptotic Blocks to Predict Response to ABT-737 and Conventional Chemotherapeutic Agents," Cancer Cell, Aug. 14, 2007, 12(2), 171.
Devi et al, "Antibodies to poly[(2→8)-a-N-acetylneuraminic acid] and poly[(2→9)a-N-acetylneuraminic acid] are elicited by immunization of mice with Escherichia coli K92 conjugates: Potential vaccines for groups B and C meningococci and E. coli K1," Proc. Natl. Acad. Sci. USA , Aug. 15, 1991, 88:7175-7179.
Dutta et al., "Determinants of BH3 Binding Specificity for Mcl-1 versus Bcl-xL," Journal of Molecular Biology, May 21, 2010, 398(5), 747-762.
Dutta et al., "Peptide Ligands for Pro-survival Protein Bfl-1 from Computationally Guided Library Screening," ACS Chemical Biology, Feb. 21, 2013, 8(4), 778-788.
Dutta et al., "Potent and Specific Peptide Inhibitors of Human Pro-Survival Protein Bcl-xL," Journal of Molecular Biology, Mar. 27, 2015, 427(6), 1241-1253.
Eckert et al., "Characterization of the steric defense of the HIV-1 gp41 N-trimer region," Protein Science, Dec. 2008, 17(12), 2091-2100.
Edgar "Search and clustering orders of magnitude faster than BLAST," Bioinformatics, Aug. 12, 2010, 26(19), 2460-2461.
Emsley et al., "Features and development of Coot," Acta Crystallographica Section D Biological Crystallography, Apr. 1, 2010, 66(4), 486-501.
European Supplementary Search Report in Appln. No. EP16765822, dated Jul. 24, 2018, 22 pages.
Fattom et al, "Serum Antibody Response in Adult Volunteers Elicited by Injection of Streptococus pneumoniae Type 12F Polysaccharide Alone or Conjugated to Diptheria Toxoid," Infect. Immun., Jul. 1990, 58:2309-2312.
Feng et al., "A topological and conformational stability alphabet for multipass membrane proteins," Nature Chemical Biology, Mar. 2016, 12(3), 167-173.
Fernandez-Fuentes et al., "A supersecondary structure library and search algorithm for modeling loops in protein structures," Nucleic Acids Research, Jan. 1, 2006, 34(7), 2085-2097.
Fire et al., "Mcl-1-Bim complexes accommodate surprising point mutations via minor structural changes," Protein Science, Mar. 2010, 19: 507-19.
Fleishman et al., "Computational Design of Proteins Targeting the Conserved Stem Region of Influenza Hemagglutinin," Science, May 13, 2011, 332(6031), 816-821.
Foight et al, "Enriching peptide libraries for binding affinity and specificity through computationally directed library design," Methods Mol. Biol., 2014, 1561:213-232.
Foight et al., "Designed BH3 Peptides with High Affinity and Specificity for Targeting Mcl-1 in Cells," ACS Chemical Biology, Jul. 23, 2014, 9(9), 1962-1968.

(56) References Cited

OTHER PUBLICATIONS

Foight et al., "Locating Herpesvirus Bcl-2 Homologs in the Specificity Landscape of Anti-Apoptotic Bcl-2 Proteins," Journal of Molecular Biology, Jul. 31, 2015, 427(15), 2468-2490.
Fowler et al., "High-resolution mapping of protein sequence-function relationships," Nature Methods, Sep. 2010, 7(9), 741-746.
Frappier et al., "PixelDB: Protein-peptide complexes annotated with structural conservation of the peptide binding mode," Protein Science, Jan. 2018, 27(1), 276-285.
Gai et al., "Yeast surface display for protein engineering and characterization," Current Opinion in Structural Biology, Aug. 1, 2007 17(4), 467-473.
Gautier et al., "HELIQUEST: a web server to screen sequences with specific-helical properties," Bioinformatics, Jul. 28, 2008, 24(18), 2101-2102.
Gietz et al, "Transformation of yeast by lithium acetate/single-stranded carrier DNA/polyethylene glycol method. Methods Enzymol," Jan. 1, 2002, 350:87-96.
Gorelik et al., "Inhibition of SCF ubiquitin ligases by engineered ubiquitin variants that target the Cul1 binding site on the Skp1-F-box interface," Proceedings of the National Academy of Sciences, Mar. 29, 2016, 113(13), 3527-3532.
Grigoryan et al., "Design of protein-interaction specificity gives selective bZIP-binding peptides," Nature, Apr. 2009, 458(7240), 859-864.
He et al., "Compositional Bias in Naïve and Chemically-modified Phage-Displayed Libraries uncovered by Paired-end Deep Sequencing," Scientific Reports, Jan. 19, 2018, 8(1), 1-14.
Henikoff et al., "Amino acid substitution matrices from protein blocks," Proceedings of the National Academy of Sciences, Nov. 15, 1992, 89(22), 10915-10919.
Herman et al., "Completing the family portrait of the anti-apoptotic Bcl-2 proteins: Crystal structure of human Bfl-1 in complex with Bim," FEBS Letters, Oct. 29, 2008, 582(25-26), 3590-3594.
Hiraki et al.,"Targeting MUC1-C suppresses BCL2A1 in triple-negative breast cancer," Signal Transduction and Targeted Therapy, May 12, 2018, 3(1): 1-8.
Jacobs et al., "Design of structurally distinct proteins using strategies inspired by evolution," Science, May 6, 2016, 352(6286), 687-690.
Jacobs et al., "SwiftLib: rapid degenerate-codon-library optimization through dynamic programming," Nucleic Acids Research, Dec. 24, 2015, 43(5), e34-e34.
Jenson et al "Peptide design by optimization on a data-parameterized protein interaction landscape," Proceedings of the National Academy of Sciences, Oct. 30, 2018, 115(44):E10342-E10351.
Jenson et al., "Epistatic mutations in PUMA BH3 drive an alternate binding mode to potently and selectively inhibit anti-apoptotic Bfl-1," Elife, Jun. 8, 2017, 6, 1-23.
Karanicolas et al., "Computational design of affinity and specificity at protein-protein interfaces," Current Opinion in Structural Biology, Aug. 1, 2009, 19(4), 458-463.
Kawanioto et al., "Design of Triazole-stapled BCL9 a-Helical Peptides to Target the B-Catenin/B-cell CLL/lymphoma 9 (BCL9) Protein-Protein Interaction," Journal of Medicinal Chemistry Jan. 24, 2012, 55:1137-1146.
Kim et al., "Synthesis of all-hydrocarbon stapled a-helical peptides by ring-closing olefin metathesis," Nat. Protoc., Jun. 2011, 6(6), 761.
Kingsford et al., "Solving and analyzing side-chain positioning problems using linear and integer programming," Bioinformatics, Nov. 16, 2004, 21(7), 1028-1039.
Koss et al., "Defining specificity and on-target activity of BH3-mimetics using engineered B-ALL cell lines," Oncotarget, Mar. 8, 2016, 7(10):11500-11511.
Kotschy et al., "The MCL1 inhibitor S63845 is tolerable and effective in diverse cancer models," Nature, Oct. 2016, 538(7626), 477-482.
Kritzer, "Stapled Peptides: Magic bullets in nature's arsenal," Nature Chemical Biology, Aug. 2010, vol. 6, No. 8, 566-567.
Kuang et al., "DOMMINO 2.0: integrating structurally resolved protein-, RNA-, and DNA-mediated macromolecular interactions," Database, Jan. 1, 2016, 2016: 1-2.
Kumar et al., "Novel Polymeric Nanoparticles for Intracellular Delivery of Peptide Cargos: Antitumor Efficacy of the BCL-2 Conversion Peptide NuBCP-9," Cancer Research, Jun. 15, 2014, 74(12), 3271-3281.
Larkin et al., "Clustal W and Clustal X version 2.0," Bioinformatics, Nov. 1, 2007, 23(21), 2947-2948.
Lee et al, "Conformational Changes in Bcl-2Pro-survival Proteins DetermineTheir Capacity to Bind Ligands," J. Biol. Chem., Oct. 30, 2009, 284:30508-30517.
Lee et al., "Novel Bcl-2 Homology-3 Domain-like Sequences Identified from Screening Randomized Peptide Libraries for Inhibitors of the Pro-survival Bcl-2 Proteins," Journal of Biological Chemistry, Nov. 6, 2009, 284(45), 31315-31326.
Lessen et al., "Structure-guided design of a selective BCL-XL inhibitor," Nature Chemical Biology, Jun. 2013, 9(6), 390-397.
Lewis et al., "Anchored Design of Protein-Protein Interfaces," PLoS ONE, Jun. 17, 2011, 6(6), 1-14.
Mackenzie et al., "Protein structural motifs in prediction and design," Current Opinion in Structural Biology, Jun. 1, 2017, 44, 161-167.
Mackenzie et al., "Tertiary alphabet for the observable protein structural universe," Proceedings of the National Academy of Sciences, Nov. 22, 2016, 113(47), E7438-E7447.
Malik et al., "Role of Capsid Structure and Membrane Protein Processing in Determining the Size and Copy Number of Peptides Displayed on the Major Coat Protein of Filamentous Bacteriophage," Journal of Molecular Biology, Jul. 5, 1996, 260(1), 9-21.
Matochko et al., "Prospective identification of parasitic sequences in phage display screens," Nucleic Acids Research, Nov. 9, 2013, 42(3), 1784-1798.
McConkey et al., "Discrimination of native protein structures using atom-atom contact scoring," Proceedings of the National Academy of Sciences, Mar. 18, 2003, 100(6), 3215-3220.
McCoy et al., "Phaser crystallographic software," Journal of Applied Crystallography, Aug. 1, 2007, 40(4):658-674.
Miles et al., "Hydrocarbon constrained peptides—understanding preorganisation and binding affinity," Chemical Science, 2016, 7(6), 3694-3702.
Moldoveanu et al., "Many players in BCL-2 family affairs," Trends in Biochemical Sciences, Mar. 1, 2014, 39(3), 101-111.
Montero et al., "Why do BCL-2 inhibitors work and where should we use them in the clinic?" Cell Death & Differentiation, Jan. 2018, 25(1), 56-64.
Muñoz et al., "Development of the multiple sequence approximation within the AGADIR model of α-helix formation: Comparison with Zimm-Bragg and Lifson-Roig formalisms," Biopolymers, Apr. 15, 1997, 41(5), 495-509.
Needleman et al., "A general method applicable to the search for similarities in the amino acid sequence of two proteins," Journal of Molecular Biology, Mar. 28, 1970 48(3), 443-453.
Negron et al., "A Set of Computationally Designed Orthogonal Antiparallel Homodimers that Expands the Synthetic Coiled-Coil Toolkit," Journal of the American Chemical Society, Nov. 13, 2014, 136(47), 16544-16556.
Nischan et al., "Covalent Attachment of Cyclic TAT Peptides to GFP Results in Protein Delivery into Live Cells with Immediate Bioavailability," Angewandte Chemie International Edition, Feb. 2, 2014, 54(6), 1950-1953.
Olsson et al., "Upregulation of bfl-1 is a potential mechanism of chemoresistance in B-cell chronic lymphocytic leukaemia," British Journal of Cancer, Sep. 2007, 97(6), 769-777.
Oltersdorf et al., "An inhibitor of Bcl-2 family proteins induces regression of solid tumours," Nature, Jun. 2005, 435(7042), 677-681.
Opferman, "Attacking cancer's Achilles heel: antagonism of anti-apoptotic BCL-2 family members," The FEBS Journal, Jul. 1, 2015, 283(14), 2661-2675.

(56) References Cited

OTHER PUBLICATIONS

Otwinowski et al., "[20] Processing of X-ray diffraction data collected in oscillation mode," Methods Enzymol, Jan. 1, 1997, 276:307-326.
PCT International Search Report and Written Opinion in International Appln. No. PCT/US2017/43219, dated Jan. 8, 2018, 14 pages.
PCT International Search Report and Written Opinion in International Appln. No. PCT/US2019/51410, dated Feb. 18, 2020, 11 pages.
PCT International Search Report and Written Opinion in International Application No. PCT/US2016/059320. dated May 22, 2017, 10 pages.
PCT International Search Report and Written Opinion dated Sep. 23, 2016 in International Application No. PCT/US2016/023118, 17 pages.
PCT International Search Report in International Application No. PCT/US2013/024617, dated Jun. 20, 2013, 3 pages.
Potapov et al., "Data-Driven Prediction and Design of bZIP Coiled-Coil Interactions," PLOS Computational Biology, Feb. 19, 2015, 11(2), 1-29.
Procko et al., "A Computationally Designed Inhibitor of an Epstein-Barr Viral Bcl-2 Protein Induces Apoptosis in Infected Cells," Cell, Jun. 19, 2014, 157(7), 1644-1656.
Qian, et al., "Discovery and Mechanism of Highly Efficient Cyclic Cell-Penetrating Peptides," Biochemistry, Apr. 28, 2016, 55(18), 2601-2612.
Reich et al "Generating High-Accuracy Peptide-Binding Data in High Throughput with Yeast Surface Display and SORTCERY," Computational Design of Ligand Binding Proteins, 2016, 233-247.
Reich et al., "SORTCERY—A High-Throughput Method to Affinity Rank Peptide Ligands." Journal of Molecular Biology, Jun. 5, 2015, 427(11), 2135-2150.
Rezaei et al., "Iterative optimization yields Mcl-1-targeting stapled peptides with selective cytotoxicity to Mcl-1-dependent cancer cells," Proceedings of the National Academy of Sciences, Jan. 30, 2018, 115(5), E886-E895.
Roberts et al., "Computational Design of a PDZ Domain Peptide Inhibitor that Rescues CFTR Activity," PLoS Computational Biology, Apr. 19, 2012, 8(4), 1-13.
Roehrl et al., "A General Framework for Development and Data Analysis of Competitive High-Throughput Screens for Small-Molecule Inhibitors of Protein-Protein Interactions by Fluorescence Polarization," Biochemistry, Dec. 28, 2004, 43(51), 16056-16066.
Romero et al., "Navigating the protein fitness landscape with Gaussian processes," Proceedings of the National Academy of Sciences, Jan. 15, 2013, 110(3), E193-E201.
Roosenburg et al., "Stabilized 111 In-labeled sCCK8 analogues for targeting CCK2-receptor positive tumors: synthesis and evaluation," Bioconjugate Chem., Mar. 19, 2010, 21(4), 663-670.
Ryan et al., "BH3 profiling in whole cells by fluorimeter or FACS," Methods, Jun. 1, 2013, 61(2), 156-164.
Ryan et al., "Heightened mitochondiral priming is the basis for apoptotic hypersensitivity of CD4+CD8+ thymocytes," Proc. Natl. Acad. Sci., Jun. 20, 2010, 107(29), 12895-900.
Ryan et al., "iBH3: simple, fixable BH3 profiling to determine apoptotic priming in primary tissue by flow cytometr," Biol. Chem., Jul. 1, 2016, 397:671-678.
Ryvkin et al., "Phage display peptide libraries: deviations from randomness and correctives," Nucleic Acids Research, Feb. 6, 2018, 46(9), e52-e52.
Salvat et al., "Computationally optimized deimmunization libraries yield highly mutated enzymes with low immunogenicity and enhanced activity," Proceedings of the National Academy of Sciences, Jun. 27, 2017, 1-9.
Schafmeister et al, "An All-Hydrocarbon Cross-Linking System for Enhancing the Helicity and Metabolic Stability of Peptides," J. Am. Chem. Soc., Jun. 21, 2000, 122:5891-5892.
Scherr et al., "Bcl-xL is an oncogenic driver in colorectal cancer," Cell Death & Disease, Aug. 2016, 7(8), e2342-e2342.
Schoenwaelder et al., "Bcl-xL-inhibitory BH3 mimetics can induce a transient thrombocytopathy that undermines the hemostatic function of platelets," Blood, Aug. 11, 2011, 118(6), 1663-1674.
Schwarze et al., "In Vivo Protein Transduction: Delivery of a Biologically Active Protein into the Mouse," Science, Sep. 3, 1999, 285(5433), 1569-1572.
Schymkowitz et al., "The FoldX web server: an online force field," Nucleic Acids Research, Jul. 1, 2005, 33 (Web Server), W382-W388.
Senft et al., "Selective Induction of Cell Death in Melanoma Cell Lines through Targeting of Mcl-1 and A1," PLoS ONE, Jan. 24, 2012, 7(1), 1-11.
Shannon & Weerapana, "Covalent protein modification: the current landscape of residue-specific electrophiles," Curr. Opin. Chem. Biol., Feb. 1, 2015, 24, 18-26.
Shirian et al., "Converting a broad matrix metalloproteinase family inhibitor into a specific inhibitor of MMP-9 and MMP-14," FEBS Letters, Apr. 1, 2018 592(7), 1122-1134.
Smola et al., "A tutorial on support vector regression," Statistics and computing, Aug. 1, 2004, 14(3):199-222.
Souers et al., "ABT-199, a potent and selective BCL-2 inhibitor, achieves antitumor activity while sparing platelets," Nature Medicine, Feb. 2013, 19(2), 202-208.
Stebbins et al., "Structure-based design of covalent Siah inhibitors," Chem Biol., Aug. 22, 2013, 20(8):973-82.
Stewart et al., "The MCL-1 BH3 Helix is an Exclusive MCL-1 inhibitor and Apoptosis Sensitizer," Nat. Chem. Biol., Aug. 2010, 6(8), 1-17.
Szu et al, "Comparative Immunogenicities of Vi Polysaccharide-Protein Conjugates Composed of Cholera Toxin or Its B Subunit as a Carrier Bound to High- or Lower-Molecular-Weight Vi," Infection and Immunity, Dec. 1, 1989, 57:3823-3827.
Szu et al, "Laboratory and Preliminary Clinical Characterization of Vi Capsular Polysaccharide-Protein Conjugate Vaccines," Infect. Immun., Oct. 1, 1994, 62:4440-4444.
Szu et al, "Vi Capsular Polysaccharide-Protein Conjugates for Prevention of Typhoid Fever," J. Exp. Med., Nov. 1, 1987, 166:1510-1524.
Szu et al., "Relation between Structure and Immunologic Properties of the Vi Capsular Polysaccharide," Infect. Immun., Sep. 7, 1991, 59:4555-4561.
Tompa et al., "A Million Peptide Motifs for the Molecular Biologist," Molecular Cell, Jul. 17, 2014, 55(2), 161-169.
UniProt Consortium, "UniProt: the universal protein knowledgebase," Nucleic Acids Research, Nov. 28, 2016, 45(D1), D158-D169.
Vanhee et al., "BriX: a database of protein building blocks for structural analysis, modeling and design," Nucleic Acids Research, Oct. 22, 2010, 39(suppl 1), D435-D442.
Verma et al., "Pareto optimization of combinatorial mutagenesis libraries," IEEE/ACM Transactions on Computational Biology and Bioinformatics, Jul. 23, 2018, 1-12.
Walensky et al, "Activation of Apoptosis in Vivo by a Hydrocarbon-Stapled BH3 Helix," Science, Sep. 3, 2004, 305:1466-1470.
Walensky et al., "Hydrocarbon-Stapled Peptides: Principles, Practice, and Progress," Journal of Medicinal Chemistry, Mar. 6, 2014, 57(15), 6275-6288.
Wang et al., "Alignment of distantly related protein structures: algorithm, bound and implications to homology modeling," Bioinformatics, Jul. 26, 2011, 27(18), 2537-2545.
Wenzel et al., "MCL1 is deregulated in subgroups of diffuse large B-cell lymphoma," Leukemia, Jun. 2012, 27(6), 1381-1390.
Whitehead et al., "Optimization of affinity, specificity and function of designed influenza inhibitors using deep sequencing," Nature Biotechnology, Jun. 2012, 30(6), 543-548.
Wilen et al, "Strategies in Optical Resolutions," Tetrahedron, Jan. 1, 1977, 33:2725-2736.
Wilen et al., "Tables of Resolving Agents and Optical Resolutions", p. 268, University of Notre Dame Press, 1972.
Williams et al., "Asymmetric Synthesis of Monosubstituted and a, a-Disubstituted-Amino Acids via Diastereoselective Glycine Enolate Alkylations," J. Am. Chem. Soc., Nov. 1991, 113: 9276.
Williams et al., "Efficient Asymmetric Synthesis of N-tert-Butoxycarbonyl ☐-Aminoacids Using 4-tert-Butoxycarbonyl-5,6-

(56) References Cited

OTHER PUBLICATIONS

Diphenylmorpholin-2-One: (R)-(Ntert-Butoxycarbonyl)Allylglycine [(4-Pentenoic acid, 2-[[(1,1-dimethylethoxy)carbonyl]amino]-, (2R)-)]," Org. Synth., Apr. 28, 2003, 80:31.

Wong et al., "Direct visualization of Bcl-2 family protein interactions using live cell fluorescent protein redistribution assays," Cell death & disease, Mar. 3, 2012; 3(3): 1-10.

Xiao et al., "Immobilized OBOC combinatorial bead array to facilitate multilicative screening," Comb. Chem. High Throughput Screen, Jul. 1, 2013, 16(6), 441.

Yecies et al., "Acquired resistance to ABT-737 in lymphoma cells that up-regulate Mcl-1 and BFL-1," Blood, Apr. 22, 2010, 115(16), 3304-3313.

Zheng et al., "Computational Design of Selective Peptides to Discriminate between Similar PDZ Domains in an Oncogenic Pathway," Journal of Molecular Biology, Jan. 30, 2015, 427(2), 491-510.

Zheng et al., "Sequence statistics of tertiary structural motifs reflect protein stability," PLOS ONE, May 26, 2017, 12(5), 1-25.

Zheng et al., "Tertiary Structural Propensities Reveal Fundamental Sequence/Structure Relationships," Structure, May 5, 2015, 23(5), 961-971.

Henchey et al., "Contemporary strategies for the stabilization of peptides in the α-helical conformation," Current Opinion in Chemical Biology, Dec. 1, 2008, 12(6):692-7.

Okamoto et al., "Stabilizing the pro-apoptotic BimBH3 helix (BimSAHB) does not necessarily enhance affinity or biological activity," ACS Chemical Biology, Feb. 15, 2013, 8(2):297-302.

\* cited by examiner

● Peptides with measurements for all three proteins (1,852)

A

B

C

D

E

A

B

C

D

SEQUENCE LISTING

```
<160> NUMBER OF SEQ ID NOS: 137

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: W, P, G, A, R, or T
<220> FEATURE:
<221> NAME/KEY: MOD_RES
<222> LOCATION: (4)..(4)
<223> OTHER INFORMATION: M, L, E, or I
<220> FEATURE:
<221> NAME/KEY: MOD_RES
<222> LOCATION: (5)..(5)
<223> OTHER INFORMATION: L, Y, or F
<220> FEATURE:
<221> NAME/KEY: MOD_RES
<222> LOCATION: (6)..(6)
<223> OTHER INFORMATION: E, D, or H
<220> FEATURE:
<221> NAME/KEY: MOD_RES
<222> LOCATION: (7)..(7)
<223> OTHER INFORMATION: L, Y, or F
<220> FEATURE:
<221> NAME/KEY: MOD_RES
<222> LOCATION: (8)..(8)
<223> OTHER INFORMATION: D, V, G, A, S, or I
<220> FEATURE:
<221> NAME/KEY: MOD_RES
<222> LOCATION: (10)..(10)
<223> OTHER INFORMATION: L, D, Q, or E
<220> FEATURE:
<221> NAME/KEY: MOD_RES
<222> LOCATION: (12)..(12)
<223> OTHER INFORMATION: T, V, G, A, R, or I
<220> FEATURE:
<221> NAME/KEY: MOD_RES
<222> LOCATION: (14)..(14)
<223> OTHER INFORMATION: L, Y, or F
<220> FEATURE:
<221> NAME/KEY: MOD_RES
<222> LOCATION: (17)..(17)
<223> OTHER INFORMATION: M, L, E, or I
<220> FEATURE:
<221> NAME/KEY: MOD_RES
<222> LOCATION: (18)..(18)
<223> OTHER INFORMATION: L, Y, or F
<220> FEATURE:
<221> NAME/KEY: MOD_RES
<222> LOCATION: (19)..(19)
<223> OTHER INFORMATION: L, V, A, or I
<220> FEATURE:
<221> NAME/KEY: MOD_RES
<222> LOCATION: (20)..(20)
<223> OTHER INFORMATION: T, K, E, or A
<220> FEATURE:
<221> NAME/KEY: MOD_RES
<222> LOCATION: (22)..(22)
<223> OTHER INFORMATION: L, Y, or F

<400> SEQUENCE: 1
```

```
Gly Gln Xaa Xaa Xaa Xaa Xaa Xaa Gln Xaa Leu Xaa Arg Xaa Gly Asp
1               5                   10                  15

Xaa Xaa Xaa Xaa Gln Xaa
            20
```

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: W, P, G, A, R, or T
<220> FEATURE:
<221> NAME/KEY: MOD_RES
<222> LOCATION: (4)..(4)
<223> OTHER INFORMATION: M, L, E, or I
<220> FEATURE:
<221> NAME/KEY: MOD_RES
<222> LOCATION: (5)..(5)
<223> OTHER INFORMATION: L, Y, or F
<220> FEATURE:
<221> NAME/KEY: MOD_RES
<222> LOCATION: (6)..(6)
<223> OTHER INFORMATION: E, D, or H
<220> FEATURE:
<221> NAME/KEY: MOD_RES
<222> LOCATION: (7)..(7)
<223> OTHER INFORMATION: V or I
<220> FEATURE:
<221> NAME/KEY: MOD_RES
<222> LOCATION: (10)..(10)
<223> OTHER INFORMATION: L, Y, or F
<220> FEATURE:
<221> NAME/KEY: MOD_RES
<222> LOCATION: (14)..(14)
<223> OTHER INFORMATION: V or I
<220> FEATURE:
<221> NAME/KEY: MOD_RES
<222> LOCATION: (17)..(17)
<223> OTHER INFORMATION: M, L, E, or I
<220> FEATURE:
<221> NAME/KEY: MOD_RES
<222> LOCATION: (18)..(18)
<223> OTHER INFORMATION: V or I
<220> FEATURE:
<221> NAME/KEY: MOD_RES
<222> LOCATION: (19)..(19)
<223> OTHER INFORMATION: L, D, Q, or E
<220> FEATURE:
<221> NAME/KEY: MOD_RES
<222> LOCATION: (20)..(20)
<223> OTHER INFORMATION: T, K, E, or A
<220> FEATURE:
<221> NAME/KEY: MOD_RES
<222> LOCATION: (22)..(22)
<223> OTHER INFORMATION: L, Y, or F

<400> SEQUENCE: 2

```
Gly Gln Xaa Xaa Xaa Xaa Xaa Ala Gln Xaa Leu Arg Arg Xaa Gly Asp
1               5                   10                  15

Xaa Xaa Xaa Xaa Gln Xaa
            20
```

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic

```
                        peptide
<220> FEATURE:
<221> NAME/KEY: MOD_RES
<222> LOCATION: (3)..(3)
<223> OTHER INFORMATION: W, P, G, A, R, or T
<220> FEATURE:
<221> NAME/KEY: MOD_RES
<222> LOCATION: (4)..(4)
<223> OTHER INFORMATION: M, L, E, or I
<220> FEATURE:
<221> NAME/KEY: MOD_RES
<222> LOCATION: (5)..(5)
<223> OTHER INFORMATION: R, V, Y, D, or I
<220> FEATURE:
<221> NAME/KEY: MOD_RES
<222> LOCATION: (6)..(6)
<223> OTHER INFORMATION: E, D, or H
<220> FEATURE:
<221> NAME/KEY: MOD_RES
<222> LOCATION: (7)..(7)
<223> OTHER INFORMATION: T, L, I, or F
<220> FEATURE:
<221> NAME/KEY: MOD_RES
<222> LOCATION: (8)..(8)
<223> OTHER INFORMATION: V, G, A, or S
<220> FEATURE:
<221> NAME/KEY: MOD_RES
<222> LOCATION: (10)..(10)
<223> OTHER INFORMATION: L, Y, or F
<220> FEATURE:
<221> NAME/KEY: MOD_RES
<222> LOCATION: (12)..(12)
<223> OTHER INFORMATION: R, A, or K
<220> FEATURE:
<221> NAME/KEY: MOD_RES
<222> LOCATION: (14)..(14)
<223> OTHER INFORMATION: L, V, A, or I
<220> FEATURE:
<221> NAME/KEY: MOD_RES
<222> LOCATION: (17)..(17)
<223> OTHER INFORMATION: M, L, E, or I
<220> FEATURE:
<221> NAME/KEY: MOD_RES
<222> LOCATION: (18)..(18)
<223> OTHER INFORMATION: L, Y, or F
<220> FEATURE:
<221> NAME/KEY: MOD_RES
<222> LOCATION: (19)..(19)
<223> OTHER INFORMATION: H, D, Q, V, N, or E
<220> FEATURE:
<221> NAME/KEY: MOD_RES
<222> LOCATION: (20)..(20)
<223> OTHER INFORMATION: T, K, E, or A
<220> FEATURE:
<221> NAME/KEY: MOD_RES
<222> LOCATION: (22)..(22)
<223> OTHER INFORMATION: L, V, A, or I

<400> SEQUENCE: 3

Gly Gln Xaa Xaa Xaa Xaa Xaa Xaa Gln Xaa Leu Xaa Arg Xaa Gly Asp
1               5                   10                  15

Xaa Xaa Xaa Xaa Gln Xaa
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: R, P, W, or A
<220> FEATURE:
```

```
<221> NAME/KEY: MOD_RES
<222> LOCATION: (4)..(4)
<223> OTHER INFORMATION: V or I
<220> FEATURE:
<221> NAME/KEY: MOD_RES
<222> LOCATION: (5)..(5)
<223> OTHER INFORMATION: D, Y, F, or I
<220> FEATURE:
<221> NAME/KEY: MOD_RES
<222> LOCATION: (6)..(6)
<223> OTHER INFORMATION: Q, H, or E
<220> FEATURE:
<221> NAME/KEY: MOD_RES
<222> LOCATION: (10)..(10)
<223> OTHER INFORMATION: D, Y, F, or I
<220> FEATURE:
<221> NAME/KEY: MOD_RES
<222> LOCATION: (12)..(12)
<223> OTHER INFORMATION: R, A, or K
<220> FEATURE:
<221> NAME/KEY: MOD_RES
<222> LOCATION: (14)..(14)
<223> OTHER INFORMATION: T, W, A, or S
<220> FEATURE:
<221> NAME/KEY: MOD_RES
<222> LOCATION: (17)..(17)
<223> OTHER INFORMATION: M, L, E, or I
<220> FEATURE:
<221> NAME/KEY: MOD_RES
<222> LOCATION: (19)..(19)
<223> OTHER INFORMATION: D or W
<220> FEATURE:
<221> NAME/KEY: MOD_RES
<222> LOCATION: (20)..(20)
<223> OTHER INFORMATION: T, K, E, or A
<220> FEATURE:
<221> NAME/KEY: MOD_RES
<222> LOCATION: (22)..(22)
<223> OTHER INFORMATION: L, A, Y, G, or I

<400> SEQUENCE: 4

Gly Gln Xaa Xaa Xaa Xaa Ile Ala Gln Xaa Leu Xaa Arg Xaa Gly Asp
1               5                   10                  15

Xaa Leu Xaa Xaa Gln Xaa
            20

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: W, P, G, A, R, or T
<220> FEATURE:
<221> NAME/KEY: MOD_RES
<222> LOCATION: (4)..(4)
<223> OTHER INFORMATION: M, L, E, or I
<220> FEATURE:
<221> NAME/KEY: MOD_RES
<222> LOCATION: (5)..(5)
<223> OTHER INFORMATION: V or I
<220> FEATURE:
<221> NAME/KEY: MOD_RES
<222> LOCATION: (6)..(6)
<223> OTHER INFORMATION: D or W
<220> FEATURE:
<221> NAME/KEY: MOD_RES
<222> LOCATION: (7)..(7)
<223> OTHER INFORMATION: L, Y, or F
<220> FEATURE:
<221> NAME/KEY: MOD_RES
<222> LOCATION: (10)..(10)
```

```
<223> OTHER INFORMATION: Q, E, or S
<220> FEATURE:
<221> NAME/KEY: MOD_RES
<222> LOCATION: (12)..(12)
<223> OTHER INFORMATION: R, A, or K
<220> FEATURE:
<221> NAME/KEY: MOD_RES
<222> LOCATION: (14)..(14)
<223> OTHER INFORMATION: M, Y, F, V, G, or A
<220> FEATURE:
<221> NAME/KEY: MOD_RES
<222> LOCATION: (17)..(17)
<223> OTHER INFORMATION: Q, M, D, V, or E
<220> FEATURE:
<221> NAME/KEY: MOD_RES
<222> LOCATION: (19)..(19)
<223> OTHER INFORMATION: Q, N, H, or A
<220> FEATURE:
<221> NAME/KEY: MOD_RES
<222> LOCATION: (20)..(20)
<223> OTHER INFORMATION: T, K, E, or A
<220> FEATURE:
<221> NAME/KEY: MOD_RES
<222> LOCATION: (22)..(22)
<223> OTHER INFORMATION: R, L, or Y

<400> SEQUENCE: 5

Gly Gln Xaa Xaa Xaa Xaa Xaa Gly Gln Xaa Leu Xaa Arg Xaa Ala Asp
1               5                   10                  15

Xaa Phe Xaa Xaa Gln Xaa
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: R, T, G, A, or S
<220> FEATURE:
<221> NAME/KEY: MOD_RES
<222> LOCATION: (4)..(4)
<223> OTHER INFORMATION: M, L, E, or I
<220> FEATURE:
<221> NAME/KEY: MOD_RES
<222> LOCATION: (5)..(5)
<223> OTHER INFORMATION: L, Y, or F
<220> FEATURE:
<221> NAME/KEY: MOD_RES
<222> LOCATION: (7)..(7)
<223> OTHER INFORMATION: L, V, A, or I
<220> FEATURE:
<221> NAME/KEY: MOD_RES
<222> LOCATION: (8)..(8)
<223> OTHER INFORMATION: V, G, A, or S
<220> FEATURE:
<221> NAME/KEY: MOD_RES
<222> LOCATION: (10)..(10)
<223> OTHER INFORMATION: L, D, Y, V, E, or I
<220> FEATURE:
<221> NAME/KEY: MOD_RES
<222> LOCATION: (12)..(12)
<223> OTHER INFORMATION: A, V, G, or I
<220> FEATURE:
<221> NAME/KEY: MOD_RES
<222> LOCATION: (17)..(17)
<223> OTHER INFORMATION: M, L, E, or I
<220> FEATURE:
<221> NAME/KEY: MOD_RES
<222> LOCATION: (18)..(18)
<223> OTHER INFORMATION: T, L, V, or I
<220> FEATURE:
```

```
<221> NAME/KEY: MOD_RES
<222> LOCATION: (19)..(19)
<223> OTHER INFORMATION: L, D, Q, N, V, A, T, E, or I
<220> FEATURE:
<221> NAME/KEY: MOD_RES
<222> LOCATION: (20)..(20)
<223> OTHER INFORMATION: T, E, or A

<400> SEQUENCE: 6

Gly Gln Xaa Xaa Xaa Asp Xaa Xaa Gln Xaa Leu Xaa Arg Leu Gly Asp
1               5                   10                  15

Xaa Xaa Xaa Xaa Gln Phe
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Arg Arg Ile Asp Glu Ile Ala Gln Ile Leu Arg Arg Ile Gly Asp
1               5                   10                  15

His Ile Glu Lys Tyr Ile
            20

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Arg Trp Ile Asp Gln Ile Ala Gln Phe Leu Arg Arg Ile Gly Asp
1               5                   10                  15

His Ile Glu Lys Tyr Ile
            20

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Arg Arg Val Asp Glu Ile Ala Gln Ile Leu Arg Arg Ile Gly Asp
1               5                   10                  15

Asn Ile Glu Glu Tyr Ile
            20

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Arg Arg Val Asp Glu Ile Ala Gln Ile Leu Arg Arg Ile Gly Asp
```

Asn Ile Asn Glu Tyr Ile
            20

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Arg Arg Ile Asp Glu Ile Ala Gln Ile Leu Arg Arg Ile Gly Asp
1               5                   10                  15

His Val Glu Lys Tyr Ile
            20

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Arg Arg Val Asp Glu Ile Ala Gln Ile Leu Arg Arg Ile Gly Asp
1               5                   10                  15

Asn Val Thr Thr Tyr Ile
            20

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Arg Arg Val Asp Glu Ile Ala Gln Ile Leu Arg Arg Ile Gly Asp
1               5                   10                  15

Gln Ile Glu Glu Tyr Ile
            20

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gln Trp Leu Arg Trp Val Ile Ala Glu Leu Ile Arg Ile Ala Asp
1               5                   10                  15

Glu Phe His Ala Gln Tyr
            20

<210> SEQ ID NO 15
<211> LENGTH: 22
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 15

Gly Gln Trp Leu Tyr Trp Val Ala Ala Glu Leu Val Arg Ile Ala Asp
1               5                   10                  15

Asp Phe Leu Ala Gln Arg
            20

<210> SEQ ID NO 16
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gln Ser Leu Ile Trp Phe Ile Ala Glu Leu Ala Arg Ile Gly Asp
1               5                   10                  15

Glu Phe His Glu Tyr Tyr
            20

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gln Trp Leu Ile Trp Tyr Ile Ala Glu Leu Ile Arg Ile Ala Asp
1               5                   10                  15

Glu Phe His Ala Gln Phe
            20

<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gln Trp Leu Arg Asp Val Val Ala Glu Leu Ala Arg Ile Ala Asp
1               5                   10                  15

Glu Phe His Ala Gln Tyr
            20

<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gln Trp Leu Ile Trp Tyr Ile Ala Glu Leu Arg Arg Tyr Ala Asp
1               5                   10                  15

Glu Phe His Ala Gln Ile
            20

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gln Trp Leu Ile Trp Val Ala Ala Gln Leu Arg Arg Tyr Ala Asp
1               5                   10                  15

Glu Phe His Ala Gln Arg
            20

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gln Trp Leu Ile Trp Tyr Ala Ala Glu Leu Ala Arg Leu Ala Asp
1               5                   10                  15

Asp Phe His Ala Gln Arg
            20

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gln Trp Leu Ile Trp Tyr Ala Ala Gln Leu Ala Arg Ile Ala Asp
1               5                   10                  15

Glu Phe His Ala Gln Arg
            20

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gln Ser Leu Ile Trp Tyr Ile Ala Glu Leu Ala Arg Ile Ala Asp
1               5                   10                  15

Glu Phe Ala Ala Gln Tyr
            20

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Gly Gln Arg Leu Ile Trp Ile Gly Ala Gly Leu Arg Arg Leu Ala Asp
1               5                   10                  15

Glu Phe Asp Lys Gln Ala
            20
```

```
<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gln Arg Ile Ile Trp Ile Ala Ala Glu Leu Arg Arg Ala Ala Asp
1               5                   10                  15

Glu Leu Asp Lys Gln Ile
            20
```

```
<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gln Arg Ile Ile Trp Ile Ala Ala Glu Leu Arg Arg Ala Ala Asp
1               5                   10                  15

Gln Leu Asp Ala Gln Ile
            20
```

```
<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gln Arg Ile Ile Trp Ile Gly Ala Glu Leu Arg Arg Leu Ala Asp
1               5                   10                  15

Glu Leu Asp Lys Gln Val
            20
```

```
<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gln Arg Ile Ile Trp Ile Ala Ala Glu Leu Arg Arg Ala Ala Asp
1               5                   10                  15

Gln Leu Asp Lys Gln Tyr
            20
```

```
<210> SEQ ID NO 29
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 29

Gly Gln Arg Ile Ile Trp Ile Ala Ala Gly Leu Arg Arg Leu Ala Asp
1               5                   10                  15

Glu Leu Asp Lys Gln Leu
            20

<210> SEQ ID NO 30
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gln Ala Leu Ile Trp Ile Gly Ala Glu Leu Arg Arg Leu Ala Asp
1               5                   10                  15

Glu Phe Asn Lys Gln Leu
            20

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gln Arg Leu Ile Trp Ile Gly Ala Glu Leu Arg Arg Leu Ala Asp
1               5                   10                  15

Glu Phe Asp Lys Gln Leu
            20

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gln Pro Leu Ile Trp Ile Gly Ala Glu Leu Arg Arg Leu Ala Asp
1               5                   10                  15

Glu Phe Asn Lys Gln Val
            20

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gln Arg Leu Ile Trp Ile Gly Ala Glu Leu Arg Arg Leu Ala Asp
1               5                   10                  15

Asp Phe Asp Lys Gln Tyr
            20
```

<210> SEQ ID NO 34
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gln Arg Leu Ile Trp Ile Gly Ala Glu Leu Arg Arg Leu Ala Asp
1               5                   10                  15

Glu Phe Asn Lys Gln Ala
            20

<210> SEQ ID NO 35
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Arg Ser Gln Ile Trp Tyr Val Gln Glu Leu Val Arg Gly Gly Asp
1               5                   10                  15

Val Asn His Ala Tyr Arg
            20

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Arg Ser Gln Ile Trp Tyr Asp Gln Glu Leu Val Arg Ser Gly Asp
1               5                   10                  15

Val Asn Ala Ala Tyr Arg
            20

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Arg Ser Gln Ile Trp Tyr Asp Gln Glu Leu Val Arg Ser Gly Asp
1               5                   10                  15

Glu Asn Ala Ala Tyr Arg
            20

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Arg Ser Gln Ile Trp Tyr Asp Gln Glu Leu Val Arg Tyr Ala Asp
1               5                   10                  15

Val Asn Ala Ala Tyr Arg
            20

<210> SEQ ID NO 39
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Arg Ser Gln Ile Trp Tyr Asp Gln Glu Leu Val Arg Tyr Gly Asp
1               5                   10                  15

Val Asn Ala Ala Tyr Arg
            20

<210> SEQ ID NO 40
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Arg Ser Gln Ile Trp Tyr Val Gln Glu Leu Val Arg Ser Gly Asp
1               5                   10                  15

Val Asn His Ala Tyr Arg
            20

<210> SEQ ID NO 41
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Arg Ser Glu Ile Trp Tyr Asp Gln Glu Leu Val Arg Ser Gly Asp
1               5                   10                  15

Val Asn Ala Ala Tyr Arg
            20

<210> SEQ ID NO 42
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Arg Arg Val Val Trp Ile Gly Gln Gly Leu Lys Arg Leu Ala Asp
1               5                   10                  15

Glu Tyr His Lys Tyr Ala
            20

<210> SEQ ID NO 43
<211> LENGTH: 22
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 43

Gly Arg Arg Glu Val Trp Leu Ser Gln Ser Leu Lys Arg Ile Ala Asp
1               5                   10                  15

Gln Phe Gln Lys Tyr Leu
            20

<210> SEQ ID NO 44
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Arg Arg Glu Ile Trp Leu Ser Gln Tyr Leu Lys Arg Ile Ala Asp
1               5                   10                  15

Leu Phe Gln Lys Tyr Leu
            20

<210> SEQ ID NO 45
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Arg Arg Glu Ile Trp Leu Ser Gln Ser Leu Lys Arg Ile Ala Asp
1               5                   10                  15

Met Phe Gln Lys Tyr Leu
            20

<210> SEQ ID NO 46
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Arg Arg Glu Ile Trp Leu Ser Gln Ser Leu Lys Arg Ile Ala Asp
1               5                   10                  15

Leu Phe Gln Lys Tyr Leu
            20

<210> SEQ ID NO 47
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gln Arg Val Asp Asp Phe Gly Gln Gly Leu Lys Arg Val Ala Asp
1               5                   10                  15

Glu Tyr His Ala Gln Ala
```

20

<210> SEQ ID NO 48
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Arg Arg Glu Val Trp Leu Ser Gln Ser Leu Lys Arg Ile Ala Asp
1               5                   10                  15

Gln Phe Gln Thr Tyr Leu
            20

<210> SEQ ID NO 49
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Arg Ser Glu Leu Glu Val Val Gln Glu Leu Val Arg Ile Gly Asp
1               5                   10                  15

Ile Val Val Ala Tyr Phe
            20

<210> SEQ ID NO 50
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Arg Ser Glu Tyr Glu Tyr Ile Gln Glu Leu Val Arg Ile Gly Asp
1               5                   10                  15

Glu Val Asp Ala Tyr Phe
            20

<210> SEQ ID NO 51
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Arg Ser Leu Tyr Glu Tyr Ile Gln Glu Leu Ile Arg Ile Gly Asp
1               5                   10                  15

Glu Val Thr Ala Tyr Phe
            20

<210> SEQ ID NO 52
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 52

Gly Arg Ser Leu Leu Glu Tyr Ile Gln Glu Leu Ile Arg Ile Gly Asp
1               5                   10                  15

Glu Val Ile Ala Tyr Phe
            20

<210> SEQ ID NO 53
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Arg Ser Glu Leu Glu Tyr Ile Gln Glu Leu Val Arg Ile Gly Asp
1               5                   10                  15

Glu Val Asp Ala Tyr Phe
            20

<210> SEQ ID NO 54
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Arg Gly Gln Leu Glu Tyr Ile Gln Glu Leu Ile Arg Ile Gly Asp
1               5                   10                  15

Ile Val Asp Ala Tyr Phe
            20

<210> SEQ ID NO 55
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Arg Ser Glu Leu Glu Tyr Ile Gln Glu Leu Ile Arg Ile Gly Asp
1               5                   10                  15

Asn Val Asp Ala Tyr Phe
            20

<210> SEQ ID NO 56
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Arg Ser Glu Leu Glu Tyr Ile Gln Glu Leu Ile Arg Ile Gly Asp
1               5                   10                  15

Ile Val Asp Ala Tyr Phe
            20

<210> SEQ ID NO 57
<211> LENGTH: 22
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Arg Ser Gln Tyr Glu Val Ile Gln Glu Leu Ile Arg Ile Gly Asp
1               5                   10                  15

Ile Val Leu Ala Tyr Phe
            20

<210> SEQ ID NO 58
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Arg Ser Glu Tyr Glu Tyr Ile Gln Glu Leu Ile Arg Ile Gly Asp
1               5                   10                  15

Asn Val Asp Ala Tyr Phe
            20

<210> SEQ ID NO 59
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Arg Ser Glu Tyr Glu Tyr Ile Gln Glu Leu Ile Arg Ile Gly Asp
1               5                   10                  15

Ile Val Asp Ala Tyr Phe
            20

<210> SEQ ID NO 60
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Arg Gly Gln Tyr Glu Tyr Ile Gln Glu Leu Ile Arg Ile Gly Asp
1               5                   10                  15

Ile Val Asp Ala Tyr Phe
            20

<210> SEQ ID NO 61
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gln Thr Leu Ile Trp Tyr Gly Ala Ser Leu Arg Arg Tyr Ala Asp
1               5                   10                  15
```

Glu Phe Ala Lys Gln Arg
            20

<210> SEQ ID NO 62
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gln Thr Leu Ile Trp Tyr Gly Ala Gln Leu Arg Arg Tyr Ala Asp
1               5                   10                  15

Glu Phe Ala Lys Gln Arg
            20

<210> SEQ ID NO 63
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gln Pro Leu Ile Trp Phe Gly Ala Ser Leu Arg Arg Gly Ala Asp
1               5                   10                  15

Glu Phe Ala Lys Gln Arg
            20

<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gln Thr Leu Ile Trp Tyr Gly Ala Gln Leu Arg Arg Val Ala Asp
1               5                   10                  15

Asp Phe Ala Lys Gln Arg
            20

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Gln Thr Ala Ile Trp Tyr Gly Ala Ser Leu Arg Arg Ala Ala Asp
1               5                   10                  15

Glu Phe Ala Lys Gln Arg
            20

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 66

Gly Gln Ser Leu Ile Trp Phe Gly Ala Ser Leu Arg Arg Gly Ala Asp
1               5                   10                  15

Glu Phe Ala Ala Gln Arg
            20

<210> SEQ ID NO 67
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Gln Pro Leu Ile Trp Phe Gly Ala Gln Leu Arg Arg Gly Ala Asp
1               5                   10                  15

Glu Phe Ala Ala Gln Arg
            20

<210> SEQ ID NO 68
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Gln Ser Met Ile Trp Tyr Gly Ala Ser Leu Arg Arg Ala Ala Asp
1               5                   10                  15

Glu Phe Ala Lys Gln Arg
            20

<210> SEQ ID NO 69
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gln Thr Leu Ile Trp Tyr Gly Ala Gln Leu Arg Arg Tyr Ala Asp
1               5                   10                  15

Asp Phe Ala Lys Gln Arg
            20

<210> SEQ ID NO 70
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gln Arg Leu Ile Trp Tyr Gly Ala Gln Leu Arg Arg Tyr Ala Asp
1               5                   10                  15

Asp Phe Ala Lys Gln Arg
            20

<210> SEQ ID NO 71
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gln Thr Leu Ile Trp Phe Gly Ala Ser Leu Arg Arg Gly Ala Asp
1               5                   10                  15

Glu Phe Ala Ala Gln Arg
            20

<210> SEQ ID NO 72
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Gln Gly Leu Ile Trp Tyr Gly Ala Gln Leu Arg Arg Val Ala Asp
1               5                   10                  15

Asp Phe Ala Lys Gln Arg
            20

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Arg Arg Val Arg His Ile Ala Gln Gly Leu Arg Arg Ala Gly Asp
1               5                   10                  15

Gln Leu Asp Ala Tyr Gly
            20

<210> SEQ ID NO 74
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Gln Arg Val Arg His Ile Ala Gln Gly Leu Arg Arg Thr Gly Asp
1               5                   10                  15

Gln Leu Asp Ala Tyr Gly
            20

<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Arg Arg Val Val His Ile Ala Ala Gly Leu Arg Arg Thr Gly Asp
1               5                   10                  15
```

```
Gln Leu Glu Ala Gln Gly
            20

<210> SEQ ID NO 76
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gln Arg Val Val His Ile Ala Ala Gly Leu Arg Arg Thr Gly Asp
1               5                   10                  15

Gln Leu Glu Ala Tyr Gly
            20

<210> SEQ ID NO 77
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Gln Arg Val Val His Ile Ala Gln Gly Leu Arg Arg Thr Gly Asp
1               5                   10                  15

Gln Leu Glu Ala Gln Gly
            20

<210> SEQ ID NO 78
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Gln Arg Val Val Gln Ile Ala Ala Gly Leu Arg Arg Thr Gly Asp
1               5                   10                  15

Gln Leu Glu Lys Tyr Gly
            20

<210> SEQ ID NO 79
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Gln Arg Val Val Gln Ile Ala Gln Gly Leu Arg Arg Thr Gly Asp
1               5                   10                  15

Gln Leu Glu Lys Gln Gly
            20

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 80

Gly Arg Arg Val Val Gln Ile Ala Ala Gly Leu Arg Arg Thr Gly Asp
1               5                   10                  15

Gln Leu Glu Lys Gln Gly
            20

<210> SEQ ID NO 81
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Arg Arg Val Arg His Ile Ala Gln Gly Leu Arg Arg Ala Gly Asp
1               5                   10                  15

Gln Leu Asp Lys Tyr Gly
            20

<210> SEQ ID NO 82
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Arg Arg Val Val Gln Ile Ala Ala Gly Leu Arg Arg Ala Gly Asp
1               5                   10                  15

Gln Leu Glu Lys Tyr Gly
            20

<210> SEQ ID NO 83
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Gln Arg Val Val Gln Ile Ala Gln Gly Leu Arg Arg Ala Gly Asp
1               5                   10                  15

Gln Leu Glu Lys Tyr Gly
            20

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Arg Arg Val Val Gln Ile Ala Gln Gly Leu Arg Arg Ala Gly Asp
1               5                   10                  15

Gln Leu Glu Lys Gln Gly
            20

```
<210> SEQ ID NO 85
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ser Glu Leu Glu Val Val Gln Glu Leu Val Arg Ile Gly Asp Ile
1               5                   10                  15

Val Val Ala Tyr Phe Glu Arg
            20

<210> SEQ ID NO 86
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ser Gln Tyr Glu Val Ile Gln Glu Leu Ile Arg Ile Gly Asp Ile
1               5                   10                  15

Val Leu Ala Tyr Phe Glu Arg
            20

<210> SEQ ID NO 87
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Val Val Leu Ser Val Ala Glu Thr Leu Arg Glu Leu Ala Asp Arg
1               5                   10                  15

Leu Tyr Glu Glu Ile Asn Thr
            20

<210> SEQ ID NO 88
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Arg Val Val His Ile Ala Ala Gly Leu Arg Arg Thr Gly Asp Gln
1               5                   10                  15

Leu Glu Ala Tyr Gly
            20

<210> SEQ ID NO 89
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Arg Val Val Gln Ile Ala Ala Gly Leu Arg Arg Ala Gly Asp Gln
```

```
Leu Glu Lys Tyr Gly
            20

<210> SEQ ID NO 90
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ser Tyr Val Asp Lys Ile Ala Asp Val Met Arg Glu Val Ala Glu Lys
1               5                   10                  15

Ile Asn Ser Asp Leu Thr
            20

<210> SEQ ID NO 91
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Leu Leu Glu Lys Leu Ala Glu Tyr Leu Arg Gln Met Ala Asp Glu
1               5                   10                  15

Ile Asn Lys Lys Tyr Val Lys
            20

<210> SEQ ID NO 92
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Arg Ile Ile Trp Ile Ala Ala Glu Leu Arg Arg Ala Ala Asp Glu
1               5                   10                  15

Leu Asp Lys Gln Ile Glu Arg
            20

<210> SEQ ID NO 93
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Arg Ile Ile Trp Ile Ala Ala Glu Leu Arg Arg Ala Ala Asp Gln
1               5                   10                  15

Leu Asp Ala Gln Ile Glu Arg
            20

<210> SEQ ID NO 94
<211> LENGTH: 23
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 94

Arg Trp Ile Asp Gln Ile Ala Gln Phe Leu Arg Arg Ile Gly Asp His
1               5                  10                  15

Ile Glu Lys Tyr Ile Glu Arg
            20

<210> SEQ ID NO 95
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Arg Val Asp Glu Ile Ala Gln Ile Leu Arg Arg Ile Gly Asp Asn
1               5                  10                  15

Val Thr Thr Tyr Ile Glu Arg
            20

<210> SEQ ID NO 96
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Trp Leu Arg Trp Val Ile Ala Glu Leu Ile Arg Ile Ala Asp Glu
1               5                  10                  15

Phe His Ala Gln Tyr Glu Arg
            20

<210> SEQ ID NO 97
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Trp Leu Arg Asp Val Val Ala Glu Leu Ala Arg Ile Ala Asp Glu
1               5                  10                  15

Phe His Ala Gln Tyr Glu Arg
            20

<210> SEQ ID NO 98
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Gln Trp Ala Arg Glu Ile Gly Ala Gln Leu Arg Arg Met Ala Asp
1               5                  10                  15

Asp Leu Asn Ala Gln Tyr Glu Arg Arg Arg
            20                  25
```

<210> SEQ ID NO 99
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Met Arg Pro Glu Ile Trp Ile Ala Gln Glu Leu Arg Arg Ile Gly Asp
1               5                   10                  15

Glu Phe Asn Ala Tyr Tyr Ala Arg Arg Val
            20                  25

<210> SEQ ID NO 100
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Ala Glu Leu Glu Val Glu Cys Ala Thr Gln Leu Arg Arg Phe Gly Asp
1               5                   10                  15

Lys Leu Asn Phe Arg Gln Lys Leu Leu Asn
            20                  25

<210> SEQ ID NO 101
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Leu Trp Ala Ala Gln Arg Tyr Gly Arg Glu Leu Arg Arg Met Ser Asp
1               5                   10                  15

Glu Phe Val Asp Ser Phe Lys Lys Gly Leu
            20                  25

<210> SEQ ID NO 102
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Ser Ser Thr Met Gly Gln Val Gly Arg Gln Leu Ala Ile Ile Gly Asp
1               5                   10                  15

Asp Ile Asn Arg Arg Tyr Asp Ser Glu Phe
            20                  25

<210> SEQ ID NO 103
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

```
Asp Ala Ser Thr Lys Lys Leu Ser Glu Cys Leu Lys Arg Ile Gly Asp
1               5                   10                  15

Glu Leu Asp Ser Asn Met Glu Leu Gln Arg
            20                  25

<210> SEQ ID NO 104
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ser Ala Ala Gln Leu Thr Ala Ala Arg Leu Lys Ala Leu Gly Asp
1               5                   10                  15

Glu Leu His Gln Arg Thr Met Trp Arg Arg
            20                  25

<210> SEQ ID NO 105
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

His Gln Ala Glu Val Gln Ile Ala Arg Lys Leu Gln Cys Ile Ala Asp
1               5                   10                  15

Gln Phe His Arg Leu His Val Gln Gln His
            20                  25

<210> SEQ ID NO 106
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Met Glu Gly Ser Asp Ala Leu Ala Leu Arg Leu Ala Cys Ile Gly Asp
1               5                   10                  15

Glu Met Asp Val Ser Leu Arg Ala Pro Arg
            20                  25

<210> SEQ ID NO 107
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Glu Asp Ile Ile Arg Asn Ile Ala Arg His Leu Ala Gln Val Gly Asp
1               5                   10                  15

Ser Met Asp Arg Ser Ile Pro Pro Gly Leu
            20                  25

<210> SEQ ID NO 108
<211> LENGTH: 26
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 108

Gly Val Met Thr Gln Glu Val Gly Gln Leu Leu Gln Asp Met Gly Asp
1               5                   10                  15

Asp Val Tyr Gln Gln Tyr Arg Ser Leu Thr
            20                  25

<210> SEQ ID NO 109
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Gly Thr Met Glu Asn Leu Ser Arg Arg Leu Lys Val Thr Gly Asp
1               5                   10                  15

Leu Phe Asp Ile Met Ser Gly Gln Thr Asp
            20                  25

<210> SEQ ID NO 110
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Pro Gly Arg Leu Ala Glu Val Cys Ala Val Leu Leu Arg Leu Gly Asp
1               5                   10                  15

Glu Leu Glu Met Ile Arg Pro Ser Val Tyr
            20                  25

<210> SEQ ID NO 111
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Trp Ala Arg Glu Ile Gly Ala Gln Leu Arg Arg Met Ala Asp Asp
1               5                   10                  15

Leu Asn Ala Gln Tyr Glu Arg
            20

<210> SEQ ID NO 112
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Trp Val Arg Glu Ile Ala Ala Gly Leu Arg Arg Ala Ala Asp Asp
1               5                   10                  15

Val Asn Ala Gln Val Glu
            20
```

<210> SEQ ID NO 113
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ser Tyr Val Asp Lys Ile Ala Asp Leu Met Lys Val Ala Glu Lys
1               5                   10                  15

Ile Asn Ser Asp Leu Thr
            20

<210> SEQ ID NO 114
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Tyr Ile Asp Lys Ile Ala Asp Leu Ile Asp Lys Val Val Glu Glu
1               5                   10                  15

Ile Asn Ser Lys Leu Glu
            20

<210> SEQ ID NO 115
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ser Leu Leu Glu Lys Leu Ala Glu Glu Leu Arg Gln Leu Ala Asp Glu
1               5                   10                  15

Leu Asn Lys Lys Phe Glu Lys
            20

<210> SEQ ID NO 116
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Leu Leu Glu Lys Leu Ala Glu Tyr Leu Arg Gln Met Ala Asp Glu
1               5                   10                  15

Ile Asn Lys Lys Tyr Val Lys
            20

<210> SEQ ID NO 117
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Ser Leu Leu Glu Lys Leu Ala Glu Glu Leu Ala Gln Leu Ala Asp Glu
1               5                   10                  15

Leu Asn Lys Lys Phe Glu Lys
            20
```

<210> SEQ ID NO 118
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Ser Leu Leu Glu Lys Leu Ala Glu Tyr Leu Ala Gln Met Gly Asp Glu
1               5                   10                  15

Ile Asn Lys Lys Tyr Val Lys
            20
```

<210> SEQ ID NO 119
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Gly Arg Pro Glu Ile Trp Ile Ala Gln Glu Leu Arg Arg Ile Gly Asp
1               5                   10                  15

Glu Phe Asn Ala Tyr Tyr Ala
            20
```

<210> SEQ ID NO 120
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Ala Pro Lys Glu Lys Glu Val Ala Glu Thr Leu Arg Lys Ile Gly Glu
1               5                   10                  15

Glu Ile Asn Glu Ala Leu Lys
            20
```

<210> SEQ ID NO 121
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

```
Ala Pro Tyr Leu Glu Gln Val Ala Arg Thr Leu Arg Lys Ile Gly Glu
1               5                   10                  15

Glu Ile Asn Glu Ala Leu Arg
            20
```

<210> SEQ ID NO 122
<211> LENGTH: 23
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 122

Ala Pro Lys Glu Lys Glu Val Ala Arg Thr Leu Ile Lys Ile Gly Glu
1               5                   10                  15

Glu Ile Asn Glu Ala Leu Lys
            20

<210> SEQ ID NO 123
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Pro Tyr Leu Glu Gln Val Ala Arg Thr Leu Leu His Ile Gly Met
1               5                   10                  15

Glu Ile Asn Glu Ala Leu Arg
            20

<210> SEQ ID NO 124
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (17)..(18)
<223> OTHER INFORMATION: Norleucine

<400> SEQUENCE: 124

Glu Asp Ile Ile Arg Asn Ile Ala Arg His Leu Ala Xaa Val Gly Asp
1               5                   10                  15

Xaa Xaa Asp Arg Ser Ile
            20

<210> SEQ ID NO 125
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asp Lys Thr Leu Glu Glu Ile Ala Arg Glu Leu Ala Lys Leu Ala Glu
1               5                   10                  15

Glu Ile Asp Lys Glu Ile
            20

<210> SEQ ID NO 126
<211> LENGTH: 22
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 126

Asp Lys Thr Leu Glu Glu Ile Ala Arg Trp Leu Ala Arg Leu Ala Leu
1               5                   10                  15

Glu Ile Asp Lys Glu Ile
            20

<210> SEQ ID NO 127
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asp Lys Thr Leu Glu Glu Ile Ala Arg Glu Leu Leu Lys Leu Ala Leu
1               5                   10                  15

Glu Ile Asp Lys Glu Ile
            20

<210> SEQ ID NO 128
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gln Trp Val Arg Glu Ile Ala Ala Gly Leu Arg Arg Ala Ala Asp Asp
1               5                   10                  15

Val Asn Ala Gln Val Glu Arg
            20

<210> SEQ ID NO 129
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Asp Ile Glu Gln Glu Ile Ala Glu Ala Leu Lys Glu Val Ala Asp Glu
1               5                   10                  15

Leu Ser Lys Ala Ile Glu Asp
            20

<210> SEQ ID NO 130
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Arg Pro Glu Ile Trp Ile Ala Gln Glu Leu Arg Arg Ile Gly Asp Glu
1               5                   10                  15

Phe Asn Ala Tyr Tyr Ala Arg
            20

```
<210> SEQ ID NO 131
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Gln Trp Ala Arg Glu Ile Gly Ala Gln Leu Arg Arg Met Ala Asp
1               5                   10                  15

Asp Leu Asn Ala
            20

<210> SEQ ID NO 132
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Glu Gln Trp Ala Arg Glu Ile Gly Ala Gln Ala Arg Arg Met Ala Ala
1               5                   10                  15

Asp Leu Asn Ala
            20

<210> SEQ ID NO 133
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Arg Pro Glu Ile Trp Met Thr Gln Gly Leu Arg Arg Leu Gly Asp Glu
1               5                   10                  15

Ile Asn Ala Tyr Tyr Ala Arg
            20

<210> SEQ ID NO 134
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: 2-aminoisobutyric acid

<400> SEQUENCE: 134

Ile Trp Xaa Xaa Gln Gly Leu Arg Arg Leu Gly Asp Glu Ile Asn Ala
1               5                   10                  15

Tyr Tyr Ala Arg Arg
            20

<210> SEQ ID NO 135
<211> LENGTH: 23
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 135

Gln Trp Val Arg Glu Ile Ala Ala Gly Leu Arg Leu Ala Ala Asp Asn
1               5                   10                  15

Val Asn Ala Gln Leu Glu Arg
            20

<210> SEQ ID NO 136
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Thr Leu Ile Trp Tyr Gly Ala Ser Leu Arg Arg Tyr Ala Asp Glu
1               5                   10                  15

Phe Ala Lys Gln Arg Glu Arg
            20

<210> SEQ ID NO 137
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Pro Leu Ile Trp Phe Gly Ala Gln Leu Arg Arg Gly Ala Asp Glu
1               5                   10                  15

Phe Ala Ala Gln Arg Glu Arg
            20
```

PEPTIDES SELECTIVE FOR BCL-2 FAMILY PROTEINS

CROSS-REFERENCE TO RELATED APPLICATIONS

This application claims the benefit of U.S. Provisional Application Ser. No. 62/732,518, filed on Sep. 17, 2018. The entire contents of the foregoing are incorporated herein by reference.

FEDERALLY SPONSORED RESEARCH OR DEVELOPMENT

This invention was made with Government support under Grant Nos. R01 GM110048 and R01-GM096466 awarded by the National Institutes of Health. The Government has 10 certain rights in the invention.

SEQUENCE LISTING

The instant application contains a Sequence Listing which has been submitted electronically in ASCII format and is hereby incorporated by reference in its entirety.

TECHNICAL FIELD

This disclosure relates to peptides that bind Bcl-2 family proteins, specifically Bfl-1, Bcl-xL, and Mcl-1, and methods of using such peptides in the treatment and diagnosis of cancer.

BACKGROUND

Peptides of the B-cell lymphoma 2 (Bcl-2) family are regulators of apoptosis that have emerged as key therapeutic targets in cancer biology. Overexpression of human anti-apoptotic proteins Bcl-2, Mcl-1, Bfl-1, Bcl-xL, and Bcl-w contributes to oncogenesis and resistance to chemotherapy (10, 11). These five proteins share the same fold and are 18-53% identical in sequence (12). Many native partners of Bcl-2, Mcl-1, Bfl-1, Bcl-xL, and Bcl-w contain a ~23-residue Bcl-2 homology 3 (BH3) motif that is disordered in isolation but forms a helix upon binding. Small molecules or peptides that block binding to this helix can inhibit anti-apoptotic function and have shown promise in pre-clinical and clinical studies (13-17).

Members of the Bcl-2 family—including Bfl-1, Bcl-xL, Bcl-2, Bcl-w, Mcl-1, and Bcl-b—block apoptosis by interfering with the homo-oligomerization of Bak and Bax. The anti-apoptotic proteins either bind directly to Bax or Bak or bind related pro-apoptotic activator proteins (e.g. Bim, Bid, and Puma), preventing activation of Bax and Bak. Other proteins having BH3-domains, called sensitizers, antagonize anti-apoptotic function by binding competitively with Bax/Bak and activators.

Overexpression of anti-apoptotic proteins has been observed in several cancers and has been shown to promote resistance to chemotherapeutics (Wenzel, S. S., Grau, M., Mavis, C., Hailfinger, S., Wolf, A., Madle, H. Lenz, G. MCL1 is deregulated in subgroups of diffuse large B-cell lymphoma. Leukemia, 27(6), 1381-1390 (2013); Choi, S., Chen, Z., Tang, L. H., Fang, Y., Shin, S. J., Panarelli, N. C., Du, Y. C. N. Bcl-xL promotes metastasis independent of its anti-apoptotic activity. Nature Communications, 7 (2016); Scherr, A. L., Gdynia, G., Salou, M., Radhakrishnan, P., Duglova, K., Heller, A., Koehler, B. C. Bcl-xL is an oncogenic driver in colorectal cancer. Cell Death & Disease, 7(8), e2342 (2016); Yecies, D., Carlson, N. E., Deng, J., & Letai, A. Acquired resistance to ABT-73 in lymphoma cells that upregulate of Mcl1 and BFL-1. Blood, 115(16), 3304-3314 (2010)). Targeting the downregulation of anti-apoptotic proteins—either by decreasing mRNA levels, protein levels, or protein function—is a promising therapeutic strategy for killing cancer cells alone or in combination with existing chemotherapeutic agents (Olsson, A. et al. Upregulation of bfl-1 is a potential mechanism of chemoresistance in B-cell chronic lymphocytic leukaemia. Br. J. Cancer 97, 769-77 (2007); Senft, D. et al. Selective induction of cell death in melanoma cell lines through targeting of Mcl-1 and A1. PLoS One 7, e30821 (2012); Bose, P., & Grant, S. Mcl-1 as a therapeutic target in acute myelogenous leukemia (AML). Leukemia Research Reports, 2(1), 12-14 (2013); Opferman, J. T. Attacking cancer's Achilles heel: antagonism of anti-apoptotic BCL-2 family members. FEBS J. (2015))

SUMMARY

Described herein is a compound comprising a peptide comprising or consisting of the amino acid sequence:
A1 B1 C1 D1 E1 F1 E1 G1 B1 H1 A2 B2 C2 E1 A1 D2 D1 E1 E2 F2B1 E1 (SEQ ID NO: 1) or comprising a peptide comprising the amino acid sequence
A1 B1 C1 D1 E1 F1 G2 H2 B1 E1 A2C2C2G2A1 D2 D1 G2 H1 F2B1 E1 (SEQ ID NO: 2) or comprising a peptide comprising the amino acid sequence
A1 B1 C1 D1 A3 FI B3 C3 B1 E1 A2 D3 C2 E2 A1 D2 D1 E1 E3 F2 B1 E2 (SEQ ID NO: 3) or comprising a peptide comprising the amino acid sequence
A1 B1 F3 G2 G3 H3 A4 H2 B1 G3 A2 D3 C2 B4 A1 D2 D1 A2 E4 F2 B1 D4 (SEQ ID NO: 4) or comprising a peptide comprising the amino acid sequence
A1 B1 C1 D1 G2 E4 E1 A1 B1 F4 A2 D3 C2 G4 H2 D2 H4 A5 B5 F2 B1 C5 (SEQ ID NO: 5) or comprising a peptide comprising the amino acid sequence A1 B1 D5 D1 E1 D2 E2 C3 B1 E5 A2 F5 C2 A2 A1 D2 D1 G5 H5 A6 B1 A5 (SEQ ID NO: 6), wherein A1 is G or a conservative substitution; B1 is Q or a conservative substitution; C1 is W or a conservative substitution, P or a conservative substitution, G or a conservative substitution, A or a conservative substitution, R or a conservative substitution, T or a conservative substitution; D1 is M or a conservative substitution, L or a conservative substitution, E or a conservative substitution, I or a conservative substitution; E1 is L or a conservative substitution, Y or a conservative substitution, F or a conservative substitution; F1 is E or a conservative substitution, D or a conservative substitution, H or a conservative substitution; G1 is D or a conservative substitution, V or a conservative substitution, G or a conservative substitution, A or a conservative substitution, S or a conservative substitution, I or a conservative substitution; H1 is L or a conservative substitution, D or a conservative substitution, Q or a conservative substitution, E or a conservative substitution; A2 is L or a conservative substitution; B2 is T or a conservative substitution, V or a conservative substitution, G or a conservative substitution, A or a conservative substitution, R or a conservative substitution, I or a conservative substitution; C2 is R or a conservative substitution; D2 is D or a conservative substitution; E2 is L or a conservative substitution, V or a conservative substitution, A or a conservative substitution, I or a conservative substitution; F2 is T or a conservative substitution, K or a conservative substitution, E or a conservative substitution, A or a conservative substitution; G2 is V or a conservative substitution, I or a conservative substitution; H2 is A or a conservative substitution; A3 is R or a conservative substitution, V or a conservative substitution, Y or a conservative substitution, D or a conservative substitution, I or a conservative substitution; B3 is T or a conservative substitution, L or a conservative substitution, I or a conservative substitution, F or a conservative substitution; C3 is V or a conservative substitution, G or a conservative substitution, A or a conservative substitution, S or a conservative substitution; D3 is R or a conservative substitution, A or a conservative substitution, K or a conservative substitution; E3 is H or a conservative substitution, D or a conservative substitution, Q or a conservative substitution, V or a conservative substitution, N or a conservative substitution, E or a conservative substitution; F3 is R or a conservative substitution, P or a conservative substitution, W or a conservative substitution, A or a conservative substitution; G3 is D or a conservative substitution, Y or a conservative substitution, F or a conservative substitution, I or a conservative substitution; H3 is Q or a conservative substitution, H or a conservative substitution, E or a conservative substitution; A4 is I or a conservative substitution; B4 is T or a conservative substitution, W or a conservative substitution, A or a conservative substitution, S or a conservative substitution; C4 is N or a conservative substitution, E or a conservative substitution, D or a conservative substitution, T or a conservative substitution; D4 is L or a conservative substitution, A or a conservative substitution, Y or a conservative substitution, G or a conservative substitution, I or a conservative substitution; E4 is D or a conservative substitution, W or a conservative substitution; F4 is Q or a conservative substitution, E or a conservative substitution, S or a conservative substitution; G4 is M or a conservative substitution, Y or a conservative substitution, F or a conservative substitution, V or a conservative substitution, G or a conservative substitution, A or a conservative substitution; H4 is Q or a conservative substitution, M or a conservative substitution, D or a conservative substitution, V or a conservative substitution, E or a conservative substitution; A5 is F or a conservative substitution; B5 is Q or a conservative substitution, N or a conservative substitution, H or a conservative substitution, A or a conservative substitution; C5 is R or a conservative substitution, L or a conservative substitution, Y or a conservative substitution; D5 is R or a conservative substitution, T or a conservative substitution, G or a conservative substitution, A or a conservative substitution, S or a conservative substitution; E5 is L or a conservative substitution, D or a conservative substitution, Y or a conservative substitution, V or a conservative substitution, E or a conservative substitution, I or a conservative substitution; F5 is A or a conservative substitution, V or a conservative substitution, G or a conservative substitution, I or a conservative substitution; G5 is T or a conservative substitution, L or a conservative substitution, V or a conservative substitution, I or a conservative substitution; H5 is L or a conservative substitution, D or a conservative substitution, Q or a conservative substitution, N or a conservative substitution, V or a conservative substitution, A or a conservative substitution, T or a conservative substitution, E or a conservative substitution, I or a conservative substitution; A6 is T or a conservative substitution, E or a conservative substitution, A or a conservative substitution.

In some embodiments: A1 is G; B1 is Q; C1 is W, P, G, A, R, or T; D1 is M, L, E, or I; E1 is L, Y, or F; F1 is E, D, or H; G1 is D, V, G, A, S, or I; H1 is L, D, Q, or E; A2 is L; B2 is T, V, G, A, R, or I; C2 is R; D2 is D; E2 is L, V, A, or I; F2 is T, K, E, or A; G2 is V or I; H2 is A; A3 is R, V, Y, D, or I; B3 is T, L, I, or F; C3 is V, G, A, or S; D3 is R, A, or K; E3 is H, D, Q, V, N, or E; F3 is R, P, W, or A; G3 is D, Y, F, or I; H3 is Q, H, or E; A4 is I; B4 is T, W, A, or S; C4 is N, E, D, or T; D4 is L, A, Y, G, or I; E4 is D or W; F4 is Q, E, or S; G4 is M, Y, F, V, G, or A; H4 is Q, M, D, V, or E; A5 is F; B5 is Q, N, H, or A; C5 is R, L, or Y; D5 is R, T, G, A, or S; E5 is L, D, Y, V, E, or I; F5 is A, V, G, or I; G5 is T, L, V, or I; H5 is L, D, Q, N, V, A, T, E, or I; A6 is T, E, or A.

In some embodiments, a compound comprises a peptide comprising or consisting of the amino acid sequence selected from the group consisting of:

```
                                        (SEQ ID NO: 85)
RSELEVVQELVRIGDIVVAYFER;

(SEQ ID NO: 86)
RSQYEVIQELIRIGDIVLAYFER;

(SEQ ID NO: 87)
DVVLSVAETLRELADRLYEEINT;

(SEQ ID NO: 88)
QRVVHIAAGLRRTGDQLEAYG;

(SEQ ID NO: 89)
RRVVQIAAGLRRAGDQLEKYG;

(SEQ ID NO: 90)
SYVDKIADVMREVAEKINSDLT;

(SEQ ID NO: 91)
SLLEKLAEYLRQMADEINKKYVK;

(SEQ ID NO: 92)
QRIIWIAAELRRAADELDKQIER;

(SEQ ID NO: 93)
QRIIWIAAELRRAADQLDAQIER;

(SEQ ID NO: 94)
RWIDQIAQFLRRIGDHIEKYIER;

(SEQ ID NO: 95)
RRVDEIAQILRRIGDNVTTYIER;

(SEQ ID NO: 96)
QWLRWVIAELIRIADEFHAQYER;
and (SEQ ID NO: 97)
QWLRDVVAELARIADEFHAQYER.
```

In some embodiments, the compound described herein comprises a polypeptide comprising or of consisting of sequence selected from the group consisting of

```
                                        (SEQ ID NO: 85)
RSELEVVQELVRIGDIVVAYFER;

(SEQ ID NO: 86)
RSQYEVIQELIRIGDIVLAYFER;
and (SEQ ID NO: 87)
DVVLSVAETLRELADRLYEEINT.
```

In some embodiments, the compound described herein comprises a polypeptide comprising or of consisting of sequence selected from the group consisting of

QRVVHIAAGLRRTGDQLEAYG; (SEQ ID NO: 88)

RRVVQIAAGLRRAGDQLEKYG; (SEQ ID NO: 89)

SYVDKIADVMREVAEKINSDLT; (SEQ ID NO: 90)
and

SLLEKLAEYLRQMADEINKKYVK. (SEQ ID NO: 91)

In some embodiments, the compound described herein comprises a polypeptide comprising or of consisting of sequence selected from the group consisting of QRIIWIAAELRRAADELDKQIER; (SEQ ID NO: 92)
and

QRIIWIAAELRRAADQLDAQIER. (SEQ ID NO: 93)

In some embodiments, the compound described herein comprises a polypeptide comprising or of consisting of sequence selected from the group consisting of RWIDQIAQFLRRIGDHIEKYIER; (SEQ ID NO: 94)
and

RRVDEIAQILRRIGDNVTTYIER. (SEQ ID NO: 95)

In some embodiments, the compound described herein comprises a polypeptide comprising or of consisting of sequence selected from the group consisting of QWLRWVIAELIRIADEFHAQYER; (SEQ ID NO: 96)
and

QWLRDVVAELARIADEFHAQYER. (SEQ ID NO: 97)

Also described is a pharmaceutical composition comprising a compound described herein. Also described is a method for treating cancer comprising administering a compound described herein to a patient in need thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

(a) Crystal structure at 1.48 Å of the Bfl-1-specific peptide srt.F10 (cyan cartoon) bound to Bfl-1 (gray surface), (b) Comparison of the binding modes of srt.F10 (cyan ribbon) and srt.F4 (1.48 Å, magenta ribbon) with a natural ligand, Bim BH3 (green, ribbon; 2VM6(44)). The region shown in panel b corresponds to the boxed region in panel a. (c) Contributions of each residue of srt.F10 to binding Bfl-1, Mcl-1 and Bcl-xL, as predicted by the polynomial model. For each position, all model weights that included the position were summed. Blue indicates a favorable net contribution to binding; red a net unfavorable contribution. All figures made using Pymol.

Figure 5:
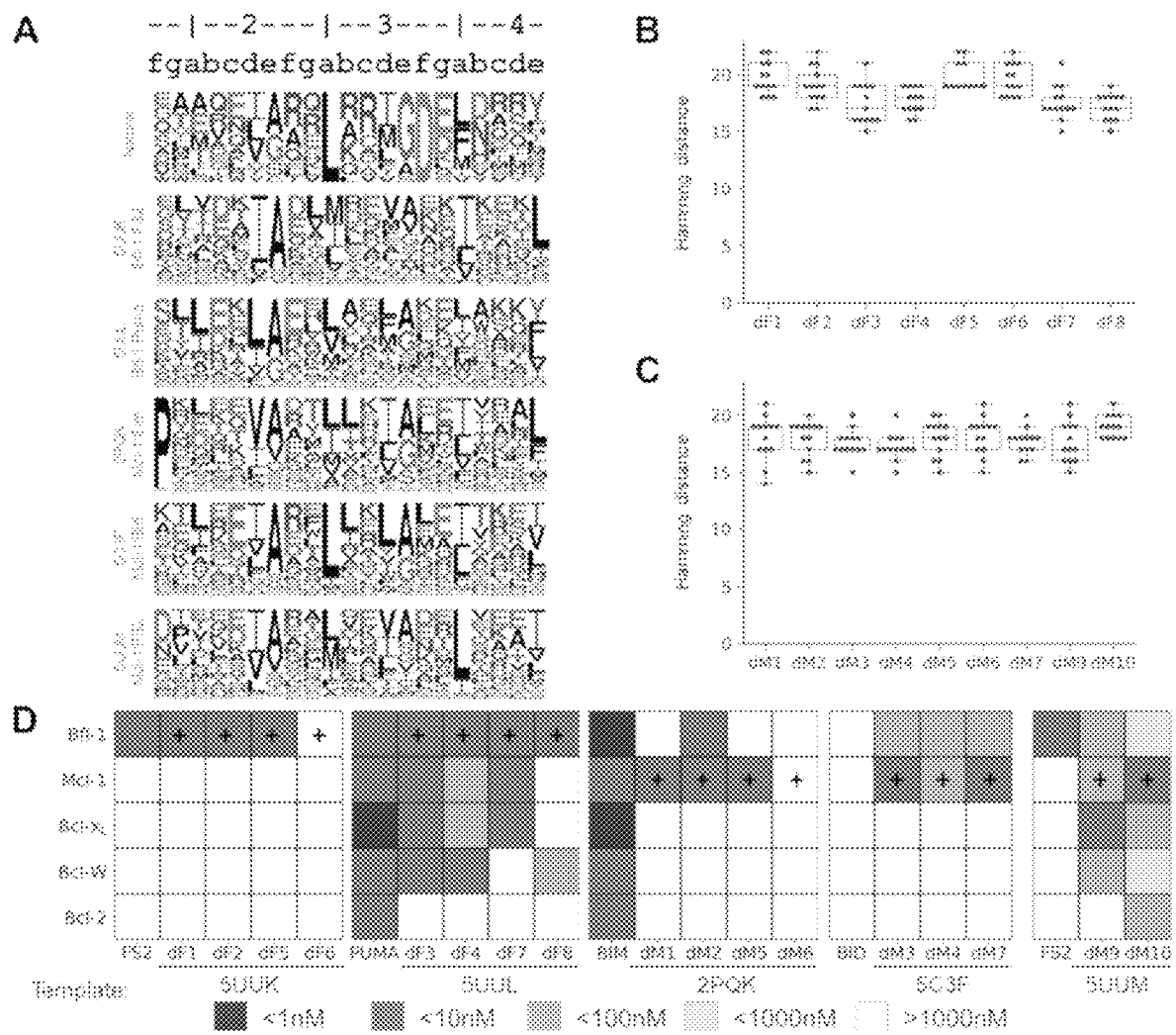

FIG. 5: dTERMen design of peptides to bind Mcl-1 and Bfl-1

(a) Sequence logos for peptides designed using dTERMen on each of the design templates 5UUK, 5UUL, 2PQK, 5C3F, and 5UUM. Heptad notation for the peptide sequences is shown above the logos. A list of the 13 BH3 motif sequences used to generate the "Natural" logo is Table Y1. The sequences of the Bfl-1 designs (b) and the Mcl-1 designs (c) were compared to known natural BH3 motifs in Table Y1. The designed sequences were cloned into yeast for cell surface display and binding to each protein was measured using FACS, (d) Shown here is the median fluorescence binding signal of each peptide in the presence of 1, 10, and 100 nM of the target proteins Bfl-1 or Mcl-1.

Figure 6:
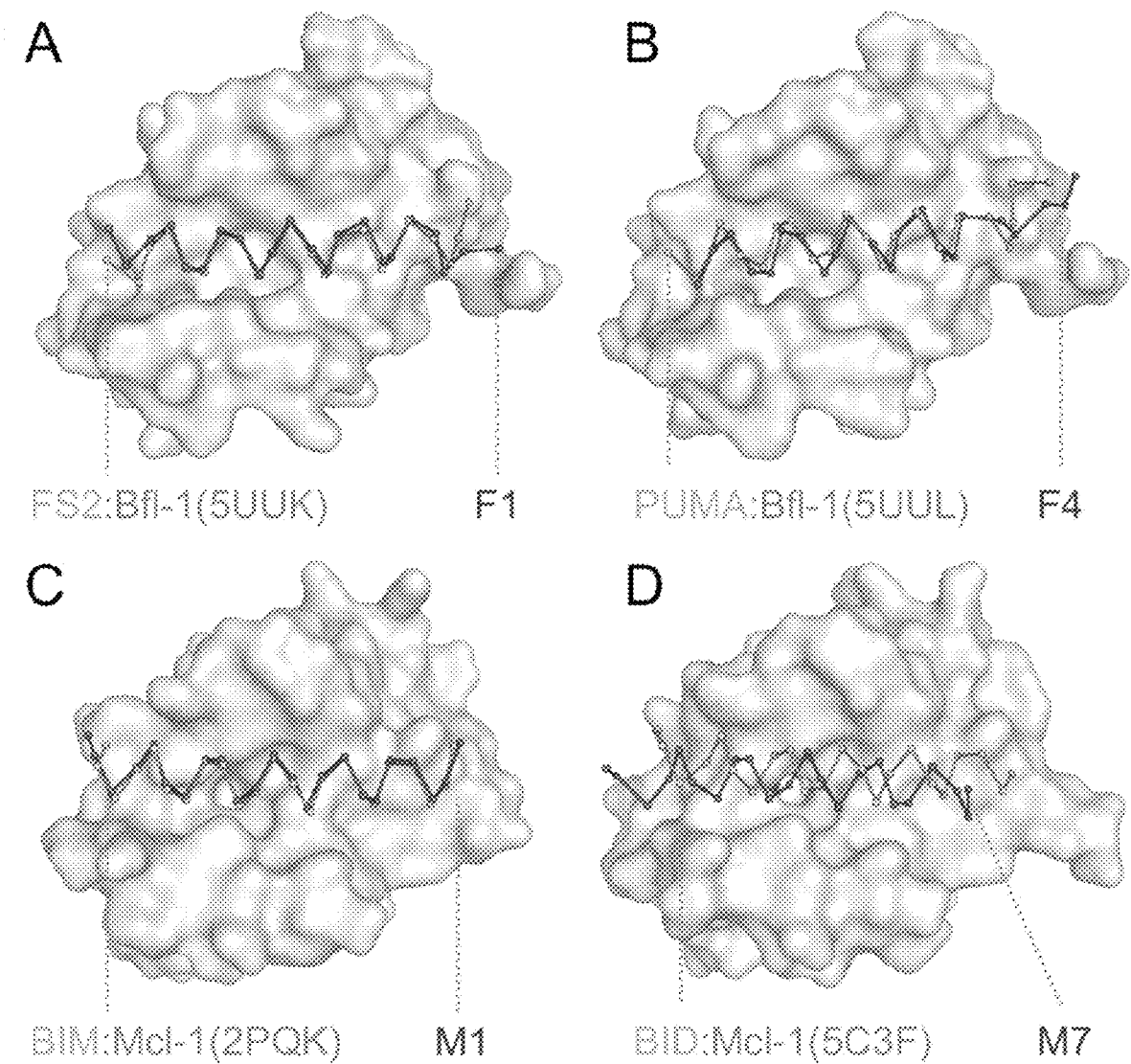

FIG. 6: Comparison of the structures of designed complexes and their templates

X-ray crystal structures of (a) dF1 bound to Bfl-1, (b) dF4 bound to Bfl-1, (c) dM1 bound to Mcl-1, and (d) dM7 bound to Mcl-1 (all with the peptide in purple) are compared to the template structures on which they were designed (green ribbon and gray surface). The N-terminal end of each peptides lies to the left in the figure.

Figure 7:
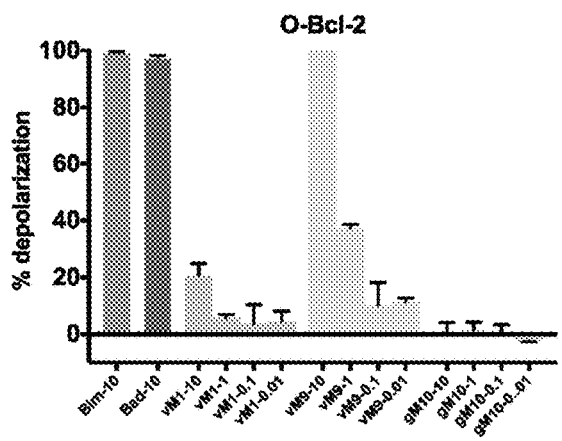
Figure 7:
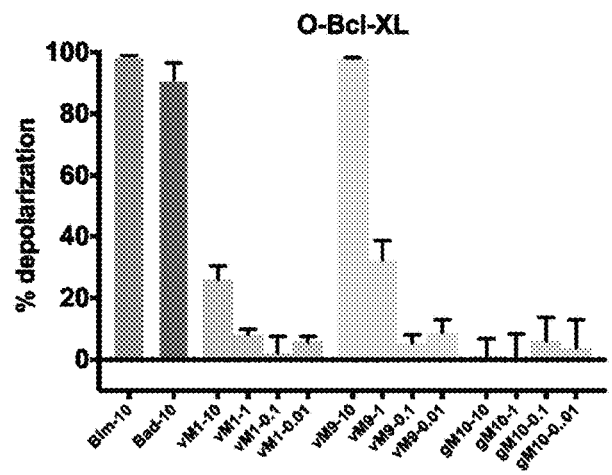
Figure 7:
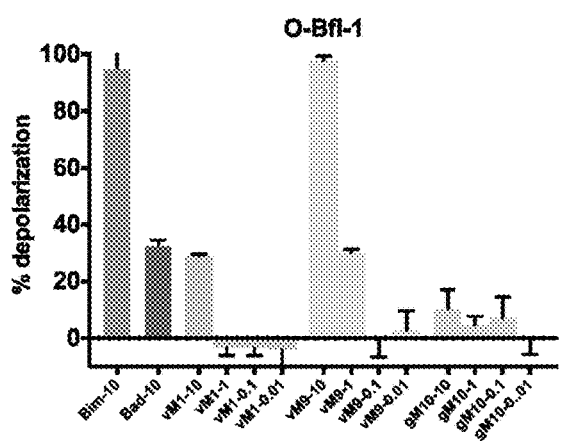
Figure 7:
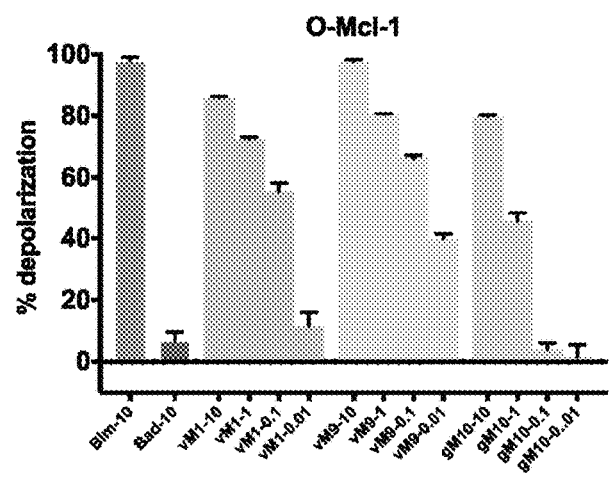
Figure 7:
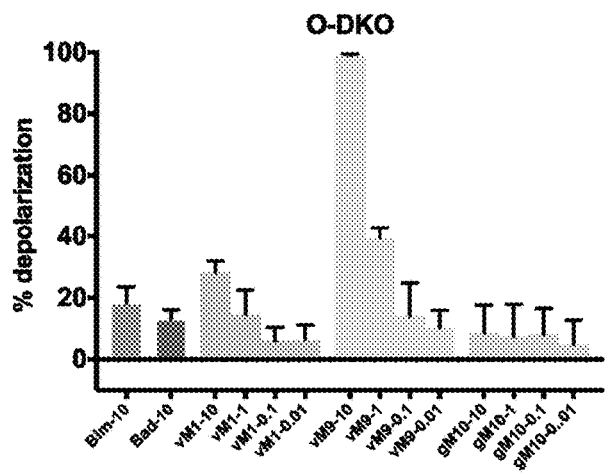

FIG. 7: Designed Mcl-1 inhibitors

Bar charts showing depolarization of mitochondria induced by peptides designed by SORTCERY and dTERMen in BCR-ABL-expressing B-lineage acute lymphoblastic leukemia (B-ALL) cell lines engineered to depend on overexpression of (a) Bcl-2; (b) Bcl-xL; (c) Bfl-1; (d) Mcl-1; and (e) in B-ALL cells in which Mcl-1-deletion is rescued by loss of both BAX and BAK (i.e., DKO). SORTCERY, v; dTERMen, g; peptide concentration 0.1 µM, 0.1; and 10 µM, 10.

Figure 8:
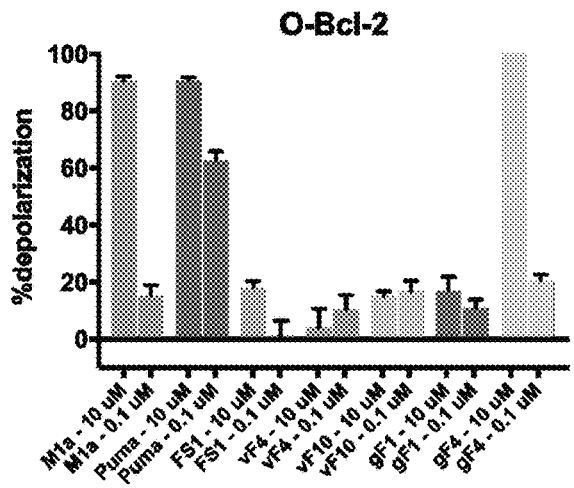
Figure 8:
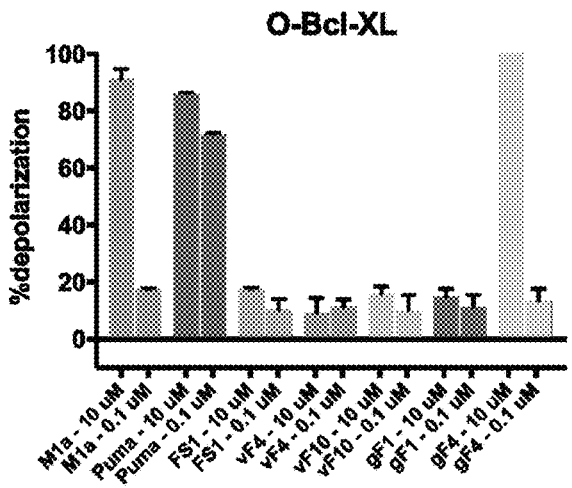
Figure 8:
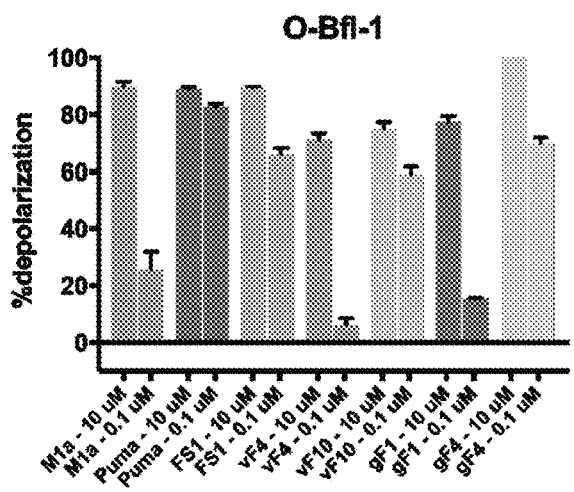
Figure 8:
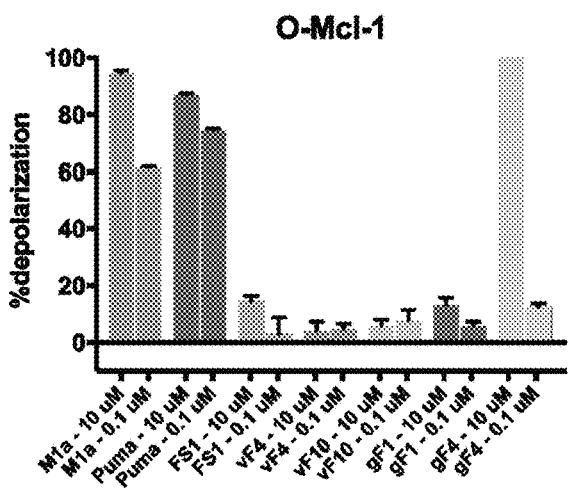
Figure 8:
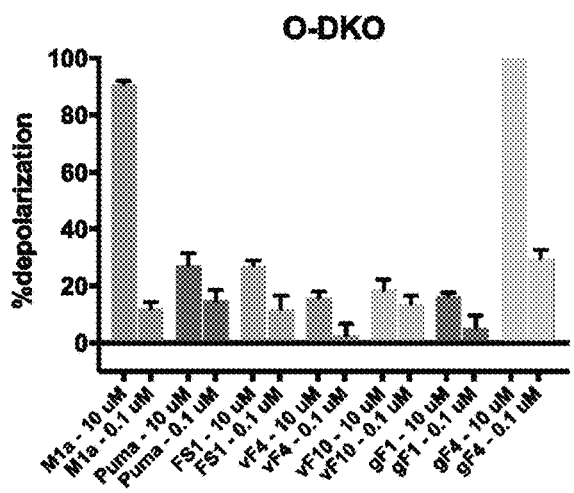

FIG. 8: Designed Bfl-1 inhibitors

Bar charts showing depolarization of mitochondria induced by peptides designed by SORTCERY (v) and dTERMen (g) in Opferman Bcl-2 paralog-overexpressing cell lines overexpressing (a) Bcl-2; (b) Bcl-xL; (c) Bfl-1; (d) Mcl-1; and (e) in B-ALL cells in which Mcl-1-deletion is rescued by loss of both BAX and BAK (i.e., DKO). Peptide concentration 0.01 µM (0.01); 0.1 µM (0.1); 1 µM (1); and 10 µM (10).

Figure 9:
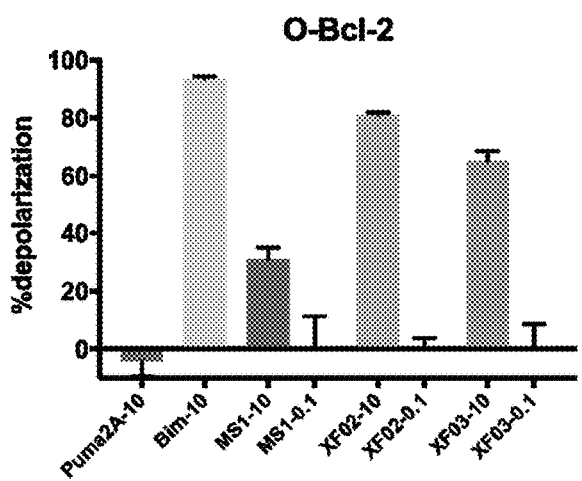
Figure 9:
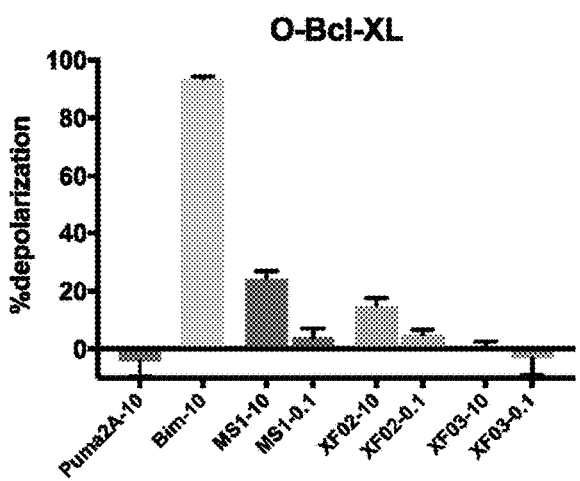
Figure 9:
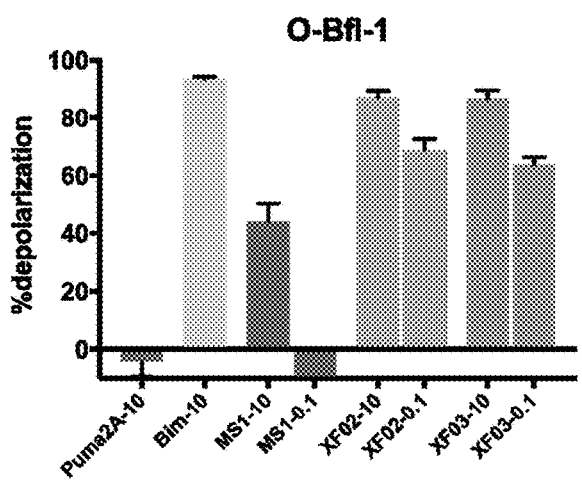
Figure 9:
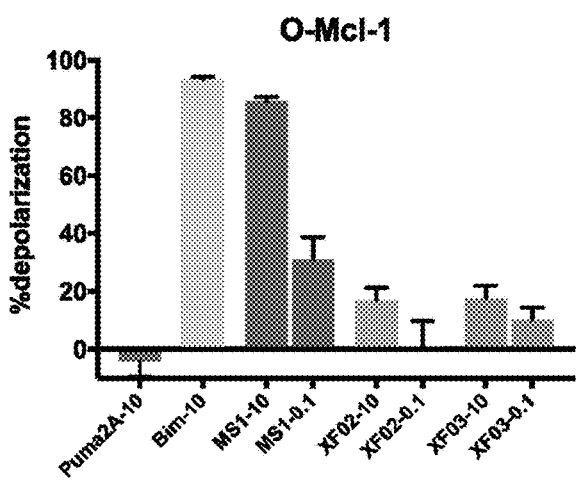

FIG. 9: Designed dual-specific Bcl-xL and Bfl-1 inhibitors

Bar charts showing depolarization of mitochondria induced by dual-specific Bcl-xL and Bfl-1 peptides in Opferman Bcl-2 paralog-overexpressing cell lines overexpressing (a) Bcl-2; (b) Bcl-xL; (c) Bfl-1; and (d) Mcl-1. Peptide concentration 0.1 µM (0.1) and 10 µM (10).

Figure 10:
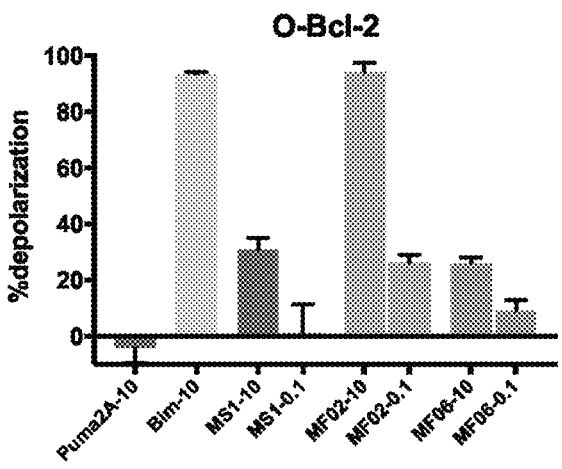
Figure 10:
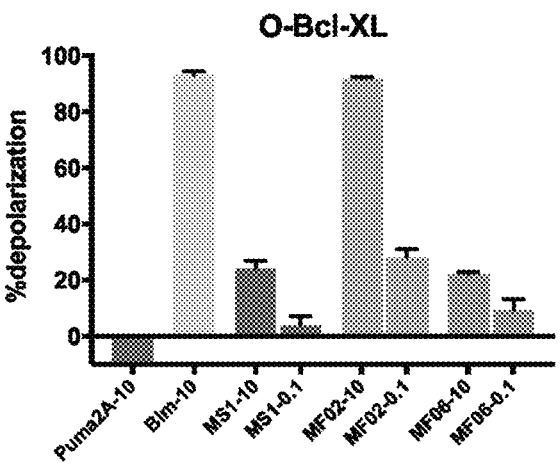
Figure 10:
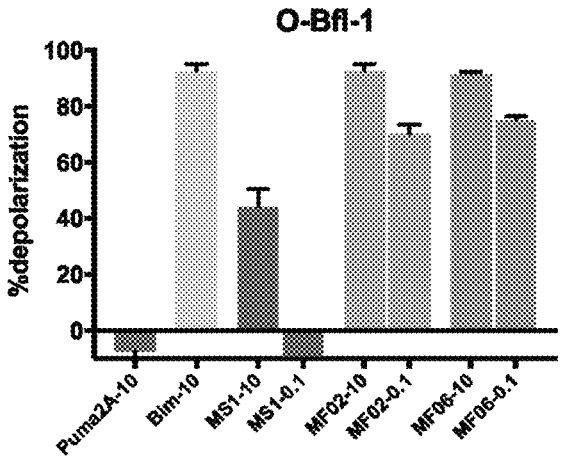
Figure 10:
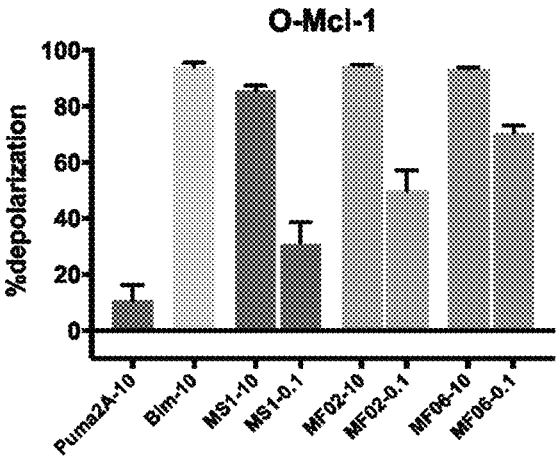

FIG. 10: Designed dual-specific Mcl-1 and Bfl-1 inhibitors

Bar charts showing depolarization of mitochondria induced by dual-specific Mcl-1 and Bfl-1 peptides in Opferman Bcl-2 paralog-overexpressing cell lines overexpressing (a) Bcl-2; (b) Bcl-xL; (c) Bfl-1; and (d) Mcl-1. Peptide concentration 0.1 µM (0.1) and 10 µM (10).

Figure 11:
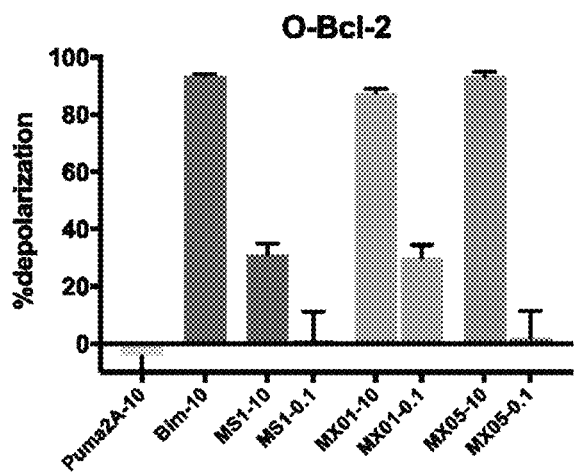
Figure 11:
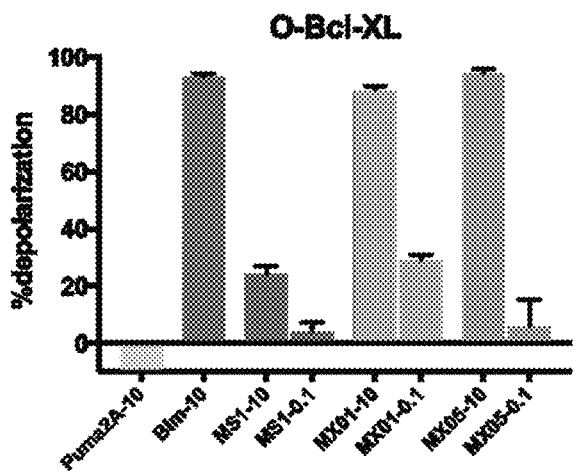
Figure 11:
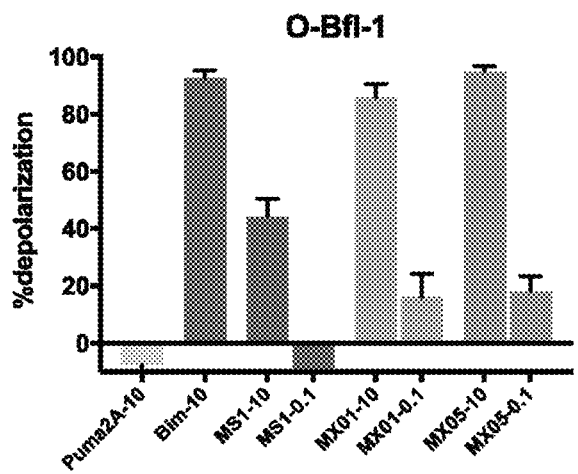
Figure 11:
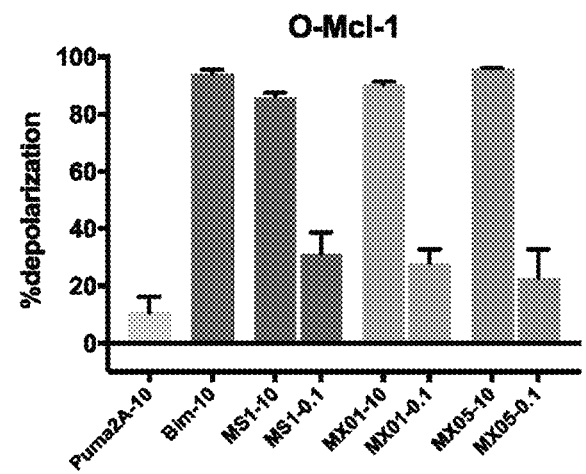

FIG. 11: Designed dual-specific Mcl-1 and Bcl-xL inhibitors

Bar charts showing depolarization of mitochondria induced by dual-specific Mcl-1 and Bcl-xL peptides in Opferman Bcl-2 paralog-overexpressing cell lines overexpressing (a) Bcl-2; (b) Bcl-xL; (c) Bfl-1; and (d) Mcl-1. Peptide concentration 0.1 µM (0.1) and 10 µM (10).

DETAILED DESCRIPTION

The present disclosure provides compounds for the selective targeting of Mcl-1, Bcl-xL, Bfl-1, both Mcl-1 and Bcl-xL, both Mcl-1 and Bfl-1, or both Bcl-xL and Bfl-1. The compounds described herein comprise a polypeptide that binds relatively tightly to the aforementioned selective target(s) and inhibits its function. The peptides described herein were designed using two different approaches, both of which yielded novel, diverse peptides that are dissimilar to known Bcl-2-binding peptides.

In the first approach, we measured thousands of protein-peptide binding affinities with a high-throughput interaction assay that is an improved version of SORTCERY and used the data to parameterize a model of the alpha-helical peptide-binding landscape for three members of the Bcl-2 family of proteins: Bcl-xL, Mcl-1, and Bfl-1. We applied optimization protocols to explore extremes in this landscape in order to discover peptides with desired interaction profiles. Computational design generated 36 peptides, all of which bound with high affinity and specificity to just one of Bcl-xL, Mcl-1, or Bfl-1, as intended. We designed additional peptides that bound selectively to two out of three of these proteins. The designed peptides were dissimilar to known Bcl-2-binding peptides, and high-resolution crystal structures confirmed that they engaged their targets as expected.

In the second approach, dTERMen, a peptide design method that employs well-defined, non-contiguous structural motifs (TERMs) from the Protein Data Bank (PDB), was used to solve for the optimal sequence to fit on the peptide chain in the template given a fixed sequence for the protein target. Specifically we chose 5 structures as design templates: two structures of Bfl-1 complexes and three structures of Mcl-1 complexes. This approach generated highly novel and diverse peptides that tightly bound their intend target anti-apoptotic, and these peptides have just 15-38% sequence identity to any known native Bcl-2 family protein ligand.

Compounds

As described herein, the compounds comprise a polypeptide. Amino acids are the building blocks of the peptides herein. The term "amino acid" refers to a molecule containing both an amino group, a carboxyl group, and a side chain. Amino acids suitable for inclusion in the peptides disclosed herein include, without limitation, natural alpha-amino acids such as D- and L-isomers of the 20 common naturally occurring alpha-amino acids found in peptides (e.g., Ala (A), Arg (R), Asn (N), Cys (C), Asp (D), Gln (Q), Glu (E), Gly (G), His (H), Ile (I), leu (L), Lys (K), Met (M), Phe (F), Pro (P), Ser (S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnnatural beta-amino acids. Amino acids used in the construction of peptides of the present invention can be prepared by organic synthesis, or obtained by other routes, such as, for example, degradation of or isolation from a natural source.

There are many known unnatural amino acids any of which may be included. Some examples of unnatural amino acids are 4 hydroxyproline, desmosine, gamma-aminobutyric acid, beta-cyanoalanine, norvaline, 4 (E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and /para-substituted phenylalanines (e.g., substituted with —C(=O)C6H5; —CF3; —CN; -halo; —NO2; CH3), disubstituted phenylalanines, substituted tyrosines (e.g., further substituted with -Q=O)C6H5; —CF3; —CN; -halo; —NO2; CH3), and statine. Additionally, amino acids can be derivatized to include amino acid residues that are hydroxylated, phosphorylated, sulfonated, acylated, and glycosylated, to name a few.

In some instances, peptides include only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, an electrophilic group, a hydroxyl group, a phosphate group, a farnesyl group, an isofarnesyl group, a fatty acid group, a linker for conjugation, functionalization, or other modification, etc.

Therefore a compound comprising a polypeptide described herein, can include a polypeptide that is modified, for example, by the addition of a chemical entity such as a carbohydrate group, an electrophilic group, a hydroxyl group, a phosphate group, a farnesyl group, an isofarnesyl group, a fatty acid group, a linker for conjugation, functionalization, or other modification, etc.

In some instances, peptides can include (e.g., comprise, consist essentially of, or consist of) at least sixteen (e.g., 16, 17, 18, 19, 20, 21, 22, 23, 24, 25, 26, 27, etc.) contiguous amino acids of any of SEQ ID NOs: ####. In some cases, the peptides include a sequence no longer than about 40 amino acids. In some cases, the peptides include a sequence of about 24 amino acids. In some cases, the peptides include a sequence of about 23 amino acids. In some cases, the peptide is 22 amino acids. In some cases, the peptide is 21 amino acids. In some cases, the peptides include modifications and/or additions on at least one terminus. For example, the peptide can include the amino acid sequence of any of SEQ ID NOs: #### with additions on the C-terminus, on the N-terminus, or on both the C- and the N-terminus. In some instances, the compound includes a peptide and an electrophilic group that is attached to the N-terminus of the peptide and the peptide includes a modification and/or additions on the C-terminus. In some cases, the at least sixteen contiguous amino acids of any of SEQ ID NOs: #### are part of a longer polypeptide. In some cases, the peptide includes at least 21 contiguous amino acids of any of SEQ ID NOs: #### and the peptide is part of a longer peptide.

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The addition of polyethelene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula: XO—(CH2CH2O)n-CH2CH2-Y where n is 2 to 10,000 and X is H or a terminal modification, e.g., a C1-4 alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available. PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, a macromolecular polymer (e.g., PEG) is attached to a compound described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as —NH(CH2)nC(O)—, wherein n=2-20 can be used. These alkyl linkers may further be substituted by any non-sterically hindering group such as lower alkyl (e.g., C1-C6) lower acyl, halogen (e.g., Cl, Br), CN, NH2, phenyl, etc. U.S. Pat. No. 5,446,090 describes a bifunctional PEG linker and its use in forming conjugates having a peptide at each of the PEG linker termini.

The peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration. Therefore the compounds comprising a peptide disclosed herein can comprise a peptide that has been modified, e.g., to further facilitate cellular uptake, increase in vivo stability, or have an enhanced ability to penetrate cell membranes, in some embodiments.

Peptide bonds can be replaced, e.g., to increase physiological stability of the peptide, by: a retro-inverso bonds (C(O)—NH); a reduced amide bond (NH—CH2); a thiomethylene bond (S—CH2 or CH2-S); an oxomethylene bond (0-CH2 or CH2-0); an ethylene bond (CH2-CH2); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or CH3; and a fluoro-ketomethylene bond (C(O)—CFR or CFR—C(O) wherein R is H or F or CH3.

Using these methods, the polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof. As described herein, the peptides can be further modified to include an electrophilic group.

Therefore, a compound comprising a polypeptide described herein can include a polypeptide that is modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, a compound comprising a polypeptide can include peptides that can be conjugated to, for example, polyethylene glycol (PEG); alkyl groups (e.g., C1-C20 straight or branched alkyl groups); fatty acid radicals; and combinations thereof.

In some instances, the peptides described herein can include a detectable label. As used herein, a "label" refers to a moiety that has at least one element, isotope, or functional group incorporated into the moiety which enables detection of the peptide to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to a peptide at any position that does not interfere with the biological activity or characteristic of the inventive polypeptide that is being detected.

Labels can include: labels that contain isotopic moieties, which may be radioactive or heavy isotopes, including, but not limited to, 2H, 3H, 13C, 14C, 15N, 31P, 32P, 35S, 67Ga, 99mTc (Tc-99m), 111In, 123I, 125I, 169Yb, and 186Re; labels that include immune or immunoreactive moieties, which may be antibodies or antigens, which may be bound to enzymes (e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, 123I, 125I, 130I, 131I, 133I, 135I, 47Sc, 72As, 72Se, 90Y, 88Y, 97Ru, 100Pd, 101mRh, 119Sb, 128Ba, 197Hg, 211 At, 212Bi, 212Pb, 109Pd, 111In, 67Ga, 68Ga, 67Cu, 75Br, 77Br, 99mTc, 14C, 13N, 150, 32P, 33P, and 18F.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc.

Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and Handbook of Fluorescent Probes and Research Products, Molecular Probes, 9th edition, 2002).

Methods of synthesizing the compounds described herein are known in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P.G.M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

For example, the peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the a-NH2 protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides can be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

In some embodiments, the peptides are substantially free of contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Pharmaceutical Compositions

One or more of the compounds (e.g., compound comprising peptides) disclosed herein (e.g., one or more of SEQ ID NOs: ####) can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously); and/or for oral administration, transmucosal administration, and/or topical administration (including topical (e.g., nasal) sprays and/or solutions).

In some instances, pharmaceutical compositions can include an effective amount of one or more peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of cancer).

The therapeutic and/or biologic agents can be administered in an effective amount, at dosages and for periods of time necessary to achieve the desired result. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

Dosage regimens can be adjusted to provide the optimum therapeutic response. For example, several divided doses can be administered daily or the dose can be proportionally reduced as indicated by the exigencies of the therapeutic situation.

A pharmaceutical composition provided herein can include one or more peptides and any pharmaceutically acceptable carrier, delivery agent, and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound. As used herein the term "pharmaceutically acceptable carrier" includes solvents, dispersion media, coatings, antibacterial and antifungal agents, isotonic and absorption delaying agents, and the like, compatible with pharmaceutical administration.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. Carrier proteins can include any protein that increases or enhances immunogenicity in a subject. Exemplary carrier proteins are described in the art (see, e.g., Fattom et al., Infect. Immun., 58:2309-2312, 1990; Devi et al., Proc. Natl. Acad. Sci. USA 88:7175-7179, 1991; Li et al., Infect. Immun. 57:3823-3827, 1989; Szu et al., Infect. Immun. 59:4555-4561, 1991; Szu et al., J. Exp. Med. 166:1510-1524, 1987; and Szu et al., Infect. Immun. 62:4440-4444, 1994). Polymeric carriers can be a natural or a synthetic material containing one or more primary and/or secondary amino groups, azido groups, or carboxyl groups. Carriers can be water soluble.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). As previously mentioned, pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Methods of Treatment

The disclosure includes methods of using the compounds (e.g., compounds comprising the peptides) described herein for the prophylaxis and/or treatment of cancer. The terms "treat" or "treating," as used herein, refers to partially or completely alleviating, inhibiting, ameliorating, and/or relieving the disease or condition from which the subject is suffering. Often, treating with the compounds described herein results in apoptosis of the cancer cells; thus the treatment can result in a reduction in tumor or cancer cells and a return to or increase in normal cells.

In some embodiments, the present disclosure provides methods for using any one or more of the peptides or pharmaceutical compositions (indicated below as 'X') disclosed herein in the following methods: Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In general, methods include administering a therapeutically effective amount of one or more of the peptides herein, to a subject who is in need of, or who has been determined to be in need of, such treatment, e.g., in or as a pharmaceutical composition, and optionally repeating administration as required for the prophylaxis or treatment of a cancer.

Skilled practitioners will appreciate that a subject who is in need of, such treatment, can be diagnosed by a physician (or veterinarian, as appropriate for the subject being diagnosed) as suffering from or at risk for a condition described herein, e.g., cancer, by any method known in the art, e.g., by assessing a patient's medical history, performing diagnostic tests, and/or by employing imaging techniques.

The peptides described herein can also be used to predict how responsive or sensitive to chemotherapy a subject's tumor or cancer is likely to be.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Treatment of carcinomas, adenocarcinomas, and sarcomas is within the present disclosure. The term "carcinoma" is art recognized and refers to malignancies of epithelial or endocrine tissues. The term also includes carcinosarcomas, which include malignant tumors composed of carcinomatous and sarcomatous tissues. "Adenocarcinoma" refers to a carcinoma derived from glandular tissue or in which the tumor cells form recognizable glandular structures. The term "sarcoma" is art recognized and refers to malignant tumors of mesenchymal derivation.

Cancers that may be treated using the methods, compositions, and devices of the present invention include, for example, cancers, e.g., tumors, of the stomach, colon, rectum, mouth/pharynx, esophagus, larynx, liver, pancreas, lung, breast, cervix uteri, corpus uteri, ovary, prostate, testis, bladder, skin, bone, kidney, brain/central nervous system, head, neck and throat; sarcomas, choriocarcinomas, and lymphomas, among others. Metastatic tumors can be treated using methods described herein. For example, performing a treatment method described herein on a tumor located at one site in the subject's body (e.g., a primary tumor), can stimulate the subject's immune defenses against the tumor and cause an immune attack on tumors of the same or even different type of at another site(s) in the subject's body (e.g., a metastatic tumor). A metastatic tumor can arise from a multitude of primary tumor types, including but not limited to those of prostate, colon, lung, breast, bone, and liver origin.

Metastases develop, e.g., when tumor cells shed from a primary tumor adhere to vascular endothelium, penetrate into surrounding tissues, and grow to form independent tumors at sites separate from a primary tumor.

Cancers that may be treated using the methods, compositions, and devices of the present invention also include blood cancers, for example, cancers of the bone marrow, blood, and lymphatic system (which includes, e.g., the lymph nodes and lymphatic vessels). Blood cancers include, for example, leukemia, myelomas, and lymphomas.

Methods of Detecting Cancer Cells

The disclosure includes methods of using compounds described herein for detecting the presence of Mcl-1, Bcl-xL, Bfl-1, both Mcl-1 and Bcl-xL, both Mcl-1 and Bfl-1, or both Bcl-xL and Bfl-1 in cells, e.g., cancer or tumor cells. A cell can be contacted with one or more compounds described herein, such as one or more peptides that include a detectable label, to detect the presence of Mcl-1, Bcl-xL, or Bfl-1. For example, a cell can be contacted with a peptide attached to detectable label described herein that is used as a probe that binds to Bfl-1. Binding of the peptide to the Bfl-1 in the cell can then be detected by using any of the methods known in the art for detecting and quantifying binding of labeled peptides to proteins, for example, histology, FACS, or western blot. Additionally, a cell can be contacted with peptides that are selective for both Mcl-1 and Bcl-xL or for both Mcl-1 and Bfl-1 or for both Bcl-xL and Bfl-1. For example, a cell can be contacted with a peptide attached to detectable label described herein that is used as a probe that binds either Mcl-1 or Bcl-xL.

The amount of labeled peptide bound to Mcl-1 versus Bcl-xL can be determined by determining the amount of peptide bound to either target protein individually relative to the total labeled peptide by detecting and quantifying binding of labeled peptides to both target proteins in the same sample, for example, histology or western blot analysis.

The disclosure includes methods of using the compounds described herein for detecting cancer or tumor cells that are characterized by expressing Bcl-2 family proteins, specifically Bfl-1, Mcl-1, and/or Bfl-1. For example, cells that are dependent on a specific Bcl-2 family protein, have Bcl-2 family protein-induced resistance to chemotherapeutics, or overexpress one or more Bcl-2 family members. The assay to diagnose these cancer cells involves contacting cells with the compounds described herein, and measuring the mitochondrial outer membrane permeabilization (MOMP) of the cell. In some cases, the assay includes, permeabilizing the cancer cell, contacting cells with the compounds described herein, and measuring the mitochondrial outer membrane permeabilization (MOMP) of the cell. In some cases, the assay includes, isolating mitochondria from the cells of interest, contacting the cells with the compounds described herein, and measuring the mitochondrial outer membrane permeabilization (MOMP). Using this method, cells that are dependent on Bfl-1, overexpress Bfl-1, or have Blf-1-induced resistance to chemotherapeutics will demonstrate increased MOMP (e.g., in comparison to non-cancerous cells or cells that are not Bfl-1 dependent, don't overexpress Bfl-1, or don't have Bfl-1 induced resistance to chemotherapeutics).

In any of the methods described herein, the cells can be permeabilized by permeabilizing agent(s) known in the art, including, for example, digitonin, saponin, or streptolysin, etc. Cells can also be permeabilized by methods, for example, such as electroporation.

The compounds (e.g., compounds comprising the peptides) described herein are particularly useful for diagnosing the dependence of cancer cells on the anti-apoptotic protein Bfl-1, as they are relatively selective and specific for Bfl-1 in comparison to other anti-apoptotic proteins in the Bcl-2 protein family. This can aid in predicting how sensitive a subject will be to a particular chemotherapy treatment or how well a subject will react to a treatment.

The peptides described herein can be used in combination or in tandem with peptides demonstrating selectivity for other Bcl-2 family proteins, e.g., for example, peptides selective for Bcl-xL, Mcl-1, and/or Bcl-2.

As described, the peptides described herein can include a detectable label. The peptides described herein can be conjugated (e.g., attached) to a dye for imaging using any of the methods known in the art for imaging or quantifying a dye, for example, in histology. Peptides conjugated to a dye, as described herein, can be useful, for example, for detecting Bfl-1 expression of a cell, e.g., overexpression of Bfl-1. This can aid in, for example, predicting how well a subject will react to a particular chemotherapy treatment or diagnosing a cancer cell.

EXAMPLES

The invention is further described in the following examples, which do not limit the scope of the invention described in the claims.

Example 1. Computational Design of Peptide Sequences that Selectively Bind Bcl-2 Family Proteins Using Modified SORTCERY To predict peptide sequences that may selectively bind one or more Bcl-2 family proteins—specifically Mcl-1, Bfl-1, Bcl-xL—empirical regression models were trained using high-throughput sequence-to-affinity datasets and selective sequences were further designed with constrained optimization (see strategy outlined in FIG. 1). Monospecific peptides—e.g. peptides that selectively bind Mcl-1 with high affinity and do not bind (or bind with low affinity) either Bfl-1 or Bcl-xL—were designed to maximize the binding affinity to the target receptor (FIG. 1, see colored arrows pointing down) and constrained to bind at most only weakly to off-target receptors. Bispecific peptides—e.g. peptides that selectively bind Mcl-1 and Bfl-1 with high affinity and do not bind (or bind with low affinity) Bcl-xL—were designed to maximize the specificity gap, minimize off-target affinity, or maximize target affinity.

Figure 1:
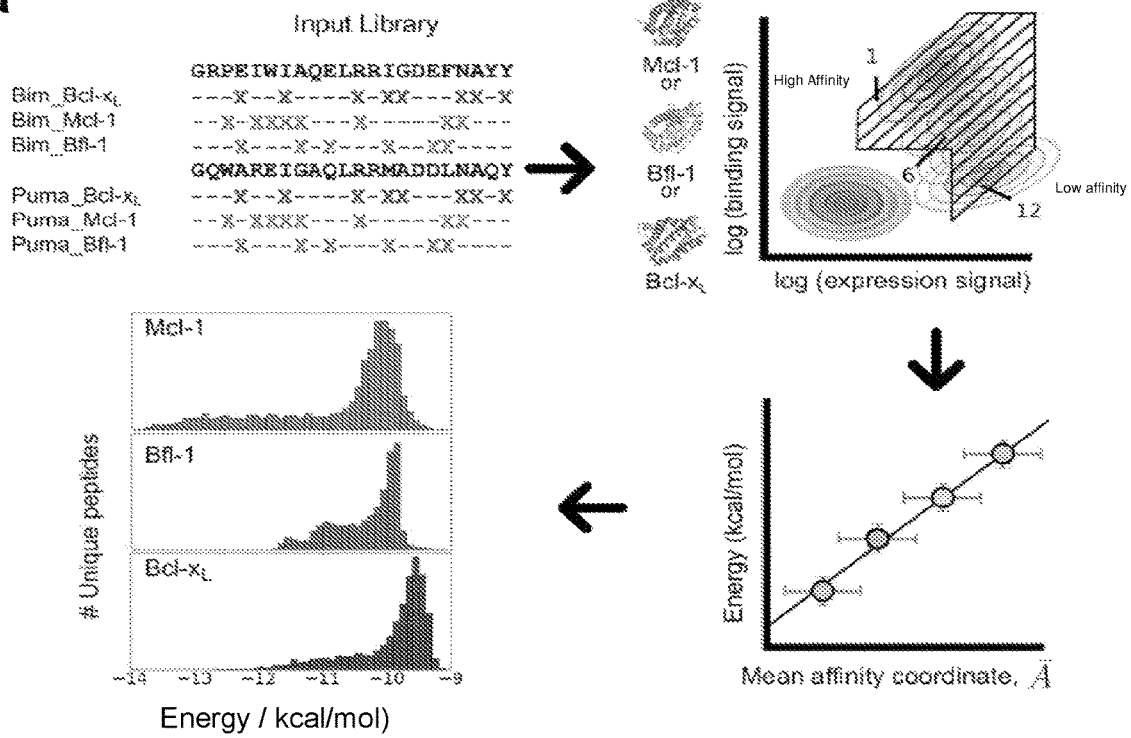
FIG. 1: Schematic depiction of design strategy using amped SORTERY (a) Three libraries targeting Mcl-1 (red), Bfl-1 (green) or Bcl-xL (blue) were synthesized in the context of Bim and Puma BH3 sequences. "X" indicates positions that were varied in each library. The six libraries were pooled, and a subset of $10^4$ clones was evaluated for binding using a 12-gate FACS scheme. Deep sequencing and data processing were used to reconstruct profiles for individual clones; the cartoon illustrates this for a library of four members, each a different color. Standards were used to convert SORTCERY mean affinity coordinates into apparent binding free energies. Apparent cell-surface binding energies were measured for 4395, 3806 and 4491 peptides binding to Bcl-xL, Bfl-1, and Mcl-1, respectively. The histograms show the distributions of apparent binding free energies, which lie between −14 and −9 kcal/mol. (b) The amped-SORTCERY binding energies of 1852 peptides to Mcl-1, Bfl-1, and Bcl-xL were plotted in three dimensions. In the 2D projection shown, the binding preference of each sequence can be inferred by its proximity to each protein axis.
Figure 1:
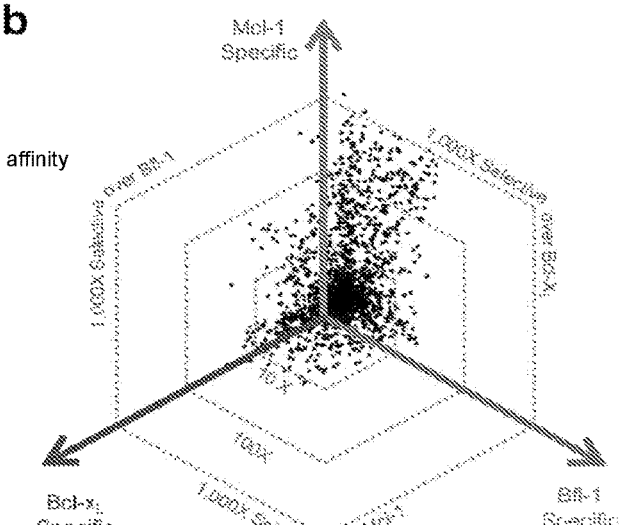

Our approach to mapping the Bcl-2 binding landscape was to collect data using the high-throughput experimental protocol SORTCERY and apply it to derive computational models to describe the functions of unobserved sequences. SORTCERY uses yeast cell-surface display, fluorescence activated cell sorting (FACS), and deep sequencing to obtain information about the binding of thousands of peptides in parallel (26, 27). Briefly, yeast cells displaying peptide ligands are separated into pools based on their normalized signals for binding to a target protein, using FACS. By deep sequencing the DNA of the encoded peptides for cells in different pools, we can reconstruct binding signals for all peptides and rank them according to their binding affinities. Here, we improved on SORTCERY by using standards to convert measurements made in arbitrary experiment-specific units into apparent free energies of binding. This allowed us to directly compare binding of peptides to different target proteins and at different protein concentrations. We call our elaboration of the original SORTCERY protocol amped (affinity mapped) SORTCERY (FIG. 1).

We applied amped SORTCERY to measure binding of the three Bcl-2 family proteins Bcl-xL, Mcl-1, and Bfl-1 to members of a diverse library of BH3-like peptides. Approximately 10,000 peptides were selected from larger combinatorial libraries that were computationally designed to be enriched in selective binders of Bcl-xL, Mcl-1 or Bfl-1 (25). The libraries contained peptides with up to 8 amino-acid mutations compared to human Bim or Puma BH3 motifs and had a theoretical diversity of 27,696,384 members; we refer to this set of sequences as the input library. The theoretical composition of the library is shown in Table X, below. The 10,000 clones to be assayed were pre-selected to have a range of affinities for Bcl-xL, Mcl-1, and Bfl-1. We performed high-throughput amped SORTCERY binding experiments for each target, in duplicate, generating six datasets. After computational filtering, each experiment provided binding data for between 1292 and 3489 unique peptides.

TABLE X

Theoretical Composition of Input Library

| | Position | Native Bim | Native Puma | Bcl-$x_L$ Specific Library | Mcl-1 Specific Library | Bfl-1 Specific Library |
|---|---|---|---|---|---|---|
| 0 | 1e | G | G | | | |
| 1 | 1f | R | Q | | | |
| 2 | 1g | P | W | | AGPRSTW | |
| 3 | 2a | E | A | DEHIKLMNQV | | AEIKLPQTV |
| 4 | 2b | I | R | | ACDFGHLPRSVY | |
| 5 | 2c | W | E | | DEHQ | |
| 6 | 2d | I | I | DFHILNVY | AITV | |
| 7 | 2e | A | G | | AGISTV | ACDGSY |
| 8 | 2f | Q | A | | | |
| 9 | 2g | E | Q | | | CDFGHILNRSVY |
| 10 | 3a | L | L | | | |
| 11 | 3b | R | R | AGIRTV | AEGIKRTV | |
| 12 | 3c | R | R | | | |
| 13 | 3d | I | M | ACDFGHILNPRSTVY | | ACFGILPRSTV |
| 14 | 3e | G | A | AG | | |
| 15 | 3f | D | D | | | |
| 16 | 3g | E | D | | | DEHIKLMNQV |
| 17 | 4a | F | L | | ADFHILNPSTVY | ADFHILNPSTVY |
| 18 | 4b | N | N | ADHILNPTV | DEHKNQ | |
| 19 | 4c | A | A | AEKT | | |

TABLE X-continued

Theoretical Composition of Input Library

| Position | | Native Bim | Native Puma | Bcl-x$_L$ Specific Library | Mcl-1 Specific Library | Bfl-1 Specific Library |
|---|---|---|---|---|---|---|
| 20 | 4d | Y | Q | | | |
| 21 | 4e | Y | Y | ACDGHNPRSTY | | AFILPSTV |

Amped SORTCERY measures affinity (A) in arbitrary units related to normalized FACS signals for pools of sorted cells. Theory predicts that A will be linearly related to cell-surface binding free energies over a certain resolution range, under certain conditions (26). To test this relationship, and to convert A measurements to apparent binding free energies in kcal/mol, we titrated peptide standards with each of the three target proteins and fit the resulting curves. Measured A values correlated well with individually measured apparent cell-surface binding free energies (referred to below as "binding energies"), with Pearson R=0.82–0.92. Linear fits for 16-18 standards per dataset gave RMSE of 0.33-0.56 kcal/mol over a range of dissociation constants from −13.8 to −8.9 kcal/mol (Table 1).

We quantified binding for 5769 unique peptides in this experiment. Binding energies measured in two amped SORTCERY replicates were reproducible, with Pearson R values of 0.91-0.98. For 1852 peptides, our experiments included measurements of binding to all three proteins Mcl-1, Bfl-1, and Bcl-xL, allowing us to visualize the binding selectivity landscape of these sequences (FIG. 1). Included were examples of peptides with up to 1000-fold specificity for binding Mcl-1 over Bfl-1 or Bcl-xL. In contrast, the most selective binders of Bfl-1 or Bcl-xL had only a 10-fold preference for those proteins.

We reasoned that if we could use amped SORTCERY data to build a computational model to capture how sequence determines binding, we could predict binding energies for peptides not measured in our experiments and generate a more complete landscape. We applied regression techniques and tested two different models. Peptide binding free energy was expressed either as a sum of independent contributions from individual residues (linear model), or as a sum of contributions from residue pairs (polynomial model of order two). Our use of a polynomial model was motivated by our observation that the contribution of a BH3 peptide residue to binding depends on its sequence context. We examined this dependence using dataset pilot_x1_r2. Briefly, we identified all pairs of Bcl-xL binding peptides that were identical except for a single residue change. For each mutation, we examined the distribution of ΔΔGbind values when the change was made in different contexts. This analysis revealed that many mutational effects followed a Gaussian distribution, consistent with random noise. However, 37 of 72 mutations observed in more than 100 contexts had distributions of ΔΔGbind values deviating significantly from a normal distribution, providing evidence that the energy contributions in different backgrounds can vary. To partially account for these context-specific effects, we tested models in which residue pairs contribute to the binding score. In such models, the impact of a particular residue depends on what residues are present at other sites in the peptide.

Figure 2:
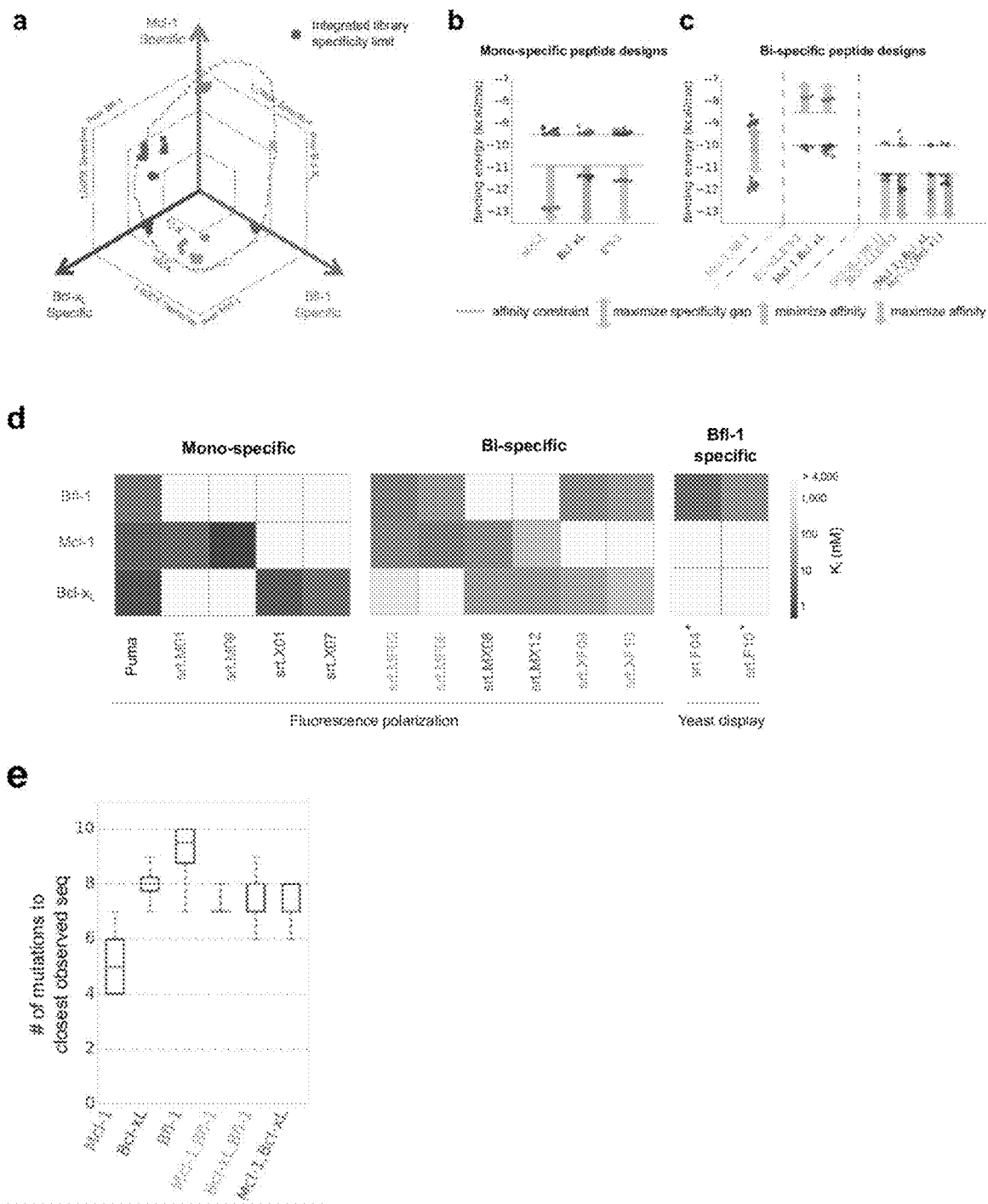
FIG. 2: Predictions from data-derived models of peptide binding (a) Nested cross-validation performance for linear and polynomial models trained on datasets Bcl-xL_r1, Bfl-1_r1 and Mcl-1_r2. R2 for models trained and evaluated on the same data in grey, R2 for models evaluated on data held out from training in colors, (b) Specificity and affinity tradeoffs for BH3 peptides binding to Mcl-1 and Bfl-1. The 27,696, 384 peptides in the input library were scored for binding to Mcl-1, Bfl-1, and Bcl-xL. For a given target protein (x axis), peptides were binned by predicted target affinity. The median affinity for the off-target is plotted for each bin. The shaded fill indicates the 25th and 75th percentiles. Dashed lines indicate thresholds of selectivity, (c) Map of the Mcl-1/Bcl-xL/Bfl-1 specificity landscape. Black points are as in FIG. 1. Orange points show predicted binding energies for all peptides observed to bind at least one protein. Pink points show extremes in the specificity space of all theoretical input library members, including members that were not observed experimentally. A further extrapolation maps the boundaries of specificity for an integrated library space that includes all combinations of substitutions sampled in any of the six original input libraries (brown). The sizes of the sequence spaces are indicated in parentheses, (d) Binding affinities determined using fluorescence polarization competition experiments or cell-surface measurements. Average values over replicates are shown. *For the Bfl-1 specific peptides, the highest concentration tested was 1000 nM. (e) Boxplot of the maximum sequence similarity of the designed peptides to any previously observed sequence. Designed peptides were all at least 4 mutations from any previously observed peptide measured by SORTCERY, and some differed in 10 positions from the closest characterized library member.

We used support vector regression (SVR) against amped SORTCERY data to fit the residue and/or residue-pair term contributions for each model (28). We compared the performance of linear vs. polynomial models trained on each dataset using nested cross-validation. FIG. 2, panel a, reports the average R2 for training and validation subsets, for the best model for each protein. Second-order polynomial models that accounted for residue-pair contributions consistently outperformed linear models that assumed residue independence, when trained on the same data and tested using validation sequences non-overlapping with the training data.

Our data-derived models provided an opportunity to investigate whether high affinity for one Bcl-2 family protein is predicted to correlate with high affinity for other family members. For sequences in the input library, the peptides predicted to bind most tightly to Mcl-1 were predicted by our polynomial regression models to bind >1000-fold weaker to Bcl-xL and >100-fold weaker to Bfl-1, on average (FIG. 2 panel b). In contrast, peptides from these libraries that were predicted to bind tightly to Bfl-1 were predicted to bind >10 times more tightly to Mcl-1, on average (FIG. 2, panel b). This analysis suggests that it might be difficult to identify high-affinity binders of Bfl-1 that do not bind to Mcl-1, which is consistent with prior observations and library screening experiments (29, 30).

We used our models for Mcl-1, Bfl-1, and Bcl-xL binding to expand our peptide specificity landscape map. Because only 1852 of 5769 observed peptides had binding measurements for all three proteins, we first used our models to predict the binding energies of the other 3917 sequences for all three proteins (orange in FIG. 2, panel c). Then, we computed the predicted distribution of binding scores for all 27,696,384 input library sequences, most of which were not tested experimentally. The extremes of this distribution are shown in pink in FIG. 2, panel c, indicating that our input library was enriched in Mcl-1 specific sequences relative to Bfl-1 or Bcl-xL specific sequences, according to our models.

Finally, although our models were trained on sequences from the input library space, we made predictions about sequences outside of this space. Specifically, we scored 1014 sequences made from all combinations of residues that were considered at any position in any component library of the input library. This space, the integrated library space, includes many residue combinations that were never sampled experimentally, including sequences that mix residues from the Bim and Puma backgrounds. Sequences at the boundary of this space (brown in FIG. 2, panel c) demonstrate that predicted selectivity can be as much as tenfold greater in the integrated library space than in the input library space, particularly for Bfl-1 and Bcl-xL.

Figure 3:
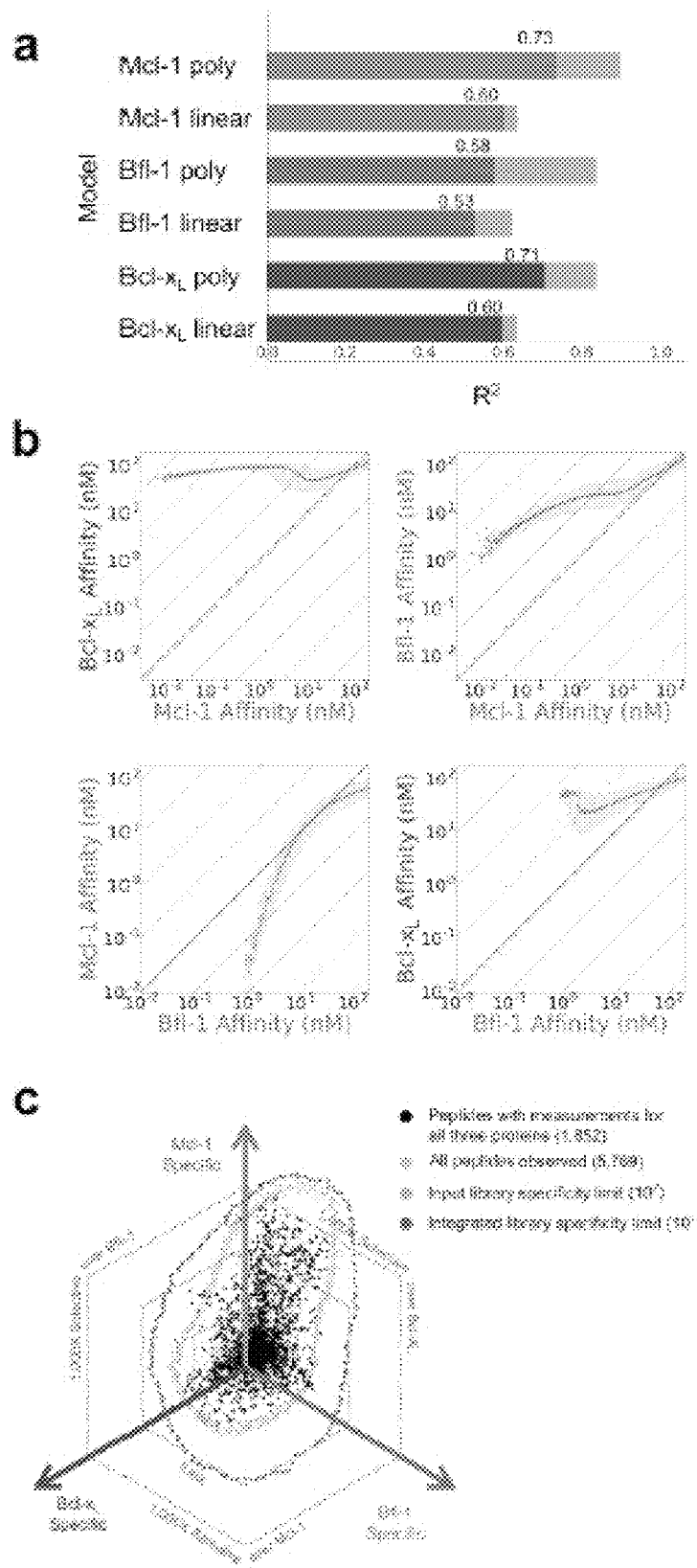
FIG. 3: Peptide design using data-derived models (a) Designed peptides plotted in the specificity landscape. Peptides were designed to bind to Mcl-1 (red), Bfl-1 (green), or Bcl-xL (blue), without cross-reacting with the other two proteins. Bispecific peptides were designed to interact with Mcl-1 and Bfl-1 (orange), Bcl-xL and Bfl-1 (teal), or Mcl-1 and Bcl-xL (purple), without binding tightly to the off-target protein. Sequences were designed using constrained optimization. Monospecific peptides were designed to maximize binding affinity for the target protein, with constraints imposed on off-target binding, (b) Maximization/minimization are indicated using arrows and constraints are indicated with grey lines, (c) Bispecific peptides were designed to maximize the specificity gap, minimize off-target affinity, or maximize target affinity.

We used our landscape model to design selective peptide binders of Bcl-2 family members, including peptides designed to bind selectively to just one of Mcl-1, Bfl-1, or Bcl-xL, and bispecific peptides designed to bind two out of the three proteins (FIG. 3, panel a).

We posed design as a sequence optimization problem and used integer linear programming (ILP) to solve for sequences that met different design criteria. We used constrained optimization to balance the dual objectives of tight binding to the target(s) and weak binding to the off-target(s) (31). For example, for the single-target specific peptides, we used ILP to maximize the predicted target-binding affinity while imposing a lower limit on the predicted binding free energy for the off-targets (FIG. 3, panel b).

The peptide sequences that were computationally predicted and optimized to bind one or more Bcl-2 family proteins are listed in Tables 1-8.

TABLE 1

Sequences for peptides predicted to selectively bind Mcl-1 and Bfl-1 with high affinity and to not bind (or bind with low affinity) Bcl-xL.

| SEQ ID NO: | ID | Sequence |
|---|---|---|
| 7 | MF01 | GRRIDEIAQILRRIGDHIEKYI |
| 8 | MF02 | GRWIDQIAQFLRRIGDHIEKYI |
| 9 | MF03 | GRRVDEIAQILRRIGDNIEEYI |
| 10 | MF04 | GRRVDEIAQILRRIGDNINEYI |
| 11 | MF05 | GRRIDEIAQILRRIGDHVEKYI |
| 12 | MF06 | GRRVDEIAQILRRIGDNVTTYI |
| 13 | MF07 | GRRVDEIAQILRRIGDQIEEYI |

TABLE 2

Sequences for peptides predicted to selectively bind Mcl-1 and Bcl-xL with high affinity and to not bind (or bind with low affinity) Bfl-1.

| SEQ ID NO: | ID | Sequence |
|---|---|---|
| 14 | MX08 | GQWLRWVIAELIRIADEFHAQY |
| 15 | MX09 | GQWLYWVAAELVRIADDFLAQR |
| 16 | MX10 | GQSLIWFIAELARIGDEFHEYY |
| 17 | MX11 | GQWLIWYIAELIRIADEFHAQF |
| 18 | MX12 | GQWLRDVVAELARIADEFHAQY |
| 19 | MX13 | GQWLIWYIAELRRYADEFHAQI |
| 20 | MX14 | GQWLIWVAAQLRRYADEFHAQR |
| 21 | MX15 | GQWLIWYAAELARLADDFHAQR |
| 22 | MX16 | GQWLIWYAAQLARIADEFHAQR |
| 23 | MX17 | GQSLIWYIAELARIADEFAAQY |

TABLE 3

Sequences for peptides predicted to selectively bind Bfl-1 and Bcl-xL with high affinity and to not bind (or bind with low affinity) Mcl-1.

| SEQ ID NO: | ID | Sequence |
|---|---|---|
| 24 | XF08 | GQRLIWIGAGLRRLADEFDKQA |
| 25 | XF09 | GQRIIWIAAELRRAADELDKQI |

TABLE 3-continued

Sequences for peptides predicted to selectively bind Bfl-1 and Bcl-xL with high affinity and to not bind (or bind with low affinity) Mcl-1.

| SEQ ID NO: | ID | Sequence |
|---|---|---|
| 26 | XF10 | GQRIIWIAAELRRAADQLDAQI |
| 27 | XF11 | GQRIIWIGAELRRLADELDKQV |
| 28 | XF12 | GQRIIWIAAELRRAADQLDKQY |
| 29 | XF13 | GQRIIWIAAGLRRLADELDKQL |
| 30 | XF14 | GQALIWIGAELRRLADEFNKQL |
| 31 | XF15 | GQRLIWIGAELRRLADEFDKQL |
| 32 | XF16 | GQPLIWIGAELRRLADEFNKQV |
| 33 | XF17 | GQRLIWIGAELRRLADDFDKQY |
| 34 | XF18 | GQRLIWIGAELRRLADEFNKQA |

TABLE 4

Sequences for peptides predicted to selectively bind Mcl-1 and Bcl-xL with high affinity and to not bind (or bind with low affinity) Bfl-1.

| SEQ ID NO: | ID | Sequence |
|---|---|---|
| 35 | MX1 | GRSQIWYVQELVRGGDVNHAYR |
| 36 | MX2 | GRSQIWYDQELVRSGDVNAAYR |
| 37 | MX3 | GRSQIWYDQELVRSGDENAAYR |
| 38 | MX4 | GRSQIWYDQELVRYADVNAAYR |
| 39 | MX5 | GRSQIWYDQELVRYGDVNAAYR |
| 40 | MX6 | GRSQIWYVQELVRSGDVNHAYR |
| 41 | MX7 | GRSEIWYDQELVRSGDVNAAYR |

TABLE 5

Sequences for peptides predicted to selectively bind Bfl-1 and Bcl-xL with high affinity and to not bind (or bind with low affinity) Mcl-1.

| SEQ ID NO: | ID | Sequence |
|---|---|---|
| 42 | XF1 | GRRVVWIGQGLKRLADEYHKYA |
| 43 | XF2 | GRREVWLSQSLKRIADQFQKYL |
| 44 | XF3 | GRREIWLSQYLKRIADLFQKYL |
| 45 | XF4 | GRREIWLSQSLKRIADMFQKYL |
| 46 | XF5 | GRREIWLSQSLKRIADLFQKYL |
| 47 | XF6 | GQRVDDFGQGLKRVADEYHAQA |
| 48 | XF7 | GRREVWLSQSLKRIADQFQTYL |

TABLE 6

Sequences for peptides predicted to selectively bind Mcl-1 with high affinity and to not bind (or bind with low affinity) Bfl-1 or Bcl-xL.

| SEQ ID NO: | ID | Sequence |
| --- | --- | --- |
| 49 | M1 | GRSELEVVQELVRIGDIVVAYF |
| 50 | M2 | GRSEYEYIQELVRIGDEVDAYF |
| 51 | M3 | GRSLYEYIQELIRIGDEVTAYF |
| 52 | M4 | GRSLLEYIQELIRIGDEVIAYF |
| 53 | M5 | GRSELEYIQELVRIGDEVDAYF |
| 54 | M6 | GRGQLEYIQELIRIGDIVDAYF |
| 55 | M7 | GRSELEYIQELIRIGDNVDAYF |
| 56 | M8 | GRSELEYIQELIRIGDIVDAYF |
| 57 | M9 | GRSQYEVIQELIRIGDIVLAYF |
| 58 | M10 | GRSEYEYIQELIRIGDNVDAYF |
| 59 | M11 | GRSEYEYIQELIRIGDIVDAYF |
| 60 | M12 | GRGQYEYIQELIRIGDIVDAYF |

TABLE 7

Sequences for peptides predicted to selectively bind Bcl-xL with high affinity and to not bind (or bind with low affinity) Mcl-1 or Bfl-1.

| SEQ ID NO: | ID | Sequence |
| --- | --- | --- |
| 61 | X1 | GQTLIWYGASLRRYADEFAKQR |
| 62 | X2 | GQTLIWYGAQLRRYADEFAKQR |
| 63 | X3 | GQPLIWFGASLRRGADEFAKQR |
| 64 | X4 | GQTLIWYGAQLRRVADDFAKQR |
| 65 | X5 | GQTAIWYGASLRRAADEFAKQR |
| 66 | X6 | GQSLIWFGASLRRGADEFAAQR |
| 67 | X7 | GQPLIWFGAQLRRGADEFAAQR |
| 68 | X8 | GQSMIWYGASLRRAADEFAKQR |
| 69 | X9 | GQTLIWYGAQLRRYADDFAKQR |
| 70 | X10 | GQRLIWYGAQLRRYADDFAKQR |
| 71 | X11 | GQTLIWFGASLRRGADEFAAQR |
| 72 | X12 | GQGLIWYGAQLRRVADDFAKQR |

TABLE 8

Sequences for peptides predicted to selectively bind Bfl-1 with high affinity and to not bind (or bind with low affinity) Mcl-1 or Bcl-xL.

| SEQ ID NO: | ID | Sequence |
| --- | --- | --- |
| 73 | F1 | GRRVRHIAQGLRRAGDQLDAYG |
| 74 | F2 | GQRVRHIAQGLRRTGDQLDAYG |
| 75 | F3 | GRRVVHIAAGLRRTGDQLEAQG |
| 76 | F4 | GQRVVHIAAGLRRTGDQLEAYG |
| 77 | F5 | GQRVVHIAQGLRRTGDQLEAQG |
| 78 | F6 | GQRVVQIAAGLRRTGDQLEKYG |
| 79 | F7 | GQRVVQIAQGLRRTGDQLEKQG |
| 80 | F8 | GRRVVQIAAGLRRTGDQLEKQG |
| 81 | F9 | GRRVRHIAQGLRRAGDQLDKYG |
| 82 | F10 | GRRVVQIAAGLRRAGDQLEKYG |
| 83 | F11 | GQRVVQIAQGLRRAGDQLEKYG |
| 84 | F12 | GRRVVQIAQGLRRAGDQLEKQG |

We measured binding of the designs to 1, 10, 100 or 1000 nM of Bcl-xL, Mcl-1 and Bfl-1 using yeast cell-surface display. All 36 designed monospecific peptides (Table 6, Table 7, and Table 8) demonstrated the desired selectivity for the intended target protein. Based on sparse titrations, the apparent dissociation constants (KD_app) for the designs binding to their targets on the cell surface were estimated to be <100 nM; there were 28 examples with KD_app <10 nM, and 5 with KD_app <1 nM. Off-target affinities were weak for all designed peptides, with estimated KD_app values >1000 nM. We used the cell-surface experiments to select six peptides, for which we determined solution Ki values using a competition fluorescence polarization (FP) assay (FIG. 3, panel d). These experiments showed Table X2) that the four designed peptides that targeted Mcl-1 or Bcl-xL bound to their intended protein tightly (KD_app <4 nM) and with greater than 1000-fold specificity, consistent with what was observed in yeast surface-display binding experiments. The Bfl-1 designs bound weakly (F10) or undetectably (F4) to Bfl-1 in the FP competition assay, despite tight and selective interaction with Bfl-1 on the yeast cell surface, which we also verified could be competed with Bim BH3 peptide. This discrepancy may be due to a limitation of the FP competition assay. Functional assays using permeabilized cells showed that both F4 and F10 selectively induced a pro-apoptotic response in Bfl-1 dependent cell lines, but not in Mcl-1 or Bcl-xL dependent cell lines (32). Further, in the cellular assay, F10 inhibited Bfl-1 at least as potently as a previously described peptide that binds Bfl-1 with Ki =15 nM (peptide FS1)(25). The designed peptides resulting from this approach have binding affinities and specificities comparable to, or possibly better than, previously reported peptide inhibitors discovered using library screening experiments (Table X3).

TABLE X2

Affinities of designed peptides for Bfl-1, Bcl-xL, and Mcl-1 determined using competition fluorescence anisotropy binding experiments

| name | sequence* | Bfl-1 | Mcl-1, | Bcl-x$_L$ |
|---|---|---|---|---|
| | | $K_i$ (nM) ∧ | | |
| Puma | QWAREIGAQLRRMADDLNAQYER | 4.8 ± 1.8 | 1.69 ± .11 | 1.00 ± .14 |
| srt.F10 | RRVVQIAAGLRRAGDQLEKYGER | 300 ± 200 | >4000 | >4000 |
| srt.F4 | QRVVHIAAGLRRTGDQLEAYGER | >4000 | >4000 | >4000 |
| srt.M1 | RSELEVVQELVRIGDIVVAYFER | >4000 | 2.4 ± .7 | >4000 |
| srt.M9 | RSQYEVIQELIRIGDIVLAYFER | >4000 | 0.6 ± .3 | >4000 |
| srt.X1 | QTLIWYGASLRRYADEFAKQRER | >4000 | >4000 | 1.32 ± .18 |
| srt.X7 | QPLIWFGAQLRRGADEFAAQRER | >4000 | >4000 | 3.7 ± .3 |
| srt.MF02 | RWIDQIAQFLRRIGDHIEKYIER | 6.6 ± 1.0 | 9 ± 5 | 1000 ± 200 |
| srt.MF06 | RRVDEIAQILRRIGDNVTTYIER | 19 ± 4 | 5.7 ± 1.2 | >4000 |
| srt.MX01 | QWLRWVIAELIRIADEFHAQYER | >4000 | 11 ± 4 | 21 ± 2 |
| srt.MX05 | QWLRDVVAELARIADEFHAQYER | >4000 | 100 ± 30 | 20 ± 5 |
| srt.XF02 | QRIIWIAAELRRAADELDKQIER | 10 ± 3 | >4000 | 37 ± 4 |
| srt.XF03 | QRIIWIAAELRRAADQLDAQIER | 22.0 ± 1.3 | >4000 | 120 ± 10 |
| | | $K_d$ (nM) # | | |
| Fluoresceinated Bim (competitor) | (fl)IWIAQELRRIGDEFNAYY | 4 ± 1 | 0.8 ± 0.4 | 6 ± 1 |

*Peptides made for solution binding studies were capped by N-terminal acetylation and C-terminal amidation. The competitor peptide (fluoreceinate Bim) was capped with N-terminal fluorescein and C-terminal amidation. To perform competition fluorescence polarization experiments, unlabeled peptide was titrated (0-10 μM) into 50 nM Bfl-1, Mcl-1, or Bcl-x$_L$ and 25 nM fluoresceinated Bim BH3 and equilibrated for >3 hours.
∧Errors are standard deviations for three replicate experiments.
$K_D$ values for this fluoresceinated Bim BH3 peptide as reported by Dutta et al. 2013(4).

TABLE X3

Comparison of affinities and specificities for selected designed peptides and previously reported selective peptides reported affinity (nM)

| name | Bfl-1 | Mcl-1 | Bcl-x$_L$ | Reference |
|---|---|---|---|---|
| srt.M1 | >4000 | 2.4 ± .7 | >4000 | this study |
| srt.M9 | >4000 | 0.6 ± .3 | >4000 | this study |
| MS1 | >5000 | 1.9 ± 1.0 | 1600 ± 2300 | (13) |
| MS2 | 3100 ± 2300 | 1.5 ± 1.0 | 1400 ± 500 | (13) |
| MS3 | 790 ± 140 | 2.0 ± 1.2 | 2300 ± 1000 | (13) |
| srt.X1 | >4000 | >4000 | 1.32 ± 0.18 | this study |
| srt.X7 | >4000 | >4000 | 3.7 ± 0.3 | this study |
| XXA1 | >1000 | >1000 | 0.09 ± .03 | (14) |
| XXA4 | >1000 | >300 | 0.2 ± 0.1 | (14) |
| srt.F4 | 14 ± 2 | >1000 | >1000 | this study |
| srt.F10 | 3.2 ± 0.4 | >1000 | >1000 | this study |
| FS1 | 15 ± 3 | >5000 | 2400 ± 400 | (1) |
| FS2 | 21 ± 6 | 3200 ± 300 | >5000 | (1) |
| FS3 | 2.1 ± 0.3 | 550 ± 150 | 320 ± 90 | (1) |
| FD1 | 0.7 ± 0.2 | 0.1 ± 0.02 | 5 ± 0.4 | (4) |
| FD2 | 3.6 ± 0.7 | 1 ± 0.1 | 18 ± 0.2 | (4) |
| FA1 | Not Equilibrated | 1 ± 0.1 | 8 ± 0.2 | (4) |
| FW1 | 8 ± 2 | 0.2 ± 0.04 | 20 ± 4 | (4) |

To design bi-specific peptides, we first identified sequences that maximized the difference between the predicted affinities for targets Mcl-1 and Bfl-1 vs. off-target Bcl-xL. All seven peptides that were designed this way bound to Mcl-1 and Bfl-1 at 1 nM protein concentration on the cell surface and had lower affinity for Bcl-xL. We estimated the dissociation constants of MF2 and MF6 for Bcl-xL as >1000 nM on the cell surface, and subsequent studies in solution confirmed Ki values >100 fold tighter to Mcl-1 and Bfl-1 than to Bcl-xL (FIG. 3, panel d). This may be the easiest bi-specific design problem to solve for this set of proteins, because our analysis in FIG. 2, panel b, predicted that affinities for Mcl-1 and Bfl-1 are more strongly correlated than are affinities for Mcl-1 and Bcl-xL or Bfl-1 and Bcl-xL.

For the other bi-specific combinations, we first tried minimizing the affinity of peptides for the off-target protein while constraining the predicted energy of binding to the targets to be <−10 kcal/mol (FIG. 3, panel c). This did not yield peptides with the desired profiles; peptides designed to bind to Bcl-xL and Bfl-1 bound tightly only to Bcl-xL, and those designed to bind to Bcl-xL and Mcl-1 did not bind detectably to either. This could be because models based on amped SORTCERY underestimate the destabilizing effects of some residues, because the experiment does not resolve differences in affinity beyond a given detection limit. In another round of design, we set up the optimization to minimize the target binding energy, with constraints imposed on the off-target binding energies (off-target binding energy >−10 kcal/mol). This approach yielded several dual-specific peptides, as confirmed using yeast display.

Two of the most promising peptides for each design goal were tested for binding in solution (FIG. 3, panel d). Our best dual-specific Bcl-xL/Bfl-1 inhibitors bound with Ki values <120 nM for target proteins and >4000 nM for the off-target, and our best dual-specific Mcl-1/Bcl-xL inhibitors bound with bound with Ki values <100 nM for target proteins and >4000 nM for the off-target.

Figure 4:
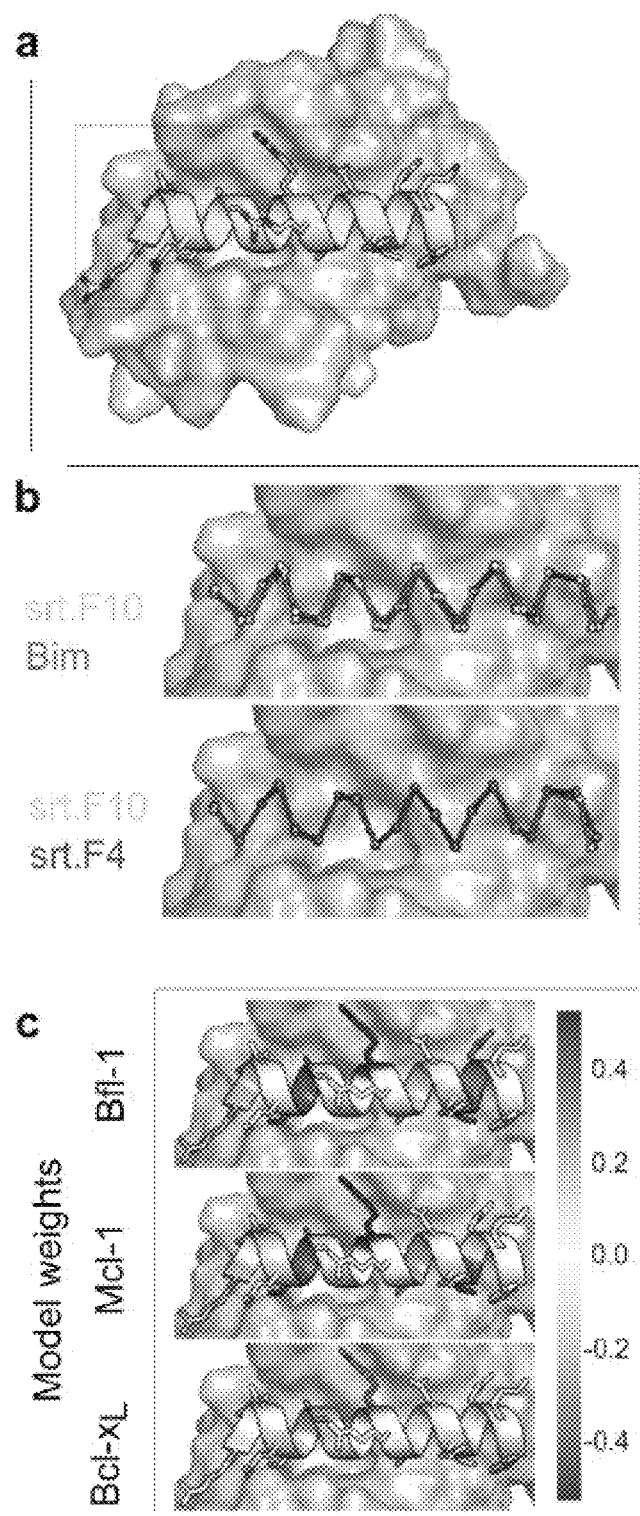
FIG. 4: Crystal structure and design weights for selective Bfl-1 binder F10

All of the designed peptides that we tested were 4-10 mutations away from any previously observed sequence (FIG. 2, panel e); designs were also >9 mutations away from any native BH3 motif. The sequences were on average 3.6-4.0 mutations different from each other. For the 12 peptides that we tested, the designs bound competitively with a Bim BH3 peptide, consistent with them interacting at the same site. To investigate the details of the binding mode, we solved crystal structures of F4 and F10 bound to Bfl-1 (FIG. 4, panel a). These are the two peptides that bound Bfl-1 with high affinity in yeast display but did not give a solution binding signal. Both complexes were resolved at high resolution (1.48 Å in both cases), and FIG. 4b shows superimpositions of each structure with the structure of Bfl-1 bound to Bim BH3, revealing high similarity.

A benefit of performing rational design using predictive models is that the models provide detailed hypotheses about why certain complexes are stable vs. unstable. FIG. 4, panel c, shows the residue contribution weights from our three different models mapped onto the structure of F10 bound to Bfl-1, using a heatmap to indicate residues that are net stabilizing vs. destabilizing. The favorable contributions of most residues to Bfl-1 binding are reflected in a mostly blue colored peptide, at top. In contrast, our models for Bcl-xL and Mcl-1 binding highlight, in red, residues that are predicted to destabilize binding and thereby contribute to specificity. The model weights indicate that the specificity of the designs comes from contributions from many residues throughout the peptide.

Deep sequencing combined with library display technologies makes it possible to explore and model larger parts of the protein interaction universe than ever before. Amped SORTCERY can quantify apparent cell surface binding energies for thousands of diverse ligands in high throughput. We used this technique to measure peptide binding to three related proteins: Bfl-1, Mcl-1, and Bcl-$x_L$. We further expanded our description of the Bcl-2 binding landscape using models trained on the experimental data, and we demonstrated that models derived by regression can be used to design protein sequences up to ten mutations away from the training set, for peptides that are just 23 residues long. We achieved 100% success designing specific peptide binders of all three targets Bfl-1, Mcl-1, and Bcl-$x_L$.

Interestingly, our designed peptides were often more specific for their targets than was predicted by our models. For example, several peptides, such as srt.X01 and srt.X07, predicted by our models to have a 26-38-fold preference for their target, were found to be >1000-fold specific in solution binding assays. Frequently, the designed peptides showed less off-target binding than was predicted. The restricted dynamic range of the amped SORTCERY measurements might explain this. Models that underestimate destabilizing effects could overestimate how well the designs bind off-target proteins. Performing amped SORTCERY at higher protein concentrations would likely enable more accurate measurement of weaker affinities.

Strikingly, we were able to use data collected in multiple local sequence spaces to build models with utility for navigating the binding landscape outside of those spaces. Computational design may be an easier task than prediction, particularly in regions of the landscape that are remote from the training data. Regression modeling captures the average contribution that a residue or residue pair makes in different contexts. If the training data are dominated by a single canonical peptide binding mode, then average residue contributions may be good estimates of the actual contributions of residues in that binding mode, and a regression model may work well for designing peptides that bind in that mode. Such a model would be less good at scoring peptides that bind in a different geometry. Consistent with this, srt.F4 and srt.F10 closely imitate the binding pose of Bim BH3 (FIG. 4b). Also consistent with this, our models substantially underestimated the Bfl-1-binding specificity of previously described peptides, by >30-fold. Bfl-1-selective peptide FS2 binds to Bfl-1 in a shifted and rotated geometry relative to other known BH3 peptides(25), and the residue weights that define the landscape presented here do not provide accurate affinity predictions for FS2.

An advantage of design guided by this type of sequence-based model is that once the model is built, using it to search sequence space is very fast. It is also simple to optimize features that can be hard to screen for experimentally(31). In this work, we performed experiments on libraries that were designed to be enriched in mono-selective binders and used the data to design bi-specific binders. One could imagine adding additional constraints to design for net charge, which can impact solubility and cell delivery, or minimal predicted immunogenicity(33). The formalism of the design optimization can readily accommodate diverse constraints on protein amino-acid composition or sequence(34). Another advantage of this approach is that it does not require a structure as input or structure-based modeling as part of the design process.

The increasing ease with which we can generate and screen peptide and protein libraries means that mapping landscapes through model building will become a useful tool in the repertoire of protein design (35-38). An interesting question is what sequence space should be sampled to support initial model building. Naïve empirical models will be most accurate close to the sequence space on which they were trained. One way to broaden this space would be to measure affinities for sequences that vary more sites and residues.

However, there is a tradeoff between increasing library diversity and obtaining adequate coverage of combinations of residues. Sampling a broader sequence space additionally decreases the chances of observing binders. Prior information about a protein complex can guide landscape exploration and increase the chances that experimentally sampled sequences will have an observable function. In this work, we studied a short alpha-helical peptide ligand for which previous studies provided insights into BH3 sequence-function relationships. Appropriate input libraries for other protein complexes, about which less is known, could be designed using structure-based modeling and/or sequence information from homologs(1, 39-42). Another approach could be to use iterative strategies that start with naïve sampling (e.g. using deep mutational scanning(43)) and apply the resulting data to direct additional sequence mapping to promising parts of the binding landscape.

Methods

Protein constructs Anti-apoptotic protein constructs used in this work correspond to human Bcl-xL residues 1-209, Mcl-1 residues 172-327 and Bfl-1 residues 1-151, expressed in *E. coli* and purified as described by Dutta et al. (45).

Yeast growth and sorting Yeast cultures were diluted from glycerol stocks (OD600=0.05) and passaged in SD+CAA (5 g/L casamino acids, 1.7 g/L yeast nitrogen base, 5 g/L ammonium sulfate, 10.2 g/L $Na_2HPO_4\_7H_2O$ and 8.6 g/L $NaH_2PO_4\_H_2O$, 2% glucose) for 12 hr at 30° C. The cultures were then diluted (OD600=0.005-0.01) in SD+CAA and grown to an OD600=0.1-0.6 at 30° C. To induce expression, cultures were diluted 25-fold in SG+CAA (5 g/L casamino acids, 1.7 g/L yeast nitrogen base, 5 g/L ammonium sulfate, 10.2 g/L $Na_2HPO_4\_7H_2O$ and 8.6 g/L $NaH_2PO_4\_H_2O$, 2% galactose) and grown for 20-24 hr at 30° C. Cells were filtered with a 0.45 μm filter, washed twice with BSS (50 mM Tris, 100 mM NaCl, pH 8, 1 mg/ml BSA), resuspended in BSS with least 10-fold molar excess target protein, and incubated for 2h at room temperature with gentle shaking. To detect cell-surface expression and binding, cells were filtered, washed twice in chilled BSS, resuspended in a 100-fold dilution of primary antibodies (mouse anti-HA/Roche and rabbit anti-c-myc/Sigma) in BSS at a volume of 2 mL per $10^8$ cells and incubated for 15 min at 4° C. Cells were filtered, washed twice in chilled BSS, resuspended in a 40-fold dilution of allophycocyanin (APC) rat anti-mouse (BD Biosciences) and a 100-fold dilution of phycoerythrin (PE) goat anti-rabbit (Sigma) secondary antibodies in BSS at a volume of 2 mL per $10^8$ cells, and incubated in the dark for 15 min at 4° C. Cells were filtered and washed 2× in chilled BSS before resuspending the labeled cells in BSS and using a BD FACSAria flow cytometer or a BD FACSCanto and FACSDiva software for cell sorting or analysis.

To clone the designed peptides, EBY100 yeast cells were transformed using the Frozen-EZ Yeast Transformation II Kit (Zymo Research) according to the manufacturer's protocol. For a plasmid backbone, we used the Puma PCT plasmid (25) and digested it with XhoI (NEB) and NheI-HF (NEB) according to the manufacturer's protocol. The inserts were constructed with PCR using primers that encoded the peptide sequence flanked with at least 40 bp of the plasmid sequence on either side of the insertion site. The inserts and plasmid backbones were mixed 5:1 for transformation. The transformation mixture was spread onto SD+CAA plates (46) (5 g/L casamino acids, 1.7 g/L yeast nitrogen base, 5 g/L ammonium sulfate, 10.2 g/L $Na_2HPO_4\_7H_2O$ and 8.6 g/L $NaH_2PO_4\_H_2O$, 2% glucose, 15-18 g/L agar, 182 g/L sorbitol) and grown at 30° C. for 2 to 3 days. To confirm each strain, colony PCR followed by sequencing was performed on single colonies. Sequence verified colonies were grown overnight in SD+CAA (5 g/L casamino acids, 1.7 g/L yeast nitrogen base, 5 g/L ammonium sulfate, 10.2 g/L $Na_2HPO_4\_7H_2O$ and 8.6 g/L $NaH_2PO_4\_H_2O$, 2% glucose). The saturated overnight cultures were diluted to a final concentration of 15% glycerol and stored at −80° C.

High-throughput affinity sorting and sequencing To select a diverse pool of ~10,000 unique BH3 sequences for multi-target SORTCERY, we grew the six yeast display libraries described in Jenson et at. and pooled the libraries prior to incubating with 100 nM Bfl-1, Mcl-1, or Bcl-xL(25). Cells were sorted into 12 gates set to separate binders of different affinities, as described by Reich et al. (27). Sorted cells were grown overnight in SD+CAA. An equal number of cells from the Bfl-1, Mcl-1, and Bcl-xL sorts were combined to make a final pool of ~10,000 cells. Of the ~3,333 cells from each sort, most were selected from the highest affinity gate (~540 cells) and the fewest were selected from the lowest affinity gate (~25 cells) with a linear sampling gradient in between. The mixed library was grown overnight and stored in glycerol stocks and used as input for replicate experiments.

To experimentally determine affinities of yeast-displayed peptides for Bfl-1, Mcl-1, and Bcl-xL, we sorted the mixed library into 12 affinity gates and subsequently deep-sequenced DNA from cells collected in each gate following the SORTCERY protocol described in detail by Reich et al. (27).

Yeast cell-surface titrations of peptide standards and designs Affinities for peptides displayed on the surface of yeast were determined by titrating clonal cell populations with increasing protein, measuring the median binding signal for 11

Fluorescence polarization competition binding assay Competition fluorescence polarization experiments were performed as described by Jenson et al. (2S). Experiments were performed in triplicate, using the same protein and peptide preparations, and data were fit as described by Foight et al. (20) to a complete competitive binding model (47).

X-ray crystallography Crystals of Bfl-1 in complex with F4 or F10 were grown in hanging drops over a reservoir containing 1.8 M ammonium sulfate, 0.1 M MES pH 7.0 at room temperature. Peptides in DMSO were mixed with Bfl-1 at equal molar ratio and diluted to 4 mg/ml in 20 mM Tris, 150 mM NaCl, 1% glycerol, 1 mM DTT, pH 8.0. The hanging drops were made by mixing 1.5 μL of complex with 1.5 μL reservoir solution. Crystals were cryo-protected in 2.0 M lithium sulfate with 10% glycerol before flash freezing. Diffraction data were collected at the Advanced Photon Source at the Argonne National Laboratory, NE-CAT beamline 24-ID-C. Both datasets were integrated and scaled to 1.48 Å using HKL2000 and phased using rigid-body refinement of chain A of structure 5UUK in PHENIX(25, 48, 49). The model was refined using PHENIX and COOT(49, 50).

Cell Culture We used murine p185+ $Arf^{-/-}$ B-ALL suspension cell lines with engineered dependencies on the human anti-apoptotic genes (Bfl-1, Mcl-1, Bcl-xL), along with an apoptosis-resistant ($Bax^{-/-}/Bak^{-/-}$) control(51). Cells were grown in Roswell Park Memorial Institute (RPMI) 1640 medium supplemented with 10% (v/v) fetal bovine serum, 2 mM L-glutamine, 100 U/mL penicillin, 100 mg/mL streptomycin, 0.1 mM minimal essential medium nonessential amino acids, 25 mM HEPES and 50 mM β-mercaptoethanol. Cell line authentication was performed by short tandem repeat (STR) analysis. Cell were monitored for mycoplasma contamination using the MycoAlert® Mycoplasma Detection Kit (Lonza, Rockland, Mass., USA).

Cellular BH3 profiling assay BH3 profiling was adapted from the protocol of Ryan and Letai (32). Peptides were diluted at the desired concentrations in MEB buffer (150 mM Mannitol, 10 mM HEPES-KOH pH 7.5, 50 mM KCl, 0.02 mM EGTA, 0.02 mM EDTA, 0.1% BSA and 5 mM succinate) containing 20 mg/mL oligomycin, 50 mg/mL digitonin, 2 mM JC-1 and 10 mM 2-mercaptoethanol in 384-well plates. Controls for no depolarization (1% DMSO) and complete depolarization with the mitochondrial oxidative phosphorylation uncoupler FCCP (10 mM) were included for data normalization. Cells were resuspended at $1.67×10^6$ cells/mL in MEB. 15 μL of cell suspension was added to each well containing 15 μL of treatment solution. Fluorescence emission was measured every 5 min for 3 hr at 590 nM with 525 nM excitation on a Tecan Spark 10M. To produce percent depolarization, the area under the resulting curve was calculated and normalized to the assay controls. The resulting data were plotted as bar graphs showing % depolarization values at the indicated peptide concentrations using Graphpad PRISM 7.

Computational Processing of SORTCERY Data

Filtering sequences for high fidelity reads Deep sequencing datasets were filtered to retain only reads with at least 99% base call accuracy that included the specific multiplex barcodes used to identify each experiment. Paired-end reads that did not overlap were discarded and overlapping paired-end reads were reassembled into a contig. Only unique contigs that had at least 100 reads and that matched a DNA sequence from the designed input library were processed for further analysis.

Generating SORTCERY average affinity coordinates Cell counts for each clone in each of 12 FACS gates were estimated as a function of deep sequencing read counts. To calculate the cell count for sequence x in gate i, $n_i(x)$, we first calculated the clone's frequency in that gate as the number of reads for sequence x in gate i, $r_i(x)$, divided by the sum of all reads for all sequences in gate i. The clone's frequency was then scaled by the observed number of cells recorded to hit gate i in a fixed amount of time, Ci.

$$n_i(x) = \left(\frac{r_i(x)}{\Sigma_{all\_j} r_i(j)}\right) * c_i$$

The probability of finding clone x in gate i is then given by:

$$p_i(x) = \frac{n_i(x)}{\sum_{k=1}^{12} n_k(x)}$$

To mitigate the effects of sequencing error on our analysis, DNA sequences were clustered by sequence similarity using USEARCH with a 3 percent identity cutoff (52). Within each DNA cluster, the sequence with the most reads was assigned as the parent of the cluster and all other sequences were assigned as daughters. Daughter probability distributions over gates were compared to parent profiles. A daughter sequence was split into its own cluster if its probability distribution over gates differed significantly from the parent probability distribution (chi-squared test with Bonferroni correction: alpha-value <0.005/# clones). Otherwise, daughter sequences were combined with parent sequences and each cluster was assigned a new probability distribution profile over gates. The new probability distribution was calculated with the number of reads per gate ($r_i(x)$) set equal to the sum of reads per gate for all sequences in the cluster. Sequences found in only one gate were removed because profiles for individual clones measured independently always span multiple gates. We also removed sequences with non-unimodal profiles using a custom python script that looked for patterns of monotonic increase followed by monotonic decrease.

The probability distribution of cells over gates for each sequence, reconstructed as described above, approximates the distribution of a clonal population of cells along an axis of affinity(26). Profiles were used to compute a mean affinity coordinate, $\overline{A}(x)$, for each sequence x using the equation below, where i is the gate identity.

$$\text{Mean affinity coordinate}(x) = \overline{A}(x) = \sum_{i=1}^{i=12} i \cdot p_i(x)$$

DNA sequences were translated into protein sequences for all subsequent analyses, yielding a list of protein sequences and their associated A(x) values. Eight similarly distributed redundant protein-to-energy mappings originating from synonymous mutation were removed.

Classifying resolvable vs. non-resolvable sequences Peptides were classified as unresolvable tight, resolvable, or unresolvable weak, based on the shape of the probability distribution function for the corresponding display clone across FACS gates. If the mode of the distribution occurred in gate 1, the binder was classified as unresolvable tight. If the mode of the distribution occurred in gate 11 or 12, the binder was classified as unresolvable weak. The remaining sequences were classified as resolvable.

Mapping mean affinity coordinate to ΔG The $\overline{A}(x)$ assigned to each peptide sequence x reflects a relative apparent cell-surface binding affinity, within an experiment, which does not permit comparison across experiments. We used standards to calibrate the affinity axis to report apparent cell-surface binding free energy (here called "binding free energy") in kcal/mol. Standards were selected to span the SORTCERY affinity range of each experiment. For each standard, a binding curve was measured by titrating a clonal population of cells with a target protein and fitting the data to give the apparent standard free energy of binding. We applied linear regression to map $\overline{A}(x)$ values to energies. A linear fit is an approximation of the true relationship between $\overline{A}(x)$ and $\Delta G_{binding}$, as discussed by Reich et al. (equations 8 and 9) (26), but fitting the theoretical curve gave minimal differences in values.

Regression Modeling to Relate Peptide Sequence to $\Delta G_{Binding}$

Protein sequence representation For the linear regression model, we encoded a sequence of length A as a binary vector, with each element of the vector, $x_{i,j}$, reporting whether amino acid j is present at position i.

$$x = [x_{1:1}, x_{1:2}, \ldots, x_{i:j}, \ldots, x_{n:19}, x_{n:20}].$$

The vector has length N*20 where N is the length of the peptide. For a peptide of length 22, as in this work, the encoding is a binary vector of length 440, with 22 non-zero values. In a second-order regression model, the vector must additionally describe all position-residue pair terms. Each pair term is indexed by subscripts i, j, k, and l, where i and k reference the positions and j and l reference the residues in the pair. The binary indicator for a pair of position-residue terms is notated $x_{i:j:k:l}$. The expanded vector is the concatenation of all independent and pair position-residue terms:

$$x = [x_{1:1}, \ldots, x_{i:j}, \ldots, x_{n:20}, x_{1:1:1:1}, \ldots, x_{i:j:k:l}, \ldots, x_{n:20:n:20}].$$

Support vector regression Support vector regression (SVR) models were trained to predict SORTCERY-measured affinity from protein sequence(28). SVR solves for the predicted affinity of sequence i, $\hat{y}_i$, that has at most e deviation from the observed value $y_i$. The predicted affinity for sequence i is defined as the dot product of the weight vector w and the encoded input $x_i$, plus an intercept b: $\hat{y}_i = w^T x_i + b$.

Because this constrained problem does not always have a solution, slack variables ($\zeta_i$) are introduced for each data point and minimized. This results in the primal form of the SVR regression problem, which balances model complexity and performance.

$$\min_{w,b,\zeta,\zeta^*} \frac{1}{2} w^T w + C \sum_{i=1}^{n} (\zeta_i + \zeta_i^*)$$

-continued subject to $y_i - w^T x_i - b \leq \epsilon + \zeta_i$ $w^T x_i + b - y_i \leq \epsilon + \zeta_i^*$ $\zeta_i, \zeta_i^* \geq 0, i = 1, \ldots, n$ The parameter ε defines a range of insensitivity to noise, and the parameter C defines the cost of adding slack to the model. C is a scalar that varies the complexity of the model. Smaller C allows the model to be simpler by permitting more slack during the model optimization. The ε and C parameters for the final models were chosen using nested cross-validation, as described below. SVR was used as implemented in SciKit-Learn.

We tested a linear kernel $x^T z$ and a second order polynomial kernel $(x^T z)^2$ (here x and z are vectors that encode sequences). The polynomial kernel includes contributions from pairs of residues at different positions. This primal optimization problem is solved in the dual form by constructing the Lagrangian objective function(28).

Nested cross validation A generalizability score was determined for linear and second-order models trained on each dataset, using 10-fold nested cross-validation. Each input dataset was split into 10 top-level subsets. Each top-level subset (1/10 of data) was used as a validation dataset (V) that reported the performance of models trained on the remaining 90% of the data (7). The models trained on the datasets T retrieved their hyperparameters from ten-fold cross-validation within the dataset T. Each dataset T was partitioned into 10 parts, where each part, $T_e$, was used to test models trained on the remaining 90% of data in T. A grid of s and C hyperparameters was evaluated on each $T_e$. The combination of C and ε that returned the best average performance across all $T_e$ datasets was used for training a model using all of the data in T. The grid of parameters explored exponential powers of 2 for C between $2^{-14}$-$2^6$, and ε values from 0 to 1, in 0.05 intervals. Ten models trained on 10 different T subsets, each evaluated on a different V subset, gave 10 values that provided an estimate of generalizability. Values reported in FIG. 2, panel a, are the average of the 10 values. The best hyperparameters for the final models, which were trained on all data and then used for landscape mapping and design, were selected as the parameters that performed the best over all of the $T_e$ datasets.

Bcl-2 protein-specific scoring functions The predicted binding energy of a sequence is equal to the dot product of the protein-specific weights determined by SVR (w) and the one-dimensional sequence-encoding binary vector x, plus constant b. The best protein-specific scoring models for Bcl-xL, Mcl-1, and Bfl-1, respectively, were the polynomial models trained using the x1, m1r, and f100 datasets. These energy functions are referred to as X(x), M(x), and F(x), where x is a peptide sequence.

Extracting pairwise weights from second-order polynomial models It is computationally convenient to use a polynomial kernel to solve the SVR problem, when including residue-position pairs. Support vector regression models implemented in Scikit-learn solve the objective function in dual form and return the dual coefficient as a solution to the fitting problem. To extract the pairwise component weights that correspond to the expanded binary vector, including pairs, from the dual coefficient, we applied the following function:

$w = \Sum_{t=1}^m a_t x_t$.

The dual coefficient at reports on the weighted contribution of each sequence, t, to the weight vector (28).

Computational Design by Integer Linear Programming Optimization

Design with integer linear programming We applied integer linear programming (ILP) to solve for the sequence x that maximized or minimized predicted protein binding energies. Constrained-optimization problems were constructed in python and solved with the CPLEX solver via the PulP python library. We pursued six design objectives. Monospecific peptides were designed to bind to Bcl-xL, Mcl-1, or Bfl-1. Bispecific peptides were designed to bind Bcl-xL and Mcl-1, Bcl-xL and Bfl-1, or Mcl-1 and Bfl-1. Peptides were designed to bind selectively to their intended targets by maximizing the target binding affinity (corresponding to minimizing binding energy), maximizing the specificity gap between target and off-target proteins, or minimizing the off-target binding affinity while imposing constraints on target and off-target binding affinities. We also imposed constraints to ensure that the designed sequences had one and only one residue at each position. If a position-residue pair term was included, corresponding position-residue terms were also required to be included. Equations similar to those of Kingsford et al. (53) formalized the constraints applied to enforce design of a valid peptide sequence. To improve the likelihood that the designs would bind to their targets, we restricted designed sequences to only include residues in the input library space used for SORTCERY experiments. We excluded all Cys residues. At positions that were not varied in the libraries used for model development, the design optimization was allowed to select residues from either the Bim or Puma wild-type sequences, which expanded the potential sequence space to the order of $10^{14}$. We also added constraints to prevent inclusion of residues with low confidence weights: The sequence space was restricted to allow only position-residue terms that were observed at least 25 times in all three training datasets. For each design problem, we iteratively identified the 200 best sequences using ILP, from which we selected 7-12 sequences for experimental validation.

Visualizing the Sequence Landscape and Plotting Model Weights

Plotting the binding specificity landscape in 2D The binding energies for sequences with affinity values for Mcl-1, Bfl-1, and Bcl-xL were plotted in a trisected plane to visualize the specificity space. Each peptide is described by 3 vectors, each projecting the negative apparent binding free energy for Mcl-1, Bfl-1, or Bcl-xL, from the origin (0, 0) toward one of three vertices of an equilateral triangle. The Mcl-1 vector extends from (0, 0) to (0, 1). The Bfl-1 vector extends from (0, 0) to (−0.5, sin(120)). The Bcl-xL vector extends from (0, 0) to (−0.5, −sin(120)). The vectors are summed to produce a coordinate in 2D space representing the peptide binding preference for the three proteins.

Input library boundary. The input library is the set of all 27,696,384 possible sequences that could exist in six libraries designed by Jenson et al. (25). After mapping each sequence to an x, y coordinate, we estimated the shape of the boundary by plotting the minimum and maximum y values for the set of sequences binned by the x values rounded to the nearest hundredth of a kcal/mol, and vice versa.

Integrated library boundary The integrated library is the set of all possible sequences that could be created by mixing mutations from all 6 libraries in Jenson et al. (25). We calculated the boundary of specificity for the integrated library space using ILP as follows. For any given peptide, the binding affinities for the three proteins determine the angular and radial coordinate. At any given coordinate, there are two target proteins and an off-target protein. The off-target protein is the one with the lowest binding affinity. The energy gap between the tighter of the two target proteins and the off-target proteins determines the radial position. The affinity ratio between the two targets determines the angular coordinate. For every pair of target proteins, Mcl-1/Bcl-xL, Mcl-1/Bfl-1, and Bcl-xL/Bfl-1, we fixed the energy difference for binding to the two proteins as a constant between −6.8 and 6.8 kcal/mol and solved for the sequence with the lowest off-target affinity via ILP. This optimization problem identified a set of sequences that defines a boundary of specificity. Points plotted on the boundary were additionally constrained by the requirement that each residue at each position had to have been observed a minimum of 25 times.

Input library The libraries used as input to the experiments described here were originally constructed as part of a study by Jenson et al., as noted above. Three libraries were computationally designed to be enriched in peptides specific for binding to either Mcl-1, Bfl-1 or Bcl-xL. The computational design considered the predicted or measured effects of point mutations in Bim BH3 on binding to different Bcl-2 family proteins. The experimental data came from SPOT arrays, and mutational effects were predicted using the structure-based STATIUM statistical model. The choice of which sites to vary, and of which degenerate codons to use at each position, was determined using a computational optimization protocol that eliminated residues predicted to disrupt binding and maximized the number of peptides containing residues predicted to support tight and selective binding. Three different sets of mutations, each designed to promote specificity for either Mcl-1, Bfl-1, or Bcl-xL, were cloned into Bim and PUMA BH3 backgrounds. The resulting six libraries were mixed to make the input library. Even with the computational focusing step, only ~5% of peptides in the input library (with an estimated ~$2 \times 10^7$ members) bound detectably to 100 nM Bfl-1. Therefore, we used the pre-enrichment step described below to identify ~10,000 peptides with a range of binding affinities for target proteins Mcl-1, Bfl-1, and Bcl-xL, and used this smaller pool for amped SORTCERY experiments (see High-throughput affinity sorting and sequencing).

SORTCERY SORTCERY measures the relative binding affinity of peptides displayed on the surface of yeast cells to a target partner protein in solution. The protocol is based on estimating the fraction of yeast cell-surface displayed peptides that are bound to a given concentration of a soluble interaction partner, for thousands of peptides in parallel. The extent of binding is estimated by normalizing the cell-surface binding signal (detected by a set of antibodies) by the cell-surface expression signal (detected by a different set of antibodies). To implement the procedure, a library of peptide-displaying cells is sorted into FACS gates that capture cells with different ratios of binding to expression signals, thus separating cells according to the affinities of their displayed peptides. Deep sequencing of cells from gated pools makes it possible to determine the distribution of each library clone over the pools. Such profiles can be used to compare the binding affinities of different peptides, as described by Reich et al. (3). In this work, we elaborated on this procedure, using the gate profiles to compute a "mean affinity coordinate" for each clone and then using standards to convert the mean affinity coordinates to apparent cell-surface binding affinities.

Model building using Support Vector Regression In this work, amped SORTCERY provided a list of peptide sequences labeled with apparent cell-surface binding affinities. To learn the relationship between sequence and affinity, we used a machine learning procedure to estimate how the presence/absence of different amino-acid residues or residue pairs contributed to the binding affinity of each peptide. Linear regression could be used for this purpose, but naïve regression does not account for noise in the experimental measurements and tends to overfit the training data. As an alternative, support vector regression (SVR) can solve for residue contributions to binding (providing model weights for residues) while also accounting for noise and supporting optimization of the complexity of the model. SVR adds tunable hyperparameters, which balance how sensitive the model is to noise in the data and allow for variation of the complexity of the model, which can improve generalizability (how well the model extends to unobserved data). SVR also permits representation of protein sequence in a way that conveniently captures higher-order terms (here residue-pair contributions) using a polynomial kernel. We previously applied a related approach to train models that describe bZIP coiled-coil interactions (5). More information can be found in an online tutorial at alex.smola.org/papers/2003/SmoSch03b.pdf.

Protein design using integer linear programming Protein design can be framed as optimization of an expression that approximates folding or binding energy as a function of sequence. Given our SVR-derived scoring expressions, we use integer linear programming (ILP) to perform the optimization. One advantage of ILP is that it allows for flexible incorporation of constraints onproperties of the designed sequence. This makes it possible, for example, to identify the sequence that gives the lowest possible energy for binding to target protein X subject to a constraint on the minimum allowed energy for binding to off-target protein Y. Solutions obtained by ILP are provably optimal under the model being used, i.e. an ILP optimization is guaranteed to return the best-scoring sequence, according to the model and subject to the constraints.

Example 2. Computational Design of Peptide Sequences that Selectively Bind Bcl-2 Family Proteins Using dTERM The large number of solved structures now makes it possible to compile a finite, yet near-complete, list of the recurring tertiary structural motifs (here called TERMs) that are needed to construct any protein structure [27]. Recent analyses have demonstrated that TERMs have characteristic sequence preferences that can be detected by statistical analysis of solved structures [28]. Zhou et al. described and extensively benchmarked a TERM-based design method, called dTERMen (design with TERM energies), demonstrating that it is predictive with respect to available data and can generate novel sequences that fold to the intended structure [29]. So far, TERM-based methods have not been applied to predicting or designing protein interactions.

dTERMen is distinct from many other approaches to protein design because it chooses sequences for a target structure based on mining the PDB for TERM-based sequence statistics. These statistics quantify sequence-structure compatibility in the context of ensembles of structurally similar TERMs, as opposed to a single fixed backbone. This approach implicitly accounts for some backbone flexibility, which is advantageous. But building a scoring function from an ensemble of structures also means that design results are not always easy to interpret in the context of a single ground-state structure. For example, steric clashes that are apparent when a designed sequence is modeled in the context of a fixed backbone structure may or may not represent a true problem.

Described in this example is the use of dTERMen to analyze and re-design peptide binders of the important anti-apoptotic proteins Bfl-1 and Mcl-1.

Bcl-2 family proteins Bcl-2, Bcl-xL, Bcl-w, Bfl-1 and Mcl-1 bind to Bcl-2 homology 3 (BH3) motifs within their interaction partners. The short approximately 23-residue BH3 motif, typically disordered in solution, folds into an alpha helix upon binding. Herein, we refer to positions in BH3 peptides using a heptad notation, defined in Table Y1 of native BH3 sequences, that reflects the periodicity of the amphipathic helix. In this notation, positions 2d, 3a, 3d and 4a are typically hydrophobic, position 3a is conserved as leucine in native BH3 motifs, position 3e is conserved as a small amino acid, and position 3f is conserved as aspartate.

TABLE Y1

Native BH3 Sequences and heptad notation

```
          `--|--2---|--3---|--4---`
Name      efgabcdefgabcdefgabcdefg
```

| Name | Sequence | |
|---|---|---|
| PUMA | EQWAREIGAQLRRMADDLNAQYERRR | (SEQ ID NO: 98) |
| BIM | MRPEIWIAQELRRIGDEFNAYYARRV | (SEQ ID NO: 99) |
| NOXA | AELEVECATQLRRFGDKLNFRQKLLN | (SEQ ID NO: 100) |
| BAD | LWAAQRYGRELRRMSDEFVDSFKKGL | (SEQ ID NO: 101) |
| BAK | SSTMGQVGRQLAIIGDDINRRYDSEF | (SEQ ID NO: 102) |
| BAX | DASTKKLSECLKRIGDELDSNMELQR | (SEQ ID NO: 103) |
| HRK | SSAAQLTAARLKALGDELHQRTMWRR | (SEQ ID NO: 104) |
| BMF | HQAEVQIARKLQCIADQFHRLHVQQH | (SEQ ID NO: 105) |
| BIK | MEGSDALALRLACIGDEMDVSLRAPR | (SEQ ID NO: 106) |
| BID | EDIIRNIARHLAQVGDSMDRSIPPGL | (SEQ ID NO: 107) |
| MULE | GVMTQEVGQLLQDMGDDVYQQYRSLT | (SEQ ID NO: 108) |
| BECLIN | GGTMENLSRRLKVTGDLFDIMSGQTD | (SEQ ID NO: 109) |
| BOK | PGRLAEVCAVLLRLGDELEMIRPSVY | (SEQ ID NO: 110) |

We first evaluated the potential of dTERMen for designing peptide ligands for Bcl-2 family targets, we tested its performance on a variety of prediction tasks. We used a dataset consisting of 4488, 4648 and 3948 measurements of BH3 peptides binding to Bcl-xL, Mcl-1 and Bfl-1, respectively. We defined three tasks of increasing difficulty. The easiest task was to discriminate the tightest 20% of binders from the weakest 20%, for a particular target protein. We also defined an enrichment task, which involved identifying the tightest 10% of binders and, finally, the difficult task of predicting quantitative affinities within a 5 kcal/mol range in apparent binding energies. For these tests, we compared the performance of dTERMen with that of commonly used methods Rosetta [41,42] and FoldX [43], After extensive analysis, we determined that dTERMen performed at least as well as established scoring functions in benchmarking leading us to conclude that it might be useful for designing peptide binders. Given a template structure, dTERMen can be used to solve for the optimal sequence to fit on the template, or in this case to fit on the peptide chain in the template given a fixed sequence for the protein target.

We chose 5 structures as design templates: two structures of Bfl-1 complexes and three structures of Mcl-1 complexes. Templates were chosen to sample structural diversity, because distinct templates could potentially provide access to different sequence spaces.

For Bfl-1-targeted designs, we selected structures of Bfl-1 bound to the natural ligand PUMA (PDB ID 5UUL) and of Bfl-1 bound to a Bfl-1 selective peptide (FS2) that was identified in a previously reported screen (PDB ID 5UUK) [36]. Because the backbones of peptides PUMA and FS2 are shifted 1.2 Å and rotated 17° relative to one another in the Bfl-1 binding pocket, we expected to see differences in the optimal sequences identified by dTERMen for these two templates. For the Mcl-1 targeted designs, we used structures of Mcl-1 bound to the natural ligand BIM (PDB ID 2PQK) and to a chemically crosslinked variant of the natural ligand BID, called BID-MM (PDB ID 5C3F) [44,45]. These two binding modes are similar (peptide RMSD=0.76 Å when superimposing the binding interface), but the Mcl-1 protein has differences in the binding pocket in the two structures (binding site RMSD=1.13 Å). We also used a structure of peptide FS2 bound to Mcl-1. FS2 has low affinity for Mcl-1 (Kd >3 µM) but engages the protein in a unique binding pose (PDB ID 5UUM) [36], Peptide sequences were designed on each of the templates 5UUL, 5UUK, 2PQK, and 5C3F using dTERMen. Preliminary calculations showed that the designed sequences with the best dTERMen scores included medium sized hydrophobic residues at 3a and negatively charged residues at 3f, similar to the conserved leucine and aspartate residues in native BH3 motifs. However, dTERMen-design sequences did not preserve native trends at position 4b. Specifically, the 4b position of many native BH3 peptides is often asparagine, aspartate or histidine, which can serve as an N-terminal helix cap for helix 5 of Mcl-1 or Bfl-1. We noticed that dTERMen chose a variety of amino acids at this position (Lys, Glu, Ser, Ala, Val, Tyr, and Thr). To explore the reason behind this departure from the sequence patterns of native BH3 domains, we extracted the N-terminal helix-capping motif (i.e., N-terminus of helix 5 and the BH3 capping fragment) from each template and recovered closely-matching backbone geometries from the PDB. To our surprise, whereas matches made to Bcl-2 family proteins indeed exhibited a strong preference for asparagine or aspartate at the capping position, the frequency of capping residues across other matches were considerably lower (e.g., on average, 6% and 10% for asparagine or aspartate, respectively, in the top ~600 non-Bcl-2 homologous matches). It is therefore not surprising that the apparently strong capping effect in native BH3 helices was not recapitulated in dTERMen designs. While it was unclear whether a capping residue at position 4b would be required or not, we chose to fix this position to either asparagine or aspartate (based on the residue in the design template). BH3 residue 3b can also make a helix-capping interaction. In this case, we imposed the wild-type amino-acid identity in half of the designs (dF1-dF4, dM1-dM4), while allowing this position to vary in the other half (dF5-dF8, dM5-dM7). Two sequences were designed on 5UUM (one for each dTERMen version), without any sequence constraints.

Table Y2 shows the optimal (provably best-scoring) designed peptide sequence for each template structure. For many of the designs, re-packing the protein and peptide sidechains on the rigid-backbone design template using Rosetta showed evidence for predicted steric clashes of varying severity. We used PyMol to visualize regions of possible over-packing. Because some backbone relaxation is expected when designing new protein complexes, and because the dTERMen scoring function predicted that the designed sequences are compatible with structures closely related to the design templates, we did not filter the designs using any kind of clash criterion.

TABLE Y2

BH3 sequences for template structures (bold) and for peptides designed on those templates using dTERMen.

| Name | Sequence<br>---\|--2---\|--3---\|--4---<br>efgabcdefgabcdefgabcdefg | PDB ID | SEQ ID NO: |
|---|---|---|---|
| FS2 | -QWVREIAAGLRRAADDVNAQVE- | 5UUK | 112 |
| dF1 | -SYVDKIADVMREVAEKINSDLT- | | 90 |
| dF2 | -SYIDKIADLIRKVAEEINSKLE- | | 91 |
| dF5 | -SYVDKIADLMKKVAEKINSDLT- | | 113 |
| dF6 | -SYIDKIADLIDKVVEEINSKLE- | | 114 |
| PUMA | -QWAREIGAQLRRMADDLNAQYER | 5UUL | 111 |
| dF3 | -SLLEKLAEELRQLADELNKKFEK | | 115 |
| dF4 | -SLLEKLAEYLRQMADEINKKYVK | | 116 |
| dF7 | -SLLEKLAEELAQLADELNKKFEK | | 117 |
| dF8 | -SLLEKLAEYLAQMGDEINKKYVK | | 118 |
| BIM | GRPEIWIAQELRRIGDEFNAYYA- | 2PQK | 119 |
| dM1 | APKEKEVAETLRKIGEEINEALK- | | 120 |
| dM2 | APYLEQVARTLRKIGEEINEALR- | | 121 |
| dM5 | APKEKEVARTLIKIGEEINEALK- | | 122 |
| dM6 | APYLEQVARTLLHIGMEINEALR- | | 123 |
| BID | EDIIRNIARHLABVGDBBDRSI-- | 5C3F | 124 |
| dM3 | DKTLEEIARELAKLAEEIDKEI-- | | 125 |
| dM4 | DKTLEEIARWLARLALEIDKEI-- | | 126 |
| dM7 | DKTLEEIARELLKLALEIDKEI-- | | 127 |
| FS2 | -QWVREIAAGLRRAADDVNAQVER | 5UUM | 128 |
| dM9 | -DIEQEIAEALKEVADELSKAIED | | 129 |
| dM10 | -DVVLSVAETLRELADRLYEEINT | | 87 |

B = Norleucine

FIG. 5, panel A, shows sequence logos built from 1000 sequences designed on each template, generated from a Monte Carlo simulation (see Methods). These data, and the designed sequences in Table Y2, confirm that peptides designed on different templates were highly distinct, as anticipated. Particularly notable was the diversity observed at positions 3a and 3f. Although dTERMen overwhelmingly chose leucine at position 3a for peptides designed on template 5C3F, matching the conservation observed in native BH3 sequences, greater sequence variation was observed at this site in designs based on other templates. For example, designs based on structure 5UUK included isoleucine or methionine more often than leucine. Position 3f is conserved as aspartate in the natural sequences, but dTERMen chose a variety of polar residues at this site for all templates.

To evaluate the predictions made by dTERMen, 17 out of the 18 designed peptides in Table 3 were selected for experimental testing. Sequence dM8, designed on template 5C3F, was not tested because it was only one mutation away from design dM7. The sequences chosen for testing, like all sequences resulting from the design protocol, were very different from any previously known BH3 sequences. FIG. 5, panel b, summarizes the minimum number of mutations between the peptides we tested and any of the 13 native BH3 sequences in Table Y1. Designed peptide binding to Bfl-1, Mcl-1, Bcl-xL, Bcl-w, and Bcl-2 was assayed by yeast-surface display. Binding data from yeast-surface display assays have been shown to correlate well with solution affinity measurements, and many BH3 peptides that are tight binders on the yeast cell surface have also been validated as high-affinity binders in solution [35,46,47]. 7 out of 8 peptides designed to bind Bfl-1 gave strong binding signal at 100 nM Bfl-1, and 8 of 9 sequences designed to bind Mcl-1 gave similarly strong signal at 100 nM Mcl-1 (FIG. 5, panel d and panel e). The results show that constraints on the helix-capping residues at positions 3b and 4b were not necessary for the designed peptides to bind their targets tightly. Peptides designed based on the 5UUM template, a structure of Mcl-1 bound to low-affinity ligand FS2, bound approximately 100-fold more tightly than did FS2 itself, supporting dTERMen as a way to improve the affinity of initial leads for which structures are available.

Peptides dF6 and dM6 did not bind to their targets with high affinity. Peptide dF6 has a valine at position 3e, which is conserved as small (Ala or Gly) in native BH3 peptides, in previously reported designed peptides, and in all of the other dTERMen-designed peptides that we tested [47-49], Structural matches identified by dTERMen as part of the design process suggested that valine could be accommodated in the context of helix-helix interface geometries highly similar to the one in 5UUK between Bfl-1 residue 88 and BH3 position 3e. In fact, the second closest match to this local interfacial geometry in our database (backbone RMSD of only 0.27 Å) harbors a valine. Nevertheless, an all-atom model built using template 5UUK highlights clashes due to the close proximity of the Cα atom of dF6 position 3e and the backbone of position 88 in helix 5 of Bfl-1, and valine may be too large to be accommodated at this site. For design dM6, we hypothesize that the substitution of arginine and aspartate at positions 3b and 3f of BIM with leucine and methionine, respectively, and concomitant disruption of a charged network between the peptide and the protein, was destabilizing. These features are consistent with dM6 not binding to any of the Bcl-2 family members we tested (see below).

There is substantial interest in developing Bcl-2 family paralog selective inhibitors [8,31,35,49]. To determine whether our designs cross-react with other anti-apoptotic family members, we tested binding of each peptide to Bfl-1, Mcl-1, Bcl-xL, Bcl-w, and Bcl-2. Interestingly, the Bfl-1 binders that were designed on the structure of PUMA in complex with Bfl-1 (5UUL) bound to multiple Bcl-2 family members. In contrast, peptides designed on 5UUK, which is the structure of Bfl-1-specific peptide FS2 bound to Bfl-1, were >100-fold selective for Bfl-1, like FS2 itself. The data were less clear for Mcl-1 binders, some of which were selective (dM1, dM5) whereas others were not (dM2, dM3, dM4, dM7, dM9, dM10).

To determine whether the designed peptides maintained the binding mode of the templates they were designed on, we solved crystal structures for four of the peptides that bound tightly to their targets: dF1 and dF4 in complex with Bfl-1, and dM1 and dM7 in complex with Mcl-1 (FIG. 6). The structure of dF1 in complex with Bfl-1, resolved to 1.58

Å, shows that this peptide binds very similarly to FS2 in template 5UUK (FIG. 6, panel a). It is striking how similar the pocket-facing positions of the designed peptide dF1 and template peptide FS2 are, even though the sequence identity of these two peptides is low (27%) and no information about the FS2 sequence was used in the design process.

Modeling dF1 onto the FS2 backbone in structure 5UUK indicated minor clashes, including between methionine at position 3a and residues in the P2 pocket of Bfl-1 (Met 75, Phe 95, and Glu 78), isoleucine at position 4a with Val 44 in helix 2 of Bfl-1, and valine at position 3d with Val 48 and Val 44 of helix 2 of Bfl-1. A more substantial clash was anticipated between valine at position 2g and Leu 52 of helix 2 of Bfl-1. The crystal structure of dF1 bound to Bfl-1 shows how small adjustments accommodate these residues. For example, in the region around valine at 2g, small backbone adjustments are seen for Bfl-1 residues 50-63 that make room for this residue and lead to a modest divergence of the N-terminus of FS2 in 5UUK compared to dF1 in our new structure (FIG. 6, panel a).

We solved the structure of dF4 bound to Bfl-1 to 1.75 Å and found that the C-terminal end of the peptide adopts a different conformation than does PUMA BH3 bound to Bfl-1 in structure 5UUL (FIG. 6, panel b). In template 5UUL, the helix begins to unwind around position 4d, but in the redesigned structure the helix unwinds 3 residues earlier. dTERMen identified relatively few matches for structural elements at the C-terminus of 5UUL, which may have contributed to the deviation from the design template. At the N-terminus, the sequence of dF4 is very different from that of PUMA; there is only one identical residue within the first 10 residues. An important change was glycine (in PUMA) to alanine (in dF4) at position 2e. In 5UUL, this site is located at a tightly packed helix-helix crossing. Although only glycine can fit when modeled on the rigid design template, TERM statistics indicated that alanine is common in very similar geometries. The solved structure shows how the dF4 helix shifts slightly to accommodate alanine, along with other sequence changes.

We solved the structure of dM1 bound to Mcl-1 to 1.95 Å and found that that it bound very similarly to the BIM BH3 peptide in design template 2PQK (FIG. 6, panel 6). However, the structure of dM7 bound to Mcl-1 at 2.25 Å resolution revealed a substantial change in the binding mode of the peptide (FIG. 6, panel d). The helix is shifted in the groove by 3.43 Å and rotated by 19 degrees along the helix axis, relative to the position of BID-MM in the design template structure 5C3F. A shift of the helix in the groove by approximately one-half helical turn re-positions leucine at 3a relative to what is observed in structures of native BH3 peptides bound to Bcl-2 family proteins. Furthermore, the canonical BH3 interaction of aspartate at 3f with Bfl-1 Arg 263 is replaced by a salt bridge with an aspartate at position 4b in the peptide. In Mcl-1, alpha helix 4 is rearranged relative to its position in the template, to accommodate the unusual sequence. The reorganization may have resulted from introducing two leucine residues at peptide positions 3b and 3f. Not only does leucine at 3f remove the aspartate residue at this position in BIM, BID and PUMA, but leucine at 3b is predicted to interfere with an intra-molecular salt bridge between Bfl-1 residues 256 and 263. The shift of peptide dF1 observed in the crystal structure restores the salt-bridge network between Bfl-1 and the peptide, using a different peptide residue. One complication in evaluating this structure is that there are close contacts between two copies of the Mcl-1:dM7 complex, near the C-terminal end of the binding groove, and involving alpha helix 4 of Mcl-1.

We cannot rule out the possibility that crystal packing forces favored population of a minor structural species, and that the designed binding mode may be populated in solution.

In summary, x-ray crystallography revealed that backbone positioning of two of the crystalized designs (dF1 and dM1) were sub-Angstrom matches to their design templates, over most of the length of the peptide. Another peptide (dF4) bound in a geometry that shared high similarity with its template, but the remaining design (dM7) bound in an unexpected, dramatically shifted orientation.

Using dTERMen, we were able to rapidly design high-affinity binders of Bcl-2 family proteins without the need for explicit modeling of complex structures or expensive experimental library screening. Previous work has shown that this is not a trivial task. For example, in a library of random peptides, nearly all fail to bind Mcl-1 detectably [50]. Additionally, even in carefully designed libraries containing peptides with fewer than 6-8 mutations compared to natural BH3 domains, most sequences fail to bind Bfl-1 and Mcl-1 [36], In contrast, using dTERMen, we found that 15/17 of the designs bound with native-like affinity, even though the sequences were 14-22 mutations away from known BH3 binders (FIG. 5, panel b and panel c).

Our design protocol provided access to novel and diverse sequences. Some of the tight binders we discovered using dTERMen lack the highly conserved leucine and aspartate residues common to all known, native BH3 sequences (Table Y2 and FIG. 5, panel a). Not only do our results suggest that these residues are not necessary for binding, but they show that dTERMen is a useful tool for discovering binders that cannot be predicted based on conserved sequence features. Designing on different structural templates gave rise to different solutions, as illustrated in FIG. 5, panel a. This may seem to be at odds with our finding that dTERMen is robust to small differences in input structure, but we deliberately chose design templates to sample different peptide docking geometries. We expected these templates to match with different TERMs from the PDB, and thus to generate different sequence predictions. Templates 5UUL and 2PQK are structures of complexes with native, tight BH3 peptide binders (reported dissociation constants of 1 nM) [36,44], Other templates we tested, 5C3F and 5UUM, featured peptides that bound their targets more than 3 orders of magnitude more weakly [36,45], It is notable that template structures for both high-affinity and low-affinity peptide complexes led to novel, high-affinity peptide binders when used as input to dTERMen. Designing on other solved structures could provide access to even greater diversity. Going beyond solved structures, it may be possible to perform dTERMen design on predicted structures with binding modes that have not been previously observed.

A set of designs with diverse sequences is more valuable that a single design optimized for affinity because it provides opportunities to optimize pharmacological properties not related to binding. Our designed peptides have formal net charges ranging from −7 to +1, predicted helical content ranging from 0.7 to 69.7% and predicted hydrophobicity of 0.03 to 0.48 (S5 Table). These properties could affect whether these peptides are disruptive to membranes and how readily they can be delivered to cells. Several studies have shown that the cell permeability of stapled helical peptides depends on peptide properties including charge and hydrophobicity [8,10], Different sequences will also have different cross-reactivity, immunogenicity, and protease sensitivity, so having many options to choose from increases the chances of developing useful reagents and lead therapeutics. Interestingly, design using dTERMen is compatible with imposing constraints on peptide properties such as net charge, so if the desired physical characteristics of a peptide inhibitor are known, they can be used to direct the search into promising sequence spaces.

The dTERMen scoring potential is based on sequence statistics for structural elements observed repeatedly in nature. There is no formal relationship between these statistics and protein stability or affinity, so the scoring may reflect any number of evolutionary pressures including stability, specificity, folding kinetics, solubility, or other factors. We interpret the success of dTERMen as evidence that whatever evolutionary forces may be contributing to the statistics, there must be a substantial contribution from the free energy of the sequence adopting the evaluated structure. The fact that we designed helix-helix interactions in this project, which are common in the PDB, may be part of the reason dTERMen designs performed so well. Because more structures are deposited in the PDB every day, we expect the range of accessible design targets to increase over time [28].

One attractive feature of dTERMen is that it does not require explicit structural modeling or minimization; the design optimization is performed in sequence space. Although the PDB structure-mining that is required to build the scoring function can be somewhat time consuming (e.g. it takes 7 to 12 CPU hours to generate scoring functions for the structures we analyzed here), once such a function is derived, it is possible to perform design, or to evaluate millions of sequences, in seconds. Another advantage of dTERMen is that there is a structural "fuzziness" built in, because the sequence statistics used for modeling are derived from close, but not exact, matches of TERMs. This makes the method more robust than FoldX to small variations in input structure, as shown in our benchmark testing, and also accounts for some amount of backbone relaxation. In this work, we observed multiple examples where a mutation was accommodated that would not have been designed if modeling was performed on a rigid scaffold. On the other hand, dTERMen design failures may result from over-packing the protein-peptide interface beyond what can be accommodated by small structural rearrangements. This may be what happened for dF4, the structure of which diverged from the design template structure at the C-terminal end of the peptide, and for dF6, which did not bind tightly to Bfl-1. Future design studies will help calibrate the methods so that diverse sequences can be obtained with reliably high success rates. Combining dTERMen with a post-analysis procedure that includes all-atom modeling with aggressive conformational search, using peptide relocking [51] or MD simulation [52], could be one way to recognize sequences or mutations that can or cannot be accommodated. Although this would increase the computational costs, such a secondary evaluation could be performed for a modest number of promising candidates designs.

One unexpected result from this work is that the specificity profiles of the designs were template dependent. This is particularly striking in the case of design on the FS2 template. Although no off targets were considered during design, the peptides designed using the FS2 structure were highly Bfl-1 selective. In fact, these peptides provide outstanding leads for development as Bfl-1 targeting agents. The specificity of peptides dF1, dF2 and dF5 may be a result of the unique way FS2 engages Bfl-1. FS2 adopts a non-canonical binding mode that has not been observed for natural BH3 ligands [36]. It may be that the interactions with Bfl-1 that support the FS2 binding mode are under less evolutionary pressure to mirror those required for BH3 binding in the other family members, and are thus more likely to be unique. This is consistent with the idea that a peptide that makes contacts outside of the conserved binding cleft can use these contacts to achieve intra-family specificity [37,53].

This proof-of-principle study makes us enormously enthusiastic about the potential of dTERMen for designing peptide binders and inhibitors. The ease of use, fast run times, and very high success rates on a difficult problem provide compelling evidence of the promise of this approach. Future applications could exploit dTERMen scoring speed by screening proteomes to predict candidate binding partners, or could leverage the robustness of dTERMen to scaffold variation by designing on low resolution structures. There are ample opportunities to improve dTERMen further, for example by combining this sequence-based design approach with all-atom modeling to better assess what mutations can be accommodated by structural relaxation. We look forward to tackling increasingly difficult problems and moving the use of TERM statistics into the mainstream of modem protein design.

Methods dTERMen design scoring function A full description of the dTERMen procedure, along with extensive validation and benchmarking, is given in Zhou et al. [29], For completeness, we briefly outline the method here, at a high level. Given a target protein structure, D, for which an appropriate amino-acid sequence is needed, dTERMen begins by defining effective self energies for each amino acid at each position of D and effective pair interaction energies between amino acids at pairs of positions. We collectively refer to these as energy parameters (EPs) and their values in our procedure are deduced from statistics of structural matches to appropriately defined TERMs that make up D. The matches are obtained by searching a structural database. In this work, the database was a subset of the PDB containing 14,546 chains from X-ray structures with resolution better than 2.6 Å, pruned for redundancy at 30% sequence identity. Importantly, this means there was no quaternary structural information present in the database, and all insights on how to design domain-peptide interfaces were derived from intra-chain examples.

The fundamental idea behind our procedure is to define TERMs from D in a way that is targeted at isolating individual EP contributions. For example, to capture the pairwise dependence between amino-acid identities at positions i and j (i.e., the pair EP), we define a TERM that consists of residues i,j, and their surrounding backbone fragments (e.g., ±2 residues around each residue). By obtaining a sufficiently large list of closest matches to the generated motif (pruned for redundancy), one can analyze the co-dependence between identities at i and j. One complicating factor is that identities at the two positions are also biased by the specific environments from which the matches originate. And, in some cases, this bias could affect the apparent co-dependence. E.g., if the two positions are usually either both buried or both exposed within matches, it may appear that there is a direct favorable interaction between amino acids of similar hydrophobicity at i and j. Such effects are corrected for in dTERMen by computing EPs as log-odds ratios between observed and expected numbers of observations (e.g., observations of amino-acid pairs in this case), where the expectation is calculated by accounting for the effect of the environment in the structures from which matches originate. Self-EP contributions arising from interactions between a residue and nearby backbone fragments are computed similarly. These include interactions with both the local sequence-contiguous backbone (the own-backbone energy) and backbone fragments proximal in 3D (the near-backbone energy). These contributions augment pre-tabulated amino-acid self-energies associated with different backbone φ/Ψ and ω dihedral angles and burial states to form the final EP contributions.

The above computed contributions are compiled into an energy table of one- and two-body contributions, after which Integer Linear Programing (ILP) is used to identify the sequence with the most optimal score [54,55], Note that all energies are defined on the sequence level, such that optimization can proceed directly in sequence space, without the need to build explicit atomic structures. And yet, because each EP contribution arises from an ensemble of TERM matches, a certain amount of implicit backbone flexibility is built into the scoring function.

dTERMen sequence design protocol When the design problem pre-specifies some of the residues in the target structure D, as is the case in the present application, the calculations remain the same but some re-shuffling between pair and self EPs takes place. For example, when position i in an interacting pair i-j is fixed, the TERM-derived effective pair EP between the two is added to the self-energy of position j in the final table. Because in the present case the sequence of the entire domain was always fixed, the only pairwise contributions in the final table were those between pairs of peptide positions.

The two versions of dTERMen used here differ in how TERMs for computing the near-backbone energy for residue i are defined (see Zhou et al. for full details [29]). The ideal TERM for this purpose would include the residue i, its local backbone fragment, all residues with the potential to interact with i (through either side-chain or backbone—i.e., influencing residues), and their respective local backbone fragments. If such a TERM has a sufficient number of close structural matches in the database, then this definition works well and the two dTERMen versions will both pick this motif (producing the same result). Because near-backbone TERMs can have many segments (e.g., three potential interacting positions would give rise to a four-segment TERM), they may not always be represented well enough in the database to derive confident sequence statistics on the amino-acid preferences at i. In this case, one is forced to consider the effect of the local backbone geometry on position i as an aggregate of effects from sub-motifs, and the two versions deal with this differently. Version attempts to identify large sub-motifs, each consisting of i and as many of the influencing residues as possible (along with local backbones), such that sub-motifs do not overlap and together cover all influencing residues. This takes a considerable amount of database searching, as many trial sub-motifs have to be queried. Version 34 speeds this process up, at the cost of some detail, by considering just one sub-motif that includes the most "important" influencing residues (assessed via our geometric measure of contact degree [30]), on the assumption that this motif dominates sequence statistics.

Structural model generation We used pyRosetta [56] (Linux release r53335) to generate structural models for dTERMen-designed sequences emergent from ILP optimization. This was done by performing fixed-backbone side-chain repacking of all residues in the domain-peptide complex (peptide residues taken from the dTERMen-optimized sequence) using the talaris2013 forcefield [56] and default parameters in pyRosetta via "standard_packer_task" and "PackRotamersMover" objects. For residues where there was evidence of crowding, all backbone-dependent rotamers of a residue of interest were manually inspected using PyMol. S3-S6 Figs were made by choosing the least clashing rotamer.

Sequence logo generation In addition to obtaining the dTERMen-optimal sequence for each template by ILP, we also performed Monte Carlo (MC) sampling to generate an ensemble of well-scoring sequences as a way of better characterizing the predicted favorable sequence space (see FIG. 2A). To this end, we ran 1,000 independent MC trajectories for each template starting with a random sequence. Each trajectory involved 100,000 iterations, at each of which a random mutation was evaluated for acceptance according to the Metropolis criterion. The sampling was performed at constant temperature with kT equal to 1 (this was also the temperature used to derive dTERMen statistical energies). The final accepted sequence from each of the 1,000 trajectories was used to build an MSA for each template and to generate the logos in FIG. 2A using WebLogo [57], Designed-peptides property prediction Predicted helical content for designed peptides was obtained from the AGADIR web server [58]. Predicted net charges and hydrophobicity were obtained using the HelixQuest server [59].

Analysis of similarity of peptide interactions with Bcl-2 family paralogs The Bfl-1 sequence was aligned with the sequences of Bcl-xL, Mcl-1, Bcl-2, and Bcl-w using ClustalW [60], Each residue in Bfl-1 was scored for sequence similarity to the corresponding residue in each of the other proteins using the Blosum62 matrix [61]. Substitutions with scores ≥0 were considered similar. To display amino-acid conservation at each position on the Bfl-1 structure each residue was colored by the number of proteins with amino acids similar to the one in Bfl-1 at that position.

Automatic download and annotation of Bcl-2 protein-peptide complex structures Uniprot sequences for human Bcl-xL, Bfl-1 and Mcl-1 were retrieved from Uniprot [62] and blasted against the PDB database [63] (7 Nov. 2017). Matched structures were downloaded and standardised by transforming selenomethionine to methionine and removing hydrogens and atoms designated as HETATOM. Sequences were aligned and renumbered based on their corresponding Uniprot template sequence using Needle [64], Regions that were not matched or that were poorly aligned with the Uniprot sequence were removed from the structure. Chains of length 20-39 residues with more than 30% of their Voronoi surface in contact with the Bcl-2 proteins were identified as interacting peptide [65]. Unless specified, peptides containing non-natural amino acids were removed from the dataset. Only the first model in deposited NMR ensembles was retained. If a structure included multiple complexes in the asymmetric unit, these were split into new files and analyzed separately.

Alignment on the Binding Site and Method for Comparing Peptide Binding Geometry

For every complex, residues within 8 Å of any peptide atom were considered part of the binding interface and all complexes were structurally aligned using only their binding interface Cα atoms, using 3DCOMB [66], To automatically define a common reference residue for all bound peptides, we used a graph-based procedure. Each peptide Cα in the set of superimposed binding interfaces was represented as a node, and an edge was created if the distance between 2 nodes was below a threshold. The distance threshold was initially set at 2 Å and gradually increased by 0.1 Å until the largest clique in the graph included one residue from each complex. This clique represented a set of $C_\alpha$ atoms—one in each structure—all within a distance threshold. Residues in this largest clique were arbitrarily given peptide residue number 100; this reference residue corresponds to residue 95 in structure 3FDL. Using this registry, peptides were trimmed to generate a 20-residue long segment chosen by structural inspection to include positions that make extensive contacts with the protein and that are unlikely to be influenced by crystal contacts in the templates used for modeling. This region corresponds to peptide positions 86 to 105 in structure 3FDL. Structures without a complete 20-mer peptide were not used. Binding interfaces were redefined using trimmed peptides, by taking all peptide atoms plus protein residues within 8 Å of any peptide atom.

Scoring Protein-Peptide Interactions

Structural scoring functions dTERMen (described above), FoldX4.0 and Rosetta were tested for their ability to predict peptide-protein binding affinity using binding data obtained using the SORTCERY protocol [39,41-43], Scoring was based on trimmed-peptides structures. Each structure was used as a template input for dTERMen, leading to a scoring function for that template, i.e. a function that can score any peptide binding to the target protein in the template-structure binding mode. FoldX4.0 was used to predict binding affinity by first using FoldX4.0's "repair" function. Then, for each peptide in the SORTCERY dataset, the repaired template was transformed using the "mutate" function to generate the sequence of the peptide query and scored using the "complex" function. For Rosetta scoring, complex structures generated by FoldX were relaxed with Rosetta (November 2017 version rosetta_bin_linux_2017.08.59291, "relax" command) using Talaris2014 or BetaNov force fields [42], The default parameters of 5 minimization cycles consisting of 4 rounds of repacking were used for the relaxation protocol. Relaxed structures were run through the Rosetta InterfaceAnalyzer module, and the "dG_separated" values were used as the predicted binding energy. This score describes the difference in Rosetta energy of interface residues between the complex structure and corresponding separated chains. For the sake of simplicity in the reporting of benchmarking results, only the latest scoring function of Rosetta (BetaNov) and dTERMen (35) are discussed. dTERMen scoring function 34 and Rosetta Talaris2014 force field yield similar benchmark performance as these newer versions and values can be found in the supplementary table.

Interaction Prediction Benchmark

The predictive power of the different structural scoring functions and protocols was assessed by three metrics. First, each method's ability to discriminate the top 20% tightest-binding peptides from the 20% weakest binders was assessed by calculating Area Under the Curve (AUC) of the Receiver operating characteristic (ROC) curve. Next, precision was evaluated by calculating the correlation between the binding energy determined by SORTCERY, in kcal/mol, and each method's predicted binding energy (in arbitrary units). Finally, we computed the percentage of the top 10% of binders from SORTCERY experiments that were found in the top 10% of predicted binders. Multiple templates were tested for each protein, and predictive power was evaluated for each template individually. The average performance and standard deviation of performance over all templates was computed and represents the expected value if a random template is chosen. We also report prediction performance using the template that gave the lowest energy for each sequence.

Protein and Peptide Purification

Myc-tagged human Mcl-1 (residues 172-327), Bfl-1 (residues 1-151), Bcl-2 (residues 1-217), Bcl-w (residues 1-164), and Bcl-xL (residues 1-209) were used for binding assays. Untagged Bfl-1 (residues 1-151) and Mcl-1 (residues 172-327) were used for crystallography. The proteins used in this study were purified as previously described[47] and frozen at −80° C. The peptides used for crystallography were synthesized at the MIT biopolymers facility with N-terminal acetylation and C-terminal amidation and were purified by HPLC on a C-18 column with a linear gradient of acetonitrile and water. Purified peptides were lyophilized and resuspended in DMSO. Peptide masses were confirmed by MALDI-TOF mass spectrometric analysis.

Yeast Clones

EBY100 yeast cells were transformed using the Frozen-EZ Yeast Transformation II Kit (Zymo Research) according to the manufacturer's protocol. For a plasmid backbone, we used the PUMA PCT plasmid[36] and digested it with XhoI (NEB) and NheI-HF (NEB) according to the manufacturer's protocol. The inserts were constructed by PCR using primers that encoded the peptide sequence flanked with at least 40 bp of the plasmid sequence on either side of the insertion site to facilitate homologous recombination. The inserts and plasmid backbones were mixed at a 5 to 1 ratio for transformation. The transformation mixture was spread onto SD+CAA plates (5 g/L casamino acids, 1.7 g/L yeast nitrogen base, 5 g/L ammonium sulfate, 10.2 g/L $Na_2HPO_4 \cdot 7H_2O$ and 8.6 g/L $NaH_2PO_4 \cdot H_2O$, 2% glucose, 15-18 g/L agar, 182 g/L sorbitol) and grown at 30° C. for 2 to 3 days. To confirm each strain, colony PCR followed by sequencing was performed on single colonies. Sequence verified colonies were grown overnight in SD+CAA (5 g/L casamino acids, 1.7 g/L yeast nitrogen base, 5 g/L ammonium sulfate, 10.2 g/L $Na_2HPO_4 \cdot 7H_2O$ and 8.6 g/L $NaH_2PO_4 \cdot H_2O$, 2% glucose). The saturated overnight cultures were diluted with 40% glycerol to a final glycerol concentration of 15% and stored at −80° C.

Yeast growth and FACS analysis A small amount of frozen culture was scraped from the top of frozen culture stocks to inoculate SD+CAA. After passaging overnight at 30° C., cultures were diluted to an OD600 of 0.005-0.01 in SD+CAA and grown to an OD600 of 0.1-0.6. Cell cultures were then diluted 25-fold with SG+CAA (5 g/L casamino acids, 1.7 g/L yeast nitrogen base, 5.0 g/L ammonium sulfate, 10.2 g/L $Na_2HPO_4 \cdot 7H_2O$ and 8.6 g/L $NaH_2PO_4 \cdot H_2O$, 2% galactose) to induce peptide expression and grown for 20-24 hr at 30° C. To measure binding to surface-displayed peptides, cells were filtered with a 96-well plate filter ($10^5$-$10^6$ cells/well), washed twice with 150 μL BSS (50 mM Tris pH 8, 100 mM NaCl, 1 mg/ml BSA), and resuspended in BSS with least 10-fold molar excess target protein and incubated in the filter plate for 2 h at room temperature with gentle shaking for equilibration. Binding of the designs to the five Bcl-2 family proteins was measured tested at 1000 nM, 100 nM, 10 nM, and 1 nM target protein. To detect cell surface expression and binding of target protein, cell suspensions were filtered, washed twice in chilled BSS, resuspended in a 35 μL of 1:100 dilution of primary antibodies (mouse anti-HA, Roche, RRID: AB_514505 and rabbit anti-c-myc antibodies, Sigma, RRID:AB_439680) in BSS and with gentle shaking for 15 min at 4° C. Cells were then filtered, washed twice in 150 μL chilled BSS, resuspended in 35 μL of a solution of secondary antibodies in BSS (1:40 dilution of APC rat anti-mouse, BD, RRID:AB_398465 and 1:100 dilution of PE goat anti-rabbit, Sigma, RRID:AB_261257) and incubated with gentle shaking in the dark for 15 min at 4° C. Cells were filtered and washed twice more in 150 μL chilled BSS to remove unbound antibodies. Labeled cells were resuspended in BSS and analysed using a BD FACSCanto with FACSDiva software.

Crystallography Crystals of Bfl-1 in complex with the designed peptides were grown in hanging drops. To set the drops, untagged Bfl-1 (8 mg/mL in 20 mM Tris, 150 mM NaCl, 1% glycerol, 1 mM DTT, pH 8.0) was mixed in equal molar ratio with the designed peptides. 1.5 µL of the Bfl-1/peptide mixture was pipetted onto a glass coverslip and mixed with 1.5 µL of well solution (1.8-2.0 M $NH_4SO_4$, 50 mM MES pH 6.5). To cryoprotect the crystals, they were transferred into a solution of 2.0 M $LiSO_4$ with 10% glycerol. Crystals were flash frozen in liquid nitrogen. Diffraction data were collected at the Advanced Photon Source at the Argonne National Laboratory, NE-CAT beamline 24-ID-C. The datasets were refined to 1.59 Å and 1.75 Å and scaled using HKL2000 [67], Phenix was used to phase with the Bfl-1 chain from PDB id 5UUK [36,68]. The peptides were modeled into the difference densities using Coot [69], Iterative rounds of refinement and model building were performed using Phenix and Coot [68,69], Crystals of Mc1-1 in complex with the designed peptides were grown in hanging drops. To set the drops, TCEP (100 mM) and $ZnSO_4$ (50 mM) was added at 10% volume to untagged Mcl-1 (8.5 mg/mL in 20 mM Tris, 150 mM NaCl, 1% glycerol, 1 mM DTT, pH 8.0) before adding equal molar amounts of the designed peptides. To grow crystals of Mcl-1 in complex with dF1, 1.5 µL of the peptide protein mixture was mixed with 1.5 µL of well solution (25% PEG 3350, 50 mM BIS-Tris pH 8.5, 50 mM $NH_4CH_3CO_2$). Crystals were cryoprotected by adding 3 µL of a solution of 37.5% glucose in 25% PEG 3350, 50 mM BIS-Tris pH 8.5, 50 mM $NH_4CH_3CO_2$ directly to the drop 0.5 uL at a time. To grow crystals of Mcl-1 in complex with dF7, 2.5 µL of the peptide protein mixture was mixed with 0.5 µL of well solution (1.4 M sodium citrate pH 6.5, 0.1 M HEPES pH 7.5). For cryoprotection, crystals were transferred to 1.6 M sodium citrate pH 6.5, 0.1 M HEPES pH 7.5. Crystals were flash frozen in liquid nitrogen. Diffraction data were collected at the MIT x-ray core facility. The datasets were refined to 1.95 Å and 2.25 Å and scaled using HKL2000[67], Phenix was used to phase with the Mcl-1 chain from PDB ID 3PK1 [68,70], The peptides were modeled into the difference densities using Coot[69]. Iterative rounds of refinement and model building were performed using Phenix and Coot[68, 69].

Example 3. BH3 Profiling & Results

A whole-cell BH3 profiling assay was used to test the specificity of the peptide constructs in several cell lines with known dependencies on anti-apoptotic proteins, including Bcl-1. Mcl-1, Bcl-xL, or Bfl-1. The creation and characterization of the BCR-ABL-expressing B-lineage acute lymphoblastic leukemia suspension cell lines with engineered dependencies on human versions of anti-apoptotic genes is detailed in Koss et al. [51]. Cells were grown in RPMI (Life Technologies, Carlsbad, Calif.) with 10% fetal bovine serum, 2 mMLglutamine, 10 mL/L 100× Pen/Strep (Life Technologies #15140122), 25 mM HEPES and 10 mL/L 100×NEAA (Life Technologies, 11140050). The adherent cell lines PC-3 (RRID: CVCL_0035) and SF295 (RRID: CVCL_690) are from the NCI60 panel (Lorenzi et al., 2009) and were grown in RPMI (Life Technologies) with 10% fetal bovine serum, 2 mM L-glutamine and 10 mL/L 100×Pen/Strep (Life Technologies #15140122). Cell line identities were confirmed by STR profiling. The Lookout Mycoplasma PCR detection kit (Sigma) was used to detect mycoplasma infection. Mycoplasma was only detected in the PC-3 cell line, and internal controls were used to account for this phenotype.

Peptides were titrated by serial dilution in MEB buffer (150 mM Mannitol, 10 mM HEPES-KOH, pH 7.5, 50 mM KCl, 0.02 mM EGTA, 0.02 mM EDTA, 0.1% BSA and 5 mM Succinate) containing 20 mg/mL oligomycin, 50 mg/mL digitonin, 2 mM JC-1 and 10 mM 2-mercaptoethanol in 384-well plates. Controls for no depolarization (1% DMSO) and complete depolarization with the mitochondrial oxidative phosphorylation uncoupler FCCP (10 mM) were included for data normalization. Cells were suspended at $1.67 \times 10^6$ cells/mL in MEB. 15 µL of cell suspension was added to each well containing 15 µL of treatment solution. Fluorescence emission was measured every 5 min for 3 h at 590 nM with 525 nM excitation on a Tecan Spark 10M. To produce percent depolarization, the area under the resulting curve was calculated and normalized to the assay controls. The resulting data were plotted as bar graphs showing percentage depolarization values at the indicated peptide concentrations using Graphpad PRISM 7™.

As depicted in FIGS. 7-11, permeabilized cells were contacted with increasing doses of BH3 peptides, ad mitochondria outer membrane permeabilization (MOMP) was monitored using a voltage-sensitive dye (JC-1). The apoptotic sensitivity of BCR-ABL-expressing B-lineage acute lymphoblastic leukemia (B-ALL) cell lines engineered to depend on Bcl-2, Bcl-xL, Mcl-1 or Bfl-1 overexpression for survival. DKO cells were B-ALL cells in which Mcl-1-deletion is rescued by loss of both BAX and BAK. Peptides used in FIGS. 7-11 are listed in Table 9 below.

TABLE 9

Sequences of peptides in FIGS. 7-11.

| Peptide name in application Table X2, Table Y2 | Peptide name in figure | Peptide sequences, all with N-acetylation, C-amidation |
|---|---|---|
|  | BIM | RPEIWIAQELRRIGDEFNAYYAR (SEQ ID NO: 130) |
| Puma | PUMA | EQWAREIGAQLRRMADDLNA (SEQ ID NO: 131) |
|  | PUMA2A | EQWAREIGAQARRMAADLNA (SEQ ID NO: 132) |
|  | MS1 | RPEIWMTQGLRRLGDEINAYYAR (SEQ ID NO: 133) |
|  | M1a | IWBJQGLRRLGDEINAYYARR (SEQ ID NO: 134) (B: norleucine, J: 2-aminoisobutyric acid) |
|  | FS1 | QWVREIAAGLRLAADNVNAQLER (SEQ ID NO: 135) |
| srt.M1 | vM1 | RSELEVVQELVRIGDIVVAYFER (SEQ ID NO: 85) |
| srt.M9 | vM9 | RSQYEVIQELIRIGDIVLAYFER (SEQ ID NO: 86) |
| dM10 | gM10 | DVVLSVAETLRELADRLYEEINT (SEQ ID NO: 87) |
| srt.F4 | vF4 | QRVVHIAAGLRRTGDQLEAYG (SEQ ID NO: 88) |

TABLE 9-continued

Sequences of peptides in FIGS. 7-11.

| Peptide name in application Table X2, Table Y2 | Peptide name in figure | Peptide sequences, all with N-acetylation, C-amidation |
|---|---|---|
| srt.F10 | vF10 | RRVVQIAAGLRRAGDQLEKYG (SEQ ID NO: 89) |
| dF1 | gF1 | SYVDKIADVMREVAEKINSDLT (SEQ ID NO: 90) |
| dF4 | gF4 | SLLEKLAEYLRQMADEINKKYVK (SEQ ID NO: 91) |
| srt.XF02 | XF02 | QRIIWIAAELRRAADELDKQIER (SEQ ID NO: 92) |
| srt.XF03 | XF03 | QRIIWIAAELRRAADQLDAQIER (SEQ ID NO: 93) |
| srt.MF02 | MF02 | RWIDQIAQFLRRIGDHIEKYIER (SEQ ID NO: 94) |
| srt.MF06 | MF06 | RRVDEIAQILRRIGDNVTTYIER (SEQ ID NO: 95) |
| srt.MX01 | MX01 | QWLRWVIAELIRIADEFHAQYER (SEQ ID NO: 96) |
| srt.MX05 | MX05 | QWLRDVVAELARIADEFHAQYER (SEQ ID NO: 97) |

FIG. 7 shows the depolarization of mitochondria induced by designed peptides in four cell lines that depend on ectopic expression of Bcl-1 (FIG. 7A), Bcl-xL (FIG. 7B), Bfl-1 (FIG. 7C), and Mcl-1 (FIG. 7D). Mcl-1 peptides vM1, vM9, and gM10 were compared in the different cell lines. As shown in FIGS. 7A-7D, EC50 values for inducing mitochondrial permeabilization in the engineered cell lines agreed well with trends in binding affinities in Table X3.

Bfl-1 peptides were tested in four cell lines that depend on ectopic expression of Bcl-1 (FIG. 8A), Bcl-xL (FIG. 8B), Bfl-1 (FIG. 8C), and Mcl-1 (FIG. 8D). Bfl-1 peptides vF4, vF10, gF1 were compared in the different cell lines. Table X shows strong binding affinity of F10 and F4 for Bfl-1.

Dual-specific Bcl-xL and Bfl-1 peptides were tested in the cell lines described above (FIGS. 9A-9D). Dual-specific Bcl-xL and Bfl-1 peptides XF02 and XF03 were compared in the different cell lines. XF02 and XF03 were shown to have binding affinity for both Bcl-xL and Bfl-1 in Table X.

FIGS. 10 and 11 shows the MOMP assay for dual-specific Mcl-1 and Bfl-1 peptides and dual-specific Mcl-1 and Bcl-xL peptides, respectively. Results with peptides MF02 and MF06 are shown in FIG. 10 and peptides MX01 and MX05 are shown in FIG. 11. Table X shows that MF02 and MF06 peptides have binding affinity for both Mcl-1 and Bfl-1 and peptides MX01 and MX05 have binding affinity for Mcl-1 and Bcl-xL.

These data demonstrate that the peptides presented in Table 9 promote mitochondrial outer member permeabilization either by binding one of Bcl-1, Bcl-xL, Bfl-1, and Mcl-1, or by binding a combination of either Bcl-xL and Bfl-1, Mcl-1 and Bfl-1, or Mcl-1 and Bcl-xL.

REFERENCES

Set (A)
1. Chen T S, Keating A E (2012) Designing specific protein-protein interactions using computation, experimental library screening, or integrated methods. *Protein Sci* 21(7):949-963.
2. Karanicolas J, Kuhlman B (2009) Computational design of affinity and specificity at protein-protein interfaces. *Curr Opin Struct Biol* 19(4):458-63.
3. Whitehead T A, et al. (2012) Optimization of affinity, specificity and function of designed influenza inhibitors using deep sequencing. *Nat Biotechnol* 30(6):543-8.
4. Shirian J, et al. (2018) Converting a broad matrix metalloproteinase family inhibitor into a specific inhibitor of MMP-9 and MMP-14. *FEBS Lett* 592(7): 1122-1134.
5. Gorelik M, et al. (2016) Inhibition of SCF ubiquitin ligases by engineered ubiquitin variants that target the Cul1 binding site on the Skp1-F-box interface. *Proc Natl Acad Sci USA* 113(13):3527-32.
6. He B, et al. (2018) Compositional Bias in Naïve and Chemically-modified Phage-Displayed Libraries uncovered by Paired-end Deep Sequencing. *Sci Rep* 8(1): 1214.
7. Malik P, et al. (1996) Role of capsid structure and membrane protein processing in determining the size and copy number of peptides displayed on the major coat protein of filamentous bacteriophage. *J Mol Biol* 260(1): 9-21.
8. Ryvkin A, et al. (2018) Phage display peptide libraries: deviations from randomness and correctives. *Nucleic Acids Res* 46(9):e52.
9. Matochko W L, Cory Li S, Tang S K Y, Derda R (2014) Prospective identification of parasitic sequences in phage display screens. *Nucleic Acids Res* 42(3): 1784-98.
10. Opferman J T (2015) Attacking cancer's Achilles heel: antagonism of anti-apoptotic BCL-2 family members. *FEBS J*. doi:10.1111/febs.13472.
11. Moldoveanu T, Follis A V, Kriwacki R W, Green D R (2014) Many players in BCL-2 family affairs. *Trends Biochem Sci* 39(3): 101-111.
12. Foight G W, Keating A E (2015) Locating Herpesvirus Bcl-2 Homologs in the Specificity Landscape of Anti-Apoptotic Bcl-2 Proteins. *J Mol Biol* 427(15):2468-2490.
13. Souers A J, et al. (2013) ABT-199, a potent and selective BCL-2 inhibitor, achieves antitumor activity while sparing platelets. *Nat Med* 19(2):202-208.
14. Kotschy A, et al. (2016) The MCL1 inhibitor S63845 is tolerable and effective in diverse cancer models. *Nature* 538(7626):477-482.
15. Montero J, Letai A (2018) Why do BCL-2 inhibitors work and where should we use them in the clinic? *Cell Death Differ* 25(1):56-64.
16. Oltersdorf T, et al. (2005) An inhibitor of Bcl-2 family proteins induces regression of solid tumours. *Nature* 435(7042):677-81.
17. Lessene G, et al. (2013) Structure-guided design of a selective BCL-XL inhibitor. *Nat Chem Biol* 9(6):390-397.
18. Schoenwaelder S M, et al. (2011) Bcl-xL-inhibitory BH3 mimetics can induce a transient thrombocytopathy that undermines the hemostatic function of platelets. *Blood* 118(6).
19. Dutta S, Chen T S, Keating A E (2013) Peptide ligands for pro-survival protein Bfl-1 from computationally guided library screening. *ACS Chem Biol* 8(4):778-88.

20. Foight G W, Ryan J A, Gulla S V, Letai A, Keating A E (2014) Designed BH3 Peptides with High Affinity and Specificity for Targeting Mcl-1 in Cells. *ACS Chem Biol* 9(9): 1962-8.
21. Dutta S, et al. (2015) Potent and specific peptide inhibitors of human pro-survival protein Bcl-xL. *J Mol Biol* 427(6 Pt B): 1241-53.
22. Berger S, et al. (2016) Computationally designed high specificity inhibitors delineate the roles of BCL2 family proteins in cancer. *Elife* 5:1422-1432.
23. Rezaei Araghi R, et al. (2018) Iterative optimization yields Mcl-1-targeting stapled peptides with selective cytotoxicity to Mcl-1-dependent cancer cells. *Proc Natl Acad Sci USA* 115(5):E886-E895.
24. Procko E, et al. (2014) A computationally designed inhibitor of an Epstein-Barr viral Bcl-2 protein induces apoptosis in infected cells. *Cell* 157(7): 1644-1656.
25. Jenson J M, Ryan J A, Grant R A, Letai A, Keating A E (2017) Epistatic mutations in PUMA BH3 drive an alternate binding mode to potently and selectively inhibit anti-apoptotic Bfl-1. *Elife* 6:e25541.
26. Reich L L, Dutta S, Keating A E (2015) SORTCERY-A High-Throughput Method to Affinity Rank Peptide Ligands. *J Mol Biol* 427(11):2135-50.
27. Reich L L, Dutta S, Keating A E (2016) Generating High-Accuracy Peptide-Binding Data in High Throughput with Yeast Surface Display and SORTCERY. *Methods Mol Biol* 1414:233-47.
28. Smola A J, Scholkopf B (2004) A tutorial on support vector regression. *Stat Comput* 14(3): 199-222.
29. Dutta S, Chen T S, Keating A E (2013) Peptide ligands for pro-survival protein Bfl-1 from computationally guided library screening. *ACS Chem Biol* 8(4):778-88.
30. DeBartolo J, et al. (2014) Genome-Wide Prediction and Validation of Peptides That Bind Human Prosurvival Bcl-2 Proteins. *PLoS Comput Biol* 10(6):e1003693.
31. Grigoryan G, Reinke A W, Keating A E (2009) Design of protein-interaction specificity gives selective bZIP-binding peptides. *Nature* 458(7240):859-64.
32. Ryan J, Letai A (2013) BH3 profiling in whole cells by fluorimeter or FACS. *Methods* 61(2): 156-164.
33. Salvat R S, et al. (2017) Computationally optimized deimmunization libraries yield highly mutated enzymes with low immunogenicity and enhanced activity. *Proc Natl AcadSci USA* 114(26):E5085-E5093.
34. Negron C, Keating A E (2014) A set of computationally designed orthogonal antiparallel homodimers that expands the synthetic coiled-coil toolkit. *J Am Chem Soc* 136(47): 16544-56.
35. Potapov V, Kaplan J B, Keating A E (2015) Data-driven prediction and design of bZIP coiled-coil interactions. *PLoS Comput Biol* 1 1(2):e1004046.
36. Bedbrook C N, Yang K K, Rice A J, Gradinaru V, Arnold F H (2017) Machine learning to design integral membrane channelrhodopsins for efficient eukaryotic expression and plasma membrane localization. *PLOS Comput Biol* 13(10):e1005786.
37. Romero P A, Krause A, Arnold F H (2013) Navigating the protein fitness landscape with Gaussian processes. *Proc Natl Acad Sci USA* 110(3):E 193-201.
38. Adams R M, Mora T, Walczak A M, Kinney J B (2016) Measuring the sequence-affinity landscape of antibodies with massively parallel titration curves. *Elife* 5. doi: 10.7554/eLife.23156.
39. Chen T S, Palacios H, Keating A E (2013) Structure-based redesign of the binding specificity of anti-apoptotic Bcl-x(L). *J Mol Biol* 425(1): 171-85.
40. Jacobs T M, Yumerefendi H, Kuhlman B, Leaver-Fay A (2015) SwiftLib: rapid degenerate-codon-library optimization through dynamic programming. *Nucleic Acids Res* 43(5):e34.
41. Chica R A, Moore M M, Allen B D, Mayo S L (2010) Generation of longer emission wavelength red fluorescent proteins using computationally designed libraries. *Proc Natl Acad Sci USA* 107(47):20257-62.
42. Verma D, Grigoryan G, Bailey-Kellogg C (2018) Pareto optimization of combinatorial mutagenesis libraries. *IEEE/ACM Trans Comput Biol Biomforma:*1-1.
43. Fowler D M, et al. (2010) High-resolution mapping of protein sequence-function relationships. *Nat Methods* 7(9):741-6.
44. Herman M D, et al. (2008) Completing the family portrait of the anti-apoptotic Bcl-2 proteins: Crystal structure of human Bfl-1 in complex with Bim. *FEBS Lett* 582(25-26):3590-3594.
45. Dutta S, et al. (2010) Determinants of BH3 binding specificity for Mcl-1 versus Bcl-xL. *J Mol Biol* 398(5): 747-62.
46. Chao G, et al. (2006) Isolating and engineering human antibodies using yeast surface display. *Nat Protoc* 1 (2):755-68.
47. Roehrl M H A, Wang J Y, Wagner G (2004) A General Framework for Development and Data Analysis of Competitive High-Throughput Screens for Small-Molecule Inhibitors of Protein-Protein Interactions by Fluorescence Polarization[†]. *Biochemistry* 43(51): 16056-16066.
48. Otwinowski Z, Minor W (1997) [20] Processing of X-ray diffraction data collected in oscillation mode. *Methods Enzymol* 276:307-326.
49. McCoy A J, et al. (2007) Phaser crystallographic software. *J Appl Crystallogr* 40(Pt 4):658-674.
50. Emsley P, Lohkamp B, Scott W G, Cowtan K (2010) Features and development of Coot. *Acta Crystallogr D Biol Crystallogr* 66(Pt 4):486-501.
51. Koss B, et al. (2016) Defining specificity and on-target activity of BH3-mimetics using engineered B-ALL cell lines. *Oncotarget*. doi:10.18632/oncotarget.7204.
52. Edgar R C (2010) Search and clustering orders of magnitude faster than BLAST. *Bioinformatics* 26(19): 2460-2461.
53. Kingsford C L, Chazelle B, Singh M (2005) Solving and analyzing side-chain positioning problems using linear and integer programming. *Bioinformatics* 21(7): 1028-1039.

Set (B)

1. Chatr-Aryamontri A, Oughtred R, Boucher L, Rust J, Chang C, Kolas N K, et al. The BioGRID interaction database: 2017 update. Nucleic Acids Res. 2017; 45: D369-D379. doi:10.1093/nar/gkw1102
2. Arkin M R, Tang Y, Wells J A. Small-molecule inhibitors of protein-protein interactions: progressing toward the reality. Chem Biol. 2014; 21: 1102-14. doi:10.1016/j.chembiol.2014.09.001
3. Chames P, Van Regenmortel M, Weiss E, Baty D. Therapeutic antibodies: successes, limitations and hopes for the future. Br J Pharmacol. 2009; 157: 220-33. doi:10.1111/j.1476-5381.2009.00190.x
4. Eckert D M, Shi Y, Kim S, Welch B D, Kang E, Poff E S, et al. Characterization of the steric defense of the HIV-1 gp41 N-trimer region. Protein Sci. 2008; 17: 2091-100. doi:10.1110/ps.038273.108
5. Kuang X, Dhroso A, Han J G, Shyu C R, Korkin D. DOMMINO 2.0: Integrating structurally resolved protein-, RNA-, and DNA-mediated Macromolecular interactions. Database. 2016; 2016: 1-12. doi:10.1093/database/bav114
6. Frappier V, Duran M, Keating A E. PixelDB: Protein-peptide complexes annotated with structural conservation of the peptide binding mode. Protein Sci. 2018; 27: 276-285. doi:10.1002/pro.3320
7. Tompa P, Davey N E, Gibson T J, Babu M M. A million peptide motifs for the molecular biologist. Mol Cell. 2014; 55: 161-9. doi:10.1016/j.molcel.2014.05.032
8. Rezaei Araghi R, Bird G H, Ryan J A, Jenson J M, Godes M, Pritz J R, et al. Iterative optimization yields Mcl-1-targeting stapled peptides with selective cytotoxicity to Mcl-1-dependent cancer cells. Proc Natl Acad Sci USA. 2018; 115: E886-E895. doi:10.1073/pnas.1712952115
9. Walensky L D, Bird G H. Hydrocarbon-Stapled Peptides: Principles, Practice, and Progress. J Med Chem. 2014; 57: 6275-6288. doi:10.1021/jm4011675
10. Bird G H, Mazzola E, Opoku-Nsiah K, Lammert M A, Godes M, Neuberg D S, et al. Biophysical determinants for cellular uptake of hydrocarbon-stapled peptide helices. Nat Chem Biol. 2016; 12: 845-52. doi:10.1038/nchembio.2153
11. Schwarze S R, Ho A, Vocero-Akbani A, Dowdy S F. In vivo protein transduction: delivery of a biologically active protein into the mouse. Science. 1999; 285: 1569-72.
12. Nischan N, Herce H D, Natale F, Bohlke N, Budisa N, Cardoso M C, et al. Covalent attachment of cyclic TAT peptides to GFP results in protein delivery into live cells with immediate bioavailability. Angew Chem Int Ed Engl. 2015; 54: 1950-3. doi:10.1002/anie.201410006
13. Qian Z, Martyna A, Hard R L, Wang J, Appiah-Kubi G, Coss C, et al. Discovery and Mechanism of Highly Efficient Cyclic Cell-Penetrating Peptides. Biochemistry. 2016; 55: 2601-12. doi:10.1021/acs.biochem.6b00226
14. Kumar M, Gupta D, Singh G, Sharma S, Bhat M, Prashant C K, et al. Novel polymeric nanoparticles for intracellular delivery of peptide Cargos: antitumor efficacy of the BCL-2 conversion peptide NuBCP-9. Cancer Res. 2014; 74: 3271-81. doi:10.1158/0008-5472.CAN-13-2015
15. Fleishman S J, Whitehead T A, Ekiert D C, Dreyfus C, Corn J E, Strauch E-M, et al. Computational design of proteins targeting the conserved stem region of influenza hemagglutinin. Science. 2011; 332: 816-21. doi:10.1126/science.1202617
16. Berger S, Procko E, Margineantu D, Lee E F, Shen B W, Zelter A, et al. Computationally designed high specificity inhibitors delineate the roles of BCL2 family proteins in cancer. Elife. 2016; 5. doi:10.7554/eLife.20352
17. Roberts K E, Cushing P R, Boisguerin P, Madden D R, Donald B R. Computational design of a PDZ domain peptide inhibitor that rescues CFTR activity. PLOS ComputBiol. 2012; 8: el002477. doi:10.1371/journal.pcbi.1002477
18. Chevalier A, Silva D-A, Rocklin G J, Hicks D R, Vergara R, Murapa P, et al. Massively parallel de novo protein design for targeted therapeutics. Nature. Nature Publishing Group; 2017; 550: 74-79. doi:10.1038/nature23912
19. Arkadash V, Yosef G, Shirian J, Cohen I, Horev Y, Grossman M, et al. Development of High Affinity and High Specificity Inhibitors of Matrix Metalloproteinase 14 through Computational Design and Directed Evolution. J Biol Chem. 2017; 292: 3481-3495. doi:10.1074/jbc.M116.756718
20. Feng X, Barth P. A topological and conformational stability alphabet for multipass membrane proteins. Nat Chem Biol. 2016; 12: 167-173. doi:10.1038/nchembio.2001
21. Debartolo J, Dutta S, Reich L, Keating A E. Predictive Bcl-2 family binding models rooted in experiment or structure. J Mol Biol. Elsevier Ltd; 2012; 422: 124-144. doi:10.1016/j.jmb.2012.05.022
22. DeBartolo J, Taipale M, Keating A E. Genome-Wide Prediction and Validation of Peptides That Bind Human Prosurvival Bcl-2 Proteins. PLOS Comput Biol. 2014; 10: e1003693. doi:10.1371/journal.pcbi.1003693
23. Femandez-Fuentes N, Oliva B, Fiser A. A supersecondary structure library and search algorithm for modeling loops in protein structures. Nucleic Acids Res. 2006; 34: 2085-97. doi:10.1093/nar/gkl 156
24. Mackenzie C O, Grigoryan G. Protein structural motifs in prediction and design. Curr Opin Struct Biol. 2017; 44: 161-167. doi:10.1016/j.sbi.2017.03.012
25. Vanhee P, Verschueren E, Baeten L, Stricher F, Serrano L, Rousseau F, et al. BriX: A database of protein building blocks for structural analysis, modeling and design. Nucleic Acids Res. 2011; 39: 435-442. doi:10.1093/nar/gkq972
26. Jacobs T M, Williams B, Williams T, Xu X, Eletsky A, Federizon J F, et al. Design of structurally distinct proteins using strategies inspired by evolution. Science. 2016; 352: 687-90. doi:10.1126/science.aad8036
27. Mackenzie C O, Zhou J, Grigoryan G. Tertiary alphabet for the observable protein structural universe. Proc Natl Acad Sci USA. 2016; 201607178. doi:10.1073/pnas.1607178113
28. Zheng F, Grigoryan G. Sequence statistics of tertiary structural motifs reflect protein stability. PLoS One. 2017; 12: 1-25. doi:10.1371/journal.pone.0178272
29. Zhou Z, Grigoryan G. A general-purpose protein design framework based on mining sequence-structure relationships in experimentally-derived protein structures. To Appear bioarxiv.org.
30. Zheng F, Zhang J, Grigoryan G. Tertiary structural propensities reveal fundamental sequence/structure relationships. Structure. Elsevier Ltd; 2015; 23: 961-971. doi:10.1016/j.str.2015.03.015
31. Opferman J T. Attacking cancer's Achilles heel: antagonism of anti-apoptotic BCL-2 family members. FEBS J. 2016; 283: 2661-75. doi:10.1111/febs.13472
32. Hiraki M, Maeda T, Mehrotra N, Jin C, Alam M, Bouillez A, et al. Targeting MUC1-C suppresses BCL2A1 in triple-negative breast cancer. Signal Transduct Target Ther. 2018; 3: 13. doi:10.1038/s41392-018-0013-x
33. Souers A J, Leverson J D, Boghaert E R, Ackler S L, Catron N D, Chen J, et al. ABT-199, a potent and selective BCL-2 inhibitor, achieves antitumor activity while sparing platelets. Nat Med. 2013; 19: 202-8. doi:10.1038/nm.3048
34. Cang S, Iragavarapu C, Savooji J, Song Y, Liu D. ABT-199 (venetoclax) and BCL-2 inhibitors in clinical development. J Hematol Oncol. 2015; 8: 129. doi:10.1186/s13045-015-0224-3
35. Foight G W, Ryan J A, Gulla S V., Letai A, Keating A E. Designed BH3 peptides with high affinity and specificity for targeting Mcl-1 in cells. ACS Chem Biol. 2014; 9: 1962-1968. doi:10.1021/cb500340w
36. Jenson J M, Ryan J A, Grant R A, Letai A, Keating A E. Epistatic mutations in PUMA BH3 drive an alternate binding mode to potently and selectively inhibit anti-apoptotic Bfl-1. Elife. 2017; 6: 1-23. doi:10.7554/eLife.25541

37. Berger S, Procko E, Margineantu D, Lee E F, Shen B W, Zelter A, et al. Computationally designed high specificity inhibitors delineate the roles of BCL2 family proteins in cancer. Elife. 2016; 5: 1-31. doi:10.7554/eLife.20352

38. Kotschy A, Szlavik Z, Murray J, Davidson J, Maragno A L, Le Toumelin-Braizat G, et al. The MCL1 inhibitor S63845 is tolerable and effective in diverse cancer models. Nature. 2016; 538: 477-482. doi:10.1038/nature19830

39. Reich L, Dutta S, Keating A E. SORTCERY—A High-Throughput Method to Affinity Rank Peptide Ligands. J Mol Biol. 2015; 427: 2135-2150. doi:10.1016/j.jmb.2014.09.025

40. Jenson J M, Xue V, Stretz L, Reich L, Keating A E. Peptide design by optimization on a data-parameterized protein interaction landscape. Proc Natl Acad Sci.

41. Lewis S M, Kuhlman B A. Anchored design of protein-protein interfaces. PLoS One. 2011; 6: e20872. doi:10.1371/journal.pone.0020872

42. Alford R F, Leaver-Fay A, Jeliazkov J R, O'Meara M J, DiMaio F P, Park H, et al. The Rosetta All-Atom Energy Function for Macromolecular Modeling and Design. J Chem Theory Comput. 2017; 13: 3031-3048. doi:10.1021/acs.jctc.7b00125

43. Schymkowitz J, Borg J, Stricher F, Nys R, Rousseau F, Serrano L. The FoldX web server: An online force field. Nucleic Acids Res. 2005; 33: W382-W388. doi:10.1093/nar/gki387

44. Fire E, Gulla S V, Grant R A, Keating A E. Mcl-1-Bim complexes accommodate surprising point mutations via minor structural changes. Protein Sci. 2010; 19: 507-19. doi:10.1002/pro.329

45. Miles J A, Yeo D J, Rowell P, Rodriguez-Marin S, Pask C M, Warriner S L, et al. Hydrocarbon constrained peptides—understanding preorganisation and binding affinity. Chem Sci. 2016; 7: 3694-3702. doi:10.1039/c5sc04048e 46. Gai S A, Wittrup K D. Yeast surface display for protein engineering and characterization. Curr Opin Struct Biol. 2007; 17: 467-73. doi:10.1016/j.sbi.2007.08.012

47. Dutta S, Gulla S, Chen T S, Fire E, Grant R A, Keating A E. Determinants of BH3 Binding Specificity for Mcl-1 versus Bcl-xL. J Mol Biol. 2010; 398: 747-762. doi:10.1016/j.jmb.2010.03.058

48. Dutta S, Chen T S, Keating A E. Peptide ligands for pro-survival protein Bfl-1 from computationally guided library screening. ACS Chem Biol. 2013; 8: 778-88. doi:10.1021/cb300679a 49. Jenson J M, Ryan J A, Grant R A, Letai A, Keating A E. Epistatic mutations in PUMA BH3 drive an alternate binding mode to potently and selectively inhibit anti-apoptotic Bfl-1. Elife. 2017; 6. doi:10.7554/eLife.25541

50. Lee E F, Fedorova A, Zobel K, Boyle M J, Yang H, Perugini M A, et al. Novel Bcl-2 homology-3 domain-like sequences identified from screening randomized peptide libraries for inhibitors of the pro-survival Bcl-2 proteins. J Biol Chem. 2009; 284: 31315-31326. doi:10.1074/jbc.M109.048009

51. Zheng F, Jewell H, Fitzpatrick J, Zhang J, Mierke D F, Grigoryan G. Computational design of selective peptides to discriminate between similar PDZ domains in an oncogenic pathway. J Mol Biol. 2015; 427: 491-510. doi:10.1016/j.jmb.2014.10.014

52. Davey J A, Chica R A. Improving the accuracy of protein stability predictions with multistate design using a variety of backbone ensembles. Proteins Struct Funct Bioinforma. 2014; 82: 771-784. doi:10.1002/prot.24457

53. Procko E, Berguig G Y, Shen B W, Song Y, Frayo S, Convertine A J, et al. A computationally designed inhibitor of an Epstein-Barr viral Bcl-2 protein induces apoptosis in infected cells. Cell. Elsevier Inc.; 2014; 157: 1644-1656. doi:10.1016/j.cell.2014.04.034

54. Kingsford C L, Chazelle B, Singh M. Solving and analyzing side-chain positioning problems using linear and integer programming. Bioinformatics. 2005; 21: 1028-1039. doi:10.1093/bioinformatics/bti 144

55. Grigoryan G, Reinke A W, Keating A E. Design of protein-interaction specificity gives selective bZIP-binding peptides. Nature. Nature Publishing Group; 2009; 458: 859-864. doi:10.1038/nature07885

56. Chaudhury S, Lyskov S, Gray J J. PyRosetta: a script-based interface for implementing molecular modeling algorithms using Rosetta. Bioinformatics. 2010; 26: 689-91. doi:10.1093/bioinformatics/btq007

57. Crooks G E, Hon G, Chandonia J-M, Brenner S E. WebLogo: a sequence logo generator. Genome Res. 2004; 14: 1188-90. doi:10.1101/gr.849004

58. Munoz V, Serrano L. Development of the multiple sequence approximation within the AGADIR model of alpha-helix formation: comparison with Zimm-Bragg and Lifson-Roig formalisms. Biopolymers. 1997; 41: 495-509. doi:10.1002/(SICI) 1097-0282(19970415)41:5<495::AID-BIP2>3.0.C O; 2-H 59. Gautier R, Douguet D, Antonny B, Drin G. HELIQUEST: a web server to screen sequences with specific alpha-helical properties. Bioinformatics. 2008; 24: 2101-2. doi:10.1093/bioinformatics/btn392

60. Larkin M A, Blackshields G, Brown N P, Chenna R, McGettigan P A, McWilliam H, et al. Clustal W and Clustal X version 2.0. Bioinformatics. 2007; 23: 2947-8. doi:10.1093/bioinformatics/btm404

61. Henikoff S, Henikoff J G. Amino acid substitution matrices from protein blocks. Proc Natl Acad Sci USA. 1992; 89: 10915-10919. doi:10.1073/pnas.89.22.10915

62. UniProt Consortium T. UniProt: the universal protein knowledgebase. Nucleic Acids Res. 2018; 46: 2699. doi:10.1093/nar/gky092

63. Berman H M. The Protein Data Bank. Nucleic Acids Res. 2000; 28: 235-242. doi:10.1093/nar/28.1.235

64. Needleman S B, Wunsch C D. A general method applicable to the search for similarities in the amino acid sequence of two proteins. J Mol Biol. 1970; 48: 443-53.

65. McConkey B J, Sobolev V, Edelman M. Discrimination of native protein structures using atom-atom contact scoring. Proc Natl Acad Sci USA. 2003; 100: 3215-20. doi:10.1073/pnas.0535768100

66. Wang S, Peng J, Xu J. Alignment of distantly related protein structures: Algorithm, bound and implications to homology modeling. Bioinformatics. 2011; 27: 2537-2545. doi:10.1093/bioinformatics/btr432

67. Otwinowski Z, Minor W. [20] Processing of X-ray diffraction data collected in oscillation mode. Methods Enzymol. 276: 307-326. doi:10.1016/S0076-6879(97) 76066-X 68. McCoy A J, Grosse-Kunstleve R W, Adams P D, Winn M D, Storoni L C, Read R J. Phaser crystallographic software. J Appl Crystallogr. 2007; 40: 658-674. doi: 10.1107/S0021889807021206

69. Emsley P, Lohkamp B, Scott W G, Cowtan K. Features and development of Coot. Acta Crystallogr D Biol Crystallogr. 2010; 66: 486-501. doi:10.1107/S0907444910007493

70. Czabotar P E, Lee E F, Thompson G V, Wardak A Z, Fairlie W D, Colman P M. Mutation to Bax beyond the BH3 domain disrupts interactions with pro-survival proteins and promotes apoptosis. J Biol Chem. 2011; 286: 7123-31. doi:10.1074/jbc.M110.161281

What is claimed is:

1. A compound comprising peptide comprising an amino acid sequence selected from the group consisting of:

RSELEVVQELVRIGDIVVAYFER; (SEQ ID NO: 85)

RSQYEVIQELIRIGDIVLAYFER; (SEQ ID NO: 86)

DVVLSVAETLRELADRLYEEINT; (SEQ ID NO: 87)

QRVVHIAAGLRRTGDQLEAYG; (SEQ ID NO: 88)

RRVVQIAAGLRRAGDQLEKYG; (SEQ ID NO: 89)

SYVDKIADVMREVAEKINSDLT; (SEQ ID NO: 90)

SLLEKLAEYLRQMADEINKKYVK; (SEQ ID NO: 91)

QRIIWIAAELRRAADELDKQIER; (SEQ ID NO: 92)

QRIIWIAAELRRAADQLDAQIER; (SEQ ID NO: 93)

RWIDQIAQFLRRIGDHIEKYIER; (SEQ ID NO: 94)

RRVDEIAQILRRIGDNVTTYIER; (SEQ ID NO: 95)

QWLRWVIAELIRIADEFHAQYER; (SEQ ID NO: 96)
and

QWLRDVVAELARIADEFHAQYER. (SEQ ID NO: 97)

2. The compound of claim 1, comprising a peptide comprising an amino acid sequence selected from the group consisting of:

RSELEVVQELVRIGDIVVAYFER; (SEQ ID NO: 85)

RSQYEVIQELIRIGDIVLAYFER; (SEQ ID NO: 86)
and

-continued

```
                                                 (SEQ ID NO: 87)
DVVLSVAETLRELADRLYEEINT.
```

3. The compound of claim 1, comprising a peptide comprising an amino acid sequence selected from the group consisting of:

```
                                                 (SEQ ID NO: 88)
QRVVHIAAGLRRTGDQLEAYG;

(SEQ ID NO: 89)
RRVVQIAAGLRRAGDQLEKYG;

(SEQ ID NO: 90)
SYVDKIADVMREVAEKINSDLT;
and (SEQ ID NO: 91)
SLLEKLAEYLRQMADEINKKYVK.
```

4. The compound of claim 1, comprising a peptide comprising an amino acid sequence selected from the group consisting of:

```
                                                 (SEQ ID NO: 92)
QRIIWIAAELRRAADELDKQIER;
and (SEQ ID NO: 93)
QRIIWIAAELRRAADQLDAQIER.
```

5. The compound of claim 1, comprising a peptide comprising an amino acid sequence selected from the group consisting of:

```
                                                 (SEQ ID NO: 94)
RWIDQIAQFLRRIGDHIEKYIER;
and (SEQ ID NO: 95)
RRVDEIAQILRRIGDNVTTYIER.
```

6. The compound of claim 1, comprising a peptide comprising an amino acid sequence selected from the group consisting of:

```
                                                 (SEQ ID NO: 96)
QWLRWVIAELIRIADEFHAQYER;
and (SEQ ID NO: 97)
QWLRDVVAELARIADEFHAQYER.
```

7. A pharmaceutical composition comprising the compound of claim 1.

8. A method of treating cancer comprising the administering of the compound of claim 1.

9. A method for detecting a BH3 binding domain peptide in a cell, the method comprising:
  a) providing cell;
  b) contacting the cell with a compound claim 1; and
  d) determining whether the compound binds to the cell.

\* \* \* \* \*